US012728220B2

(12) United States Patent
Peiris et al.

(10) Patent No.: US 12,728,220 B2
(45) Date of Patent: Sep. 8, 2026

(54) BREATHING ASSISTANCE APPARATUS

(71) Applicant: Fisher & Paykel Healthcare Limited, Auckland (NZ)

(72) Inventors: Malik Tivanka Rajiv Peiris, Auckland (NZ); Simei Gomes Wysoski, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 361 days.

(21) Appl. No.: 18/245,834

(22) PCT Filed: Sep. 21, 2021

(86) PCT No.: PCT/IB2021/058563
§ 371 (c)(1),
(2) Date: Mar. 17, 2023

(87) PCT Pub. No.: WO2022/058982
PCT Pub. Date: Mar. 24, 2022

(65) Prior Publication Data

US 2024/0024602 A1 Jan. 25, 2024

Related U.S. Application Data

(60) Provisional application No. 63/081,230, filed on Sep. 21, 2020.

(51) Int. Cl.

*A61M 16/00* (2006.01)
*A61M 16/08* (2006.01)
*A61M 16/16* (2006.01)

(52) U.S. Cl.

CPC ...... *A61M 16/026* (2017.08); *A61M 16/0051* (2013.01); *A61M 16/0066* (2013.01);
(Continued)

(58) Field of Classification Search

CPC .......... A61M 16/0051; A61M 16/0066; A61M 16/024; A61M 16/026; A61M 16/0875;
(Continued)

(56) References Cited

U.S. PATENT DOCUMENTS 3,724,454 A 4/1973 Brown
3,806,102 A 4/1974 Valenta et al.
(Continued)

FOREIGN PATENT DOCUMENTS

EP 0 777 507 B1 6/1997
EP 1 287 843 A2 3/2003
(Continued)

OTHER PUBLICATIONS

Bernstein, Bill. DreamStation CPAP UI, Dec. 19, 2015, Bill Bernstein—UI, UX, Jan. 16, 2024, Accessed on the internet: https://bernstein.work/dreamstation-cpap (Year: 2015).
(Continued)

*Primary Examiner* — Joseph D. Boecker
(74) *Attorney, Agent, or Firm* — Knobbe, Martens, Olson & Bear, LLP

(57) ABSTRACT

A breathing assistance apparatus for providing respiratory therapy such as bubble CPAP therapy comprises a flow generator, a gases flow pathway, a pressure regulator, a gases property sensor and a controller. The controller of the apparatus can be configured to detect the presence of bubbling in the pressure regulator based on the at least one waveform characteristic from a measured flow and/or pressure waveform.

19 Claims, 20 Drawing Sheets

(52) U.S. Cl.
CPC ............... *A61M 2016/0027* (2013.01); *A61M 2016/0033* (2013.01); *A61M 2016/0039* (2013.01); *A61M 2016/0042* (2013.01); *A61M 16/0875* (2013.01); *A61M 16/16* (2013.01); *A61M 2205/3348* (2013.01); *A61M 2205/3389* (2013.01)

(58) Field of Classification Search
CPC .......... A61M 16/16; A61M 2205/3348; A61M 2205/3389; A61M 2016/0027; A61M 2016/0033; A61M 2016/0039; A61M 2016/0042; A61M 2240/00
See application file for complete search history.

(56) References Cited

U.S. PATENT DOCUMENTS 4,192,836 A 3/1980 Bartscher et al.
4,459,983 A * 7/1984 Beyreuther ........... A61M 16/00 137/251.1
5,743,879 A 4/1998 Kriesel
5,943,473 A 8/1999 Levine
6,805,120 B1 10/2004 Jeffrey et al.
7,044,129 B1 5/2006 Truschel et al.
7,305,987 B2 12/2007 Scholller et al.
D582,427 S 12/2008 Neuhaus
D657,368 S 4/2012 Magee et al.
D667,838 S 9/2012 Magee et al.
8,439,031 B1 5/2013 Rothermel et al.
D739,427 S 9/2015 Jung et al.
D761,863 S 7/2016 Debitsch et al.
D772,252 S 11/2016 Myers et al.
9,737,675 B2 8/2017 Frame et al.
D806,717 S 1/2018 Bae et al.
10,016,169 B2 7/2018 Meador et al.
D831,059 S 10/2018 Bao
D835,657 S 12/2018 Anzures et al.
D835,666 S 12/2018 Saleh et al.
D835,667 S 12/2018 Saleh et al.
10,226,200 B2 3/2019 Vassallo et al.
D846,583 S 4/2019 Martin et al.
10,314,990 B2 6/2019 Richards-Kortum et al.
10,342,950 B2 7/2019 Bath et al.
10,369,309 B2 8/2019 Feldhahn et al.
D885,410 S 5/2020 Butler
D887,441 S 6/2020 Lorca Norambuena
D892,141 S 8/2020 Clifford et al.
D892,142 S 8/2020 Clifford et al.
D892,832 S 8/2020 Onuma
D892,833 S 8/2020 Onuma
D893,547 S 8/2020 Dumas et al.
10,864,343 B2 12/2020 Bath et al.
10,905,843 B2 2/2021 Smith
D913,304 S 3/2021 VanDuyn et al.
D914,039 S 3/2021 Zimmerman et al.
D914,726 S 3/2021 Gouliard et al.
D916,721 S 4/2021 Kirkeby
D916,743 S 4/2021 Sim et al.
D916,878 S 4/2021 Kim et al.
D918,224 S 5/2021 Velamuri et al.
D922,405 S 6/2021 Norman
11,039,797 B2 6/2021 Meador et al.
D928,190 S 8/2021 Hartman et al.
D928,813 S 8/2021 Nurutdinov et al.
11,135,388 B2 10/2021 Ronayne
D940,729 S 1/2022 Campbell et al.
D941,849 S 1/2022 Knowles et al.
D978,157 S 2/2023 Han et al.
12,048,810 B2 7/2024 Dennis et al.
D1,092,528 S 9/2025 Campbell et al.
2003/0029451 A1 2/2003 Blair et al.
2003/0047185 A1* 3/2003 Olsen ................ A61M 16/0683 128/203.22
2004/0040559 A1 3/2004 Moody
2004/0244804 A1 12/2004 Olsen et al.
2005/0150494 A1 7/2005 DeVries et al.
2006/0048782 A1 3/2006 Gossweiler
2006/0174882 A1 8/2006 Jagger et al.
2009/0107504 A1 4/2009 McAuley
2009/0194108 A1* 8/2009 Newman, Jr. ..... A61M 16/0666 128/204.18
2009/0301482 A1 12/2009 Burton
2010/0051029 A1 3/2010 Jafari
2010/0078024 A1 4/2010 Andrieux et al.
2010/0228224 A1 9/2010 Pyles
2011/0308518 A1 12/2011 McGroary et al.
2012/0220817 A1* 8/2012 Castillon ........... A61M 16/0627 600/22
2012/0260718 A1 10/2012 Sparks et al.
2012/0272964 A1 11/2012 Loser
2013/0228180 A1 9/2013 Ahmad et al.
2013/0267793 A1 10/2013 Meador et al.
2014/0000606 A1 1/2014 Doyle et al.
2014/0014110 A1 1/2014 Adams
2014/0166013 A1* 6/2014 Stenzler ................ A61M 16/00 29/890.09
2014/0277914 A1 9/2014 Fish et al.
2015/0059764 A1 3/2015 Metelits
2015/0075524 A1* 3/2015 Millar ................... A61M 16/04 128/203.27
2015/0083123 A1 3/2015 Tero
2015/0186023 A1 7/2015 Alisanski et al.
2015/0258291 A1* 9/2015 Richards-Kortum ........................ A61M 16/0066 128/205.25
2016/0199601 A1 7/2016 Peiris et al.
2016/0256642 A1 9/2016 Soysa et al.
2017/0224234 A1 8/2017 Ahlmen et al.
2017/0304570 A1 10/2017 Landis et al.
2018/0015245 A1 1/2018 Frame et al.
2018/0071469 A1 3/2018 Oldfield et al.
2018/0110948 A1 4/2018 Dellaca et al.
2018/0140927 A1 5/2018 Kito et al.
2019/0083001 A1 3/2019 Stamatopoulos et al.
2019/0160241 A1 5/2019 Boulanger
2019/0167937 A1 6/2019 Sims
2019/0184128 A1 6/2019 Lucio
2019/0232009 A1* 8/2019 Ronayne ........... A61M 16/0816
2020/0246548 A1 8/2020 Bill
2021/0023318 A1* 1/2021 Tatum ................. A61M 16/024
2021/0038088 A1 2/2021 Atallah et al.
2021/0181932 A1 6/2021 Han et al.
2021/0228832 A1* 7/2021 Parrish .............. A61M 16/0666
2021/0299396 A1* 9/2021 Mohan .............. A61M 16/0883
2022/0168536 A1 6/2022 Hsu et al.
2022/0347423 A1 11/2022 Babbage et al.
2025/0381358 A1 12/2025 Hsu et al.

FOREIGN PATENT DOCUMENTS

EP 2 123 321 A1 11/2009
EP 1 061 981 B1 9/2010
EP 2 644 220 A1 10/2013
JP 52-105996 8/1977
WO WO 2005/063323 7/2005
WO WO 2009/145646 12/2009
WO WO 2010/033429 3/2010
WO WO 2013/067580 5/2013
WO WO 2013/154439 10/2013
WO WO 2014/085431 A1 6/2014
WO WO 2015/165845 11/2015
WO WO 2016/133406 8/2016
WO 2017/096428 A1 6/2017
WO WO 2017/126980 7/2017
WO WO 2018/033863 2/2018
WO WO 2018/042355 3/2018
WO WO 2019/193535 A1 10/2019
WO WO 2019/245391 A1 12/2019
WO WO 2020/122739 6/2020
WO WO 2020/188526 A1 9/2020
WO WO 2021/046537 3/2021
WO WO 2021/049953 3/2021
WO WO 2022/058982 3/2022

(56) References Cited

FOREIGN PATENT DOCUMENTS

OTHER PUBLICATIONS

Worthington, Michael. Warm Touch GUI Redesign, Nov. 2, 2018, Michael Worthington Designs, Jan. 16, 2024, Accessed on the internet: https://www.michaelworthingtondesigns.com/ui-work/ (Year: 2018).

* cited by examiner

BREATHING ASSISTANCE APPARATUS

FIELD OF THE DISCLOSURE

The present disclosure relates to breathing assistance apparatuses. In particular, the present disclosure relates to the detection of bubbling in a breathing assistance apparatus and/or estimating flow and/or pressure in a gases flow pathway.

BACKGROUND

Breathing assistance apparatuses are used in various environments such as hospital, medical facility, residential care, or home environments to deliver a flow of gases to users or patients. A breathing assistance or respiratory therapy apparatus (collectively, "respiratory apparatus" or "respiratory devices") may be used to deliver a flow of gases and optionally additionally or alternatively deliver supplementary oxygen or other gases. The breathing assistance apparatus may also comprise a humidification apparatus to deliver heated and humidified gases. As discussed in more detail below the humidification apparatus may be separate to, or part of the breathing assistance apparatus. A breathing assistance apparatus may allow adjustment and control over characteristics of the gases flow, including flow rate, temperature, gases concentration, humidity, pressure, etc. Sensors, such as flow sensors and/or pressure sensors, are used to measure characteristics of the gases flow.

SUMMARY

In an aspect of the disclosure there is provided a breathing assistance apparatus for providing respiratory therapy, the breathing assistance apparatus comprising:

- a flow generator, the flow generator configured to provide a flow of gases to an inspiratory conduit at a target flow rate,
- at least one gases property sensor, the at least one gases property sensor configured to measure a flow rate and/or a pressure of the gases in a gases flow pathway,
- wherein the gases flow pathway comprises at least the inspiratory conduit configured to be connected to a patient interface, and an expiratory conduit configured to be connected to a patient interface and a pressure regulator, the pressure regulator comprising a chamber with a column of a liquid into which an end portion of the expiratory conduit is submerged,
- a controller, the controller configured to:
  - determine at least one waveform characteristic based on a waveform of the measured flow and/or pressure, and
  - based on the at least one waveform characteristic, determine whether bubbling is occurring in the pressure regulator.

Determination of whether bubbling is occurring may be based on determining pressure and/or flow oscillations in the waveform indicative of bubbling in the pressure regulator.

The controller may be configured to display whether bubbling is occurring in the pressure regulator on a display.

The controller may be configured to generate an alarm based on whether bubbling is occurring in the pressure regulator.

The controller may be configured to generate the alarm if it is determined bubbling is not occurring in the pressure regulator.

The controller may be configured to generate the alarm if it is determined: the percentage of time bubbling is occurring over a time period is below a threshold, or the percentage of time bubbling is not occurring over a time period is above a threshold.

The alarm may comprise one or more of:

- an audio alarm,
- a visual alarm.

The apparatus may comprise a display, optionally the display comprises one or more of: a touchscreen and/or one or more mechanical input devices.

The controller may automatically select a respiratory therapy mode based on whether bubbling is occurring in the pressure regulator.

The respiratory therapy mode may comprise a bubble CPAP therapy mode and a high flow therapy mode.

Detection of bubbling may be occurring constantly or intermittently while the apparatus is operating in a non-bubble CPAP mode.

The controller is configured to generate an alarm when bubbling is detected in a non-bubble CPAP mode.

The determination of whether bubbling is occurring may be based on at least one waveform characteristic exceeding an associated threshold.

The determination of whether bubbling is occurring may be based on a model, the model comprising one or more waveform characteristic factors associated with each waveform characteristic.

The model may be a regression model.

The one or more waveform characteristic factors may be determined experimentally.

The determination of whether bubbling is occurring in the pressure regulator may be over a time period.

The at least one waveform characteristic may comprise or be based on one or more of:

- an amplitude of the waveform,
- a distance between positive peaks of the waveform,
- a magnitude of the amplitude difference between consecutive positive and negative peaks of the waveform.

The at least one waveform characteristic may comprise at least one amplitude characteristic, and wherein the amplitude characteristic comprises one or more of:

- an average of the amplitude of the positive peaks of the waveform, optionally over a time window,
- a standard deviation of the amplitude of the positive peaks of the waveform, optionally over a time window.

The at least one waveform characteristic may comprise at least one peak distance characteristic, and wherein the peak distance characteristic comprises one or more of:

- an average distance between positive peaks of the waveform, optionally over a time window,
- a standard deviation of the distance between positive peaks of the waveform optionally over a time window.

The at least one waveform characteristic may comprise at least one peak difference characteristic, and wherein the peak difference characteristic comprises one or more of:

- an average of the magnitude of the amplitude difference between consecutive positive and negative peaks of the waveform, optionally over a time window, a standard deviation of the magnitude of the amplitude difference between consecutive positive and negative peaks of the waveform, optionally over a time window.

The controller may be configured to apply a high pass and/or a low pass filter to the measurement of the flow rate or pressure and/or the waveform.

The waveform may be configured to be divided into a one or more time windows, and optionally wherein the determination of whether bubbling is occurring is made for each time window.

Each time window may be approximately two seconds.

Each time window may overlap with a preceding time window, and/or a subsequent time window.

The time window overlap may be approximately 1.5 seconds.

The determination of whether bubbling is occurring may be a probability of bubbling occurring between 0 and 1.

Bubbling may be determined to be occurring when the probability of bubbling occurring is greater than 0.5.

The determination of whether bubbling is occurring may be based on an ambient pressure.

The determination bubbling is occurring may be based on an ambient temperature

The determination bubbling is occurring may be based on an altitude of the apparatus.

The determination bubbling is occurring may be based on a water level in a humidifier located in the gases pathway.

The apparatus may be configured to provide a combination of ambient air, and a supplementary gas, and the determination of whether bubbling is occurring is based on the ratio of ambient air to supplementary gas.

The determination of whether bubbling is occurring may be based on a conduit characteristic of the inspiratory conduit and/or the expiratory conduit.

The conduit characteristic may comprise one or more of:

conduit length, conduit diameter, a conduit type.

The determination of whether bubbling is occurring may be based on a characteristic of the patient interface.

The controller may be configured to monitor a pressure of the gases in the gases flow pathway.

The controller may be configured to generate an alarm when the pressure of the gases flow exceeds a threshold.

The breathing assistance apparatus may provide CPAP therapy

The breathing assistance apparatus may provide bubble CPAP therapy.

The breathing assistance apparatus may comprise a blower for generating the flow of gases.

The breathing assistance apparatus may comprise a humidifier for heating and/or humidifying the flow of gases.

The breathing assistance apparatus may comprise a housing for containing the blower and/or humidifier.

The breathing assistance apparatus may comprise a heated breathing tube.

The blower may be configured to deliver a substantially constant flow of gases and/or a substantially constant pressure.

At least one gases property sensor may be located at one or more of:

in the breathing assistance apparatus, optionally within the flow generator, in a patient interface, in the pressure regulator, in the inspiratory conduit and/or expiratory conduit.

At least one gases property sensor may be located within the gases flow pathway.

The flow generator may be configured to provide a flow of gases to an inspiratory conduit at a target flow rate.

The controller may be configured to determine a waveform based on the measurement of the flow rate and/or pressure of the gases in the gases flow path.

The liquid may be water, or a saline solution.

The controller may be configured to determine that bubbling is intermittent based on the ratio of time bubbling is occurring to time bubbling is not occurring over a time period.

The controller may be configured to determine that bubbling is intermittent when a ratio of the time bubbling is occurring to time bubbling is not occurring is within a range.

The controller may be configured to determine one or more bubbling time metrics based on detection of bubbling during one or more therapy sessions.

The one or more bubbling time metrics is one or more of:

a bubbling index, wherein the bubbling index, wherein the bubbling index is a percentage of the total therapy time for which bubbling is occurring, a no bubbling time for which bubbling is not occurring, a bubbling time for which bubbling is occurring.

Detection of bubbling is occurring in the pressure regulator during a therapy session may indicate that therapy is being provided.

The controller may be configured to upload one or more bubbling time metrics to a server and/or a device.

The controller may be configured to generate an alarm when one or more bubbling time metrics falls below a threshold.

The controller may be configured to indicate that therapy is being provided when one or more bubbling time metrics are above a threshold.

In another aspect of the disclosure there is provided a breathing assistance apparatus for providing respiratory therapy, the breathing assistance apparatus comprising:

a flow generator, the flow generator configured to provide a flow of gases to an inspiratory conduit at a target flow rate, at least one gases property sensor, the at least one gases property sensor configured to measure a flow rate and/or a pressure of the gases in a gases flow pathway, a controller, the controller configured to:

determine at least one waveform characteristic based on a waveform of the measured flow and/or pressure, and based on the at least one waveform characteristic, determine whether bubbling is occurring in a pressure regulator.

It will be appreciated that the above aspect may be combined with any combination of the other aspects (and in particular the above aspects).

In another aspect of the disclosure there is provided a controller for a breathing assistance apparatus for providing respiratory therapy, the controller configured to:

determine at least one waveform characteristic based on a waveform of a measured flow and/or pressure, and based on the at least one waveform characteristic, determine whether bubbling is occurring in a pressure regulator.

It will be appreciated that the above aspect may be combined with any combination of the other aspects (and in particular the above aspects).

In another aspect of the disclosure there is provided a method of detecting bubbling in a pressure regulator of a breathing assistance system, the method comprising:

determining at least one waveform characteristic based on a waveform of a measured flow and/or pressure, and based on the at least one waveform characteristic, determining whether bubbling is occurring in a pressure regulator.

It will be appreciated that the above aspect may be combined with any combination of the other aspects (and in particular the above aspects).

In another aspect of the disclosure there is provided a breathing assistance apparatus for providing respiratory therapy, the breathing assistance apparatus comprising:

- a flow generator, the flow generator configured to provide a flow of gases to an inspiratory conduit (optionally at a target flow rate),
- wherein the gases flow pathway comprises at least the inspiratory conduit configured to be connected to a patient interface, and an expiratory conduit configured to be connected to a pressure regulator the pressure regulator comprising a chamber with a column of water into which an end portion of the expiratory conduit is submerged,
- at least one sensor, the sensor configured to measure at least one characteristic indicative of bubbling in the pressure regulator,
- a controller, the controller configured to:
  - based on the measurement of at least one characteristic indicative of bubbling in the pressure regulator, determine whether bubbling is occurring in the pressure regulator.

It will be appreciated that the above aspect may be combined with any combination of the other aspects (and in particular the above aspects).

In another aspect of the disclosure there is provided a breathing assistance apparatus for providing respiratory therapy, the breathing assistance apparatus comprising:

- a flow generator, the flow generator configured to provide a flow of gases (optionally at a target flow rate),
- at least one sensor, the sensor configured to measure at least one characteristic indicative of bubbling in a pressure regulator,
- a controller, the controller configured to:
  - determine at least one waveform characteristic based on a waveform of the measurement of at least one characteristic indicative of bubbling in the pressure regulator, and
  - based on the at least one waveform characteristic, determine whether bubbling is occurring in the pressure regulator.

It will be appreciated that the above aspect may be combined with any combination of the other aspects (and in particular the above aspects).

In another aspect of the disclosure there is provided a breathing assistance apparatus for providing respiratory therapy, the breathing assistance apparatus comprising:

- a flow generator, the flow generator configured to provide a flow of gases to an inspiratory conduit at a target flow rate,
- wherein the gases flow pathway comprises at least the inspiratory conduit configured to be connected to a patient interface, and an expiratory conduit configured to be connected to a pressure regulator the pressure regulator comprising a chamber with a column of water into which an end portion of the expiratory conduit is submerged,
- at least one sensor, the sensor configured to measure at least one characteristic indicative of bubbling in the pressure regulator,
- a controller, the controller configured to:
  - determine at least one waveform characteristic based on a waveform of the measurement of at least one characteristic indicative of bubbling in the pressure regulator, and
  - based on the at least one waveform characteristic, determine whether bubbling is occurring in the pressure regulator.

It will be appreciated that the above aspect may be combined with any combination of the other aspects (and in particular the above aspects).

In another aspect of the disclosure there is provided a controller for a breathing assistance apparatus for providing respiratory therapy, the controller configured to:

- based on a measurement of at least one characteristic indicative of bubbling in the pressure regulator, determine whether bubbling is occurring in a pressure regulator.

In another aspect of the disclosure there is provided a method of detecting bubbling in a pressure regulator of a breathing assistance system, the method comprising:

- determining at least one waveform characteristic based on a waveform of a measurement of at least one characteristic indicative of bubbling in the pressure regulator, and
- based on the at least one waveform characteristic, determining whether bubbling is occurring in the pressure regulator.

It will be appreciated that the above aspect may be combined with any combination of the other aspects (and in particular the above aspects).

The at least one sensor, may be one or more of:

- a visual sensor (for example a vision sensor) configured to output a signal indicative of an image of the bubbler,
- a water level sensor (for example monitoring the height of the water in the bubbler) configured to output a signal indicative of the surface of the water in the bubbler,
- a microphone, configured to output a signal indicative of the sound generated by the bubbler,
- an optical sensor, configured to output a signal indicative of the optical properties of the liquid in the bubbler,
- a gas flow characteristic sensor, configured to output a signal indicative of a gas flow characteristic, optionally, a flow sensor or a pressure sensor.

The at least one characteristic of bubbling in the pressure regulator may be based on one or more of:

- a signal indicative of an image of the bubbler as an output of a visual sensor,
- a signal indicative of the surface of the water in the bubbler as an output of a water level sensor,
- a signal indicative of the sound generated by the bubbler as an output of a microphone,
- a signal indicative of the optical properties of the liquid in the bubbler as an output of an optical sensor,
- a signal indicative of a gas flow characteristic, as an output of a gas flow characteristic sensor.

The at least one characteristic indicative of bubbling in the pressure regulator may be flow rate and/or a pressure of the gases in a gases flow pathway.

In another aspect of the disclosure there is provided a breathing assistance apparatus for providing respiratory therapy, the breathing assistance apparatus comprising:

- a flow generator, the flow generator configured to provide a flow of gases to an inspiratory conduit,
- a controller, the controller configured to automatically select a respiratory therapy mode based on whether bubbling is occurring in the pressure regulator.

The breathing assistance apparatus may comprise at least one gases property sensor, the at least one gases property sensor configured to measure a flow rate and/or a pressure of the gases in a gases flow pathway.

The controller may be configured to:

determine a waveform based on the measurement of the flow rate and/or pressure of the gases in the gases flow path, and determine at least one waveform characteristic based on the flow and/or pressure waveform, and based on the at least one waveform characteristic, determine whether bubbling is occurring in a pressure regulator The controller may automatically select a bubble CPAP mode if bubbling is occurring in the pressure regulator.

The respiratory therapy mode may comprise a bubble CPAP therapy mode or a high flow therapy mode.

In another aspect of the disclosure there is provided a controller for a breathing assistance apparatus for providing respiratory therapy, the controller configured to:

determine at least one waveform characteristic based on a waveform of a measured characteristic of bubbling in the pressure regulator, and based on the at least one waveform characteristic, estimate an estimated flow rate and/or pressure in a gases flow pathway.

It will be appreciated that the above aspect may be combined with any combination of the other aspects (and in particular the above aspects).

In another aspect of the disclosure there is provided a method for estimating a flow rate and/or a pressure in a gases flow path of a breathing assistance system, the method comprising:

determining at least one waveform characteristic based on a waveform of a measured characteristic of bubbling in a pressure regulator, and based on the at least one waveform characteristic, estimating an estimated flow rate and/or pressure in a gases flow pathway.

It will be appreciated that the above aspect may be combined with any combination of the other aspects (and in particular the above aspects).

In another aspect of the disclosure there is provided a breathing assistance apparatus for providing respiratory therapy, the breathing assistance apparatus comprising:

a flow generator, the flow generator configured to provide a flow of gases to an inspiratory conduit, wherein the gases flow pathway comprises at least the inspiratory conduit configured to be connected to a patient interface, and an expiratory conduit configured to be connected to a pressure regulator the pressure regulator comprising a chamber with a column of a liquid into which an end portion of the expiratory conduit is submerged, a controller, the controller configured to:

measure at least one characteristic of bubbling in the pressure regulator, determine at least one waveform characteristic based on a waveform of the measured characteristic of bubbling in the pressure regulator, and based on the at least one waveform characteristic, estimate an estimated flow rate and/or pressure in the gases flow pathway.

The at least one characteristic of bubbling in the pressure regulator may be based on one or more of:

a signal indicative of an image of the bubbler as an output of a visual sensor, a signal indicative of the surface of the water in the bubbler as an output of a water level sensor, a signal indicative of the sound generated by the bubbler as an output of a microphone, a signal indicative of the optical properties of the liquid in the bubbler as an output of an optical sensor, a signal indicative of a gas flow characteristic, as an output of a gas flow characteristic sensor.

The at least one characteristic of bubbling in the pressure regulator may be based on a signal indicative of a gases flow rate in the gases flow pathway as an output of a flow sensor, optionally the signal is based on a measured flow rate and/or a pressure of the gases in the gases flow pathway.

The at least one characteristic of bubbling in the pressure regulator may be based on a signal indicative of a gases pressure in the gases flow pathway as an output of a pressure sensor (optionally the signal is based on a measured pressure of the gases in the gases flow pathway).

The estimated flow rate in the gases flow pathway may be a flow rate of gases at an end of the expiratory conduit.

The pressure in the gases flow pathway may be a pressure at the patient interface.

The flow rate of gases at the end of the expiratory conduit may be at the pressure regulator.

The controller may be configured to generate one or more alarms based on the estimated flow rate of gases at an end of the expiratory conduit and/or the estimated pressure at a patient interface.

The controller may be configured to generate one or more alarms if the estimated flow rate of gases at an end of the expiratory conduit (and optionally at the pressure regulator) is above a threshold.

The controller may be configured to generate one or more alarms if the estimated pressure at the patient interface is above a threshold.

The one or more alarms may comprise one or more of:

an audio alarm, a visual alarm.

The apparatus may comprise a display, optionally the display comprises one or more of: a touchscreen and/or one or more mechanical input devices.

The apparatus may comprise at least one gases property sensor configured to measure a flow rate of the gases in a gases flow pathway and/or a pressure of the gases in a gases flow pathway.

The controller may be configured to estimate the pressure at the patient interface additionally based on a relationship between the flow rate of the gases in a gases flow pathway and a pressure of the gases in a gases flow pathway.

The controller may be configured to estimate a leak flow rate of the system, the leak flow rate based on the difference between the measured flow rate of the gases in a gases flow pathway and the estimated flow rate of gases through the pressure regulator.

The controller may be configured to generate an alarm when the estimated leak flow rate is above a leak threshold The controller may be configured to generate an alarm when the estimated leak flow rate increases by more than a leak increase threshold over a predetermined period of time.

The controller may be configured to estimate a set point of the pressure regulator based on the estimated flow rate of gases through the pressure regulator and the estimated pressure at a patient interface.

The controller may be configured to display the estimated pressure at the patient interface on at least one display.

The respiratory therapy mode may comprise a bubble CPAP therapy mode or a high flow therapy mode.

The estimated flow rate and/or pressure in the gases flow pathway (optionally, the flow rate of gases through the pressure regulator and/or a pressure at a patient interface)

may be based on a model, the model comprising one or more waveform characteristic factors associated with each waveform characteristic.

The model may be a regression model.

The one or more waveform characteristic factors may be determined experimentally.

The at least one waveform characteristic may comprise or be based on one or more of:

- an amplitude of the waveform,
- a distance between positive peaks of the waveform,
- a number of times the waveform crosses a threshold,
- a time between positive peaks of the waveform,
- a time between negative peaks of the waveform,
- an amplitude of positive peaks of the waveform,
- an amplitude of negative peaks of the waveform,
- a magnitude of the amplitude difference between consecutive positive and negative peaks of the waveform.

The at least one waveform characteristic may comprise at least one amplitude characteristic.

The amplitude characteristic may comprise one or more of:

- an average of the amplitude of the positive peaks of the waveform, optionally over a time window,
- a standard deviation of the amplitude of the positive peaks of the waveform, optionally over a time window,
- an average of the amplitude of the negative peaks of the waveform, optionally over a time window,
- a standard deviation of the amplitude of the negative peaks of the waveform, optionally over a time window,
- an average of the amplitude of the waveform, optionally over a time window,
- a standard deviation of the amplitude of the waveform, optionally over a time window.

The at least one waveform characteristic may comprise at least one peak distance characteristic.

The peak distance characteristic may comprise one or more of:

- an average distance between positive peaks of the waveform, optionally over a time window,
- a standard deviation of an average distance between positive peaks of the waveform, optionally over a time window,
- a standard deviation of the distance between positive peaks of the waveform optionally over a time window
- an average distance between negative peaks of the waveform, optionally over a time window,
- a standard deviation of the negative between positive peaks of the waveform optionally over a time window.

The at least one waveform characteristic may comprise at least one peak difference characteristic.

The peak difference characteristic may comprise one or more of:

- an average of the magnitude of the amplitude difference between consecutive positive and negative peaks of the waveform, optionally over a time window, a standard deviation of the magnitude of the amplitude difference between consecutive positive and negative peaks of the waveform, optionally over a time window.

The at least one waveform characteristic may comprise at least one crossing characteristic.

The crossing characteristic may comprise one or more of:

- a number of times the waveform crosses zero,
- a number of times the waveform crosses an average amplitude of the waveform.

The controller may be configured to apply a high pass and/or a low pass filter to the measurement of the characteristic of bubbling in the pressure regulator.

The waveform may be configured to be divided into one or more time windows, and optionally wherein the determination of the flow rate of gases through the pressure regulator and/or the pressure at a patient interface is made for each time window.

Each time window may be approximately two seconds.

Each time window may overlap with a preceding time window, and/or a subsequent time window.

The time window overlap may be approximately 1.5 seconds.

The determination of the flow rate of gases through the pressure regulator and/or the pressure at a patient interface may be based on a conduit characteristic of the inspiratory conduit and/or the expiratory conduit.

The conduit characteristic may comprise one or more of:

- conduit length,
- conduit diameter,
- a conduit type.

The determination of the flow rate of gases through the pressure regulator and/or the pressure at a patient interface may be based on a characteristic of the patient interface.

The breathing assistance apparatus may provide bubble CPAP therapy.

The breathing assistance apparatus may comprise a blower for generating the flow of gases.

The breathing assistance apparatus may comprise a humidifier for heating and/or humidifying the flow of gases.

The breathing assistance apparatus may comprise a housing for containing the blower and/or humidifier.

The breathing assistance apparatus may comprise a heated breathing tube.

The blower may be configured to deliver a substantially constant flow of gases and/or a substantially constant pressure.

At least one gases property sensor may be located at one or more of:

- in the breathing assistance apparatus, optionally within the flow generator,
- in a patient interface,
- in the pressure regulator,
- in the inspiratory conduit and/or expiratory conduit.

At least one gases property sensor may be located within the gases flow pathway.

The flow generator may be configured to provide a flow of gases to an inspiratory conduit at a target flow rate and/or a target pressure.

In another aspect of the disclosure there is provided a breathing assistance apparatus for providing respiratory therapy, the breathing assistance apparatus comprising:

- a flow generator, the flow generator configured to provide a flow of gases,
- a controller, the controller configured to:
  - measure at least one characteristic of bubbling in a pressure regulator,
  - determine at least one waveform characteristic based on a waveform of the measured characteristic of bubbling in the pressure regulator, and
  - based on the at least one waveform characteristic, estimate an estimated flow rate and/or pressure in a gases flow pathway.

It will be appreciated that the above aspect may be combined with any combination of the other aspects (and in particular the above aspects).

In an aspect of the disclosure there is provided a controller for a breathing assistance apparatus for providing respiratory therapy, the controller configured to:

determine at least one waveform characteristic based on a waveform of a measured characteristic of bubbling in the pressure regulator, and based on the at least one waveform characteristic, estimate an estimated flow rate and/or pressure in a gases flow pathway.

It will be appreciated that the above aspect may be combined with any combination of the other aspects (and in particular the above aspects).

In an aspect of the disclosure there is provided a method for estimating a flow rate and/or a pressure in a gases flow path of a breathing assistance system, the method comprising:

determining at least one waveform characteristic based on a waveform of a measured characteristic of bubbling in a pressure regulator, and based on the at least one waveform characteristic, estimating an estimated flow rate and/or pressure in a gases flow pathway.

It will be appreciated that the above aspect may be combined with any combination of the other aspects (and in particular the above aspects).

In another aspect of the disclosure there is provided a breathing assistance apparatus for providing respiratory therapy, the breathing assistance apparatus comprising:

a flow generator, the flow generator configured to provide a flow of gases to a patient at a target flow rate, at least one gases property sensor, the at least one gases property sensor configured to measure a flow rate and/or a pressure of the gases after the flow generator, wherein the patient interface is configured to be connected to a pressure regulator the pressure regulator comprising a chamber with a column of liquid (optionally water) into which an end portion of the expiratory conduit is submerged, a controller, the controller configured to:

determine a waveform based on the measurement of the flow rate and/or pressure of the gases, and determine at least one waveform characteristic based on the flow and/or pressure waveform, and based on the at least one waveform characteristic, determine whether bubbling is occurring in the pressure regulator.

In another aspect of the disclosure there is provided a breathing assistance apparatus for providing respiratory therapy, the breathing assistance apparatus comprising:

a flow generator, the flow generator configured to provide a flow of gases to a patient at least one gases property sensor, the at least one gases property sensor configured to measure a flow rate and/or a pressure of the flow of gases, a controller, the controller configured to:

determine a waveform based on the measurement of the flow rate and/or pressure of the gases in the gases flow path, and determine at least one waveform characteristic based on the flow and/or pressure waveform, and based on the at least one waveform characteristic, determine whether bubbling is occurring in a pressure regulator.

In another aspect of the disclosure there is provided a breathing assistance apparatus for providing respiratory therapy, the breathing assistance apparatus comprising:

a flow generator, the flow generator configured to provide a flow of gases to an inspiratory conduit, at least one gases property sensor, the at least one gases property sensor configured to measure a flow rate and/or a pressure of the gases in a gases flow pathway, wherein the gases flow pathway comprises at least the inspiratory conduit configured to be connected to a patient interface, and an expiratory conduit configured to be connected to a pressure regulator the pressure regulator comprising a chamber with a column of water into which an end portion of the expiratory conduit is submerged, a controller, the controller configured to:

determine a waveform based on the measurement of the flow rate and/or pressure of the gases in the gases flow path, and determine at least one waveform characteristic based on the flow and/or pressure waveform, and based on the at least one waveform characteristic, determine one or more flow and/or pressure oscillation occurring in the pressure regulator.

In another aspect of the disclosure there is provided a breathing assistance apparatus for providing respiratory therapy, the breathing assistance apparatus comprises:

a flow generator, the flow generator configured to provide a flow of gases to an inspiratory conduit at a target flow rate, at least one gases property sensor, the at least one gases property sensor configured to measure a flow rate and/or a pressure of the gases in a gases flow pathway, wherein the gases flow pathway comprises at least the inspiratory conduit configured to be connected to a patient interface, and an expiratory conduit configured to be connected to a pressure regulator the pressure regulator comprising a chamber with a column of water into which an end portion of the expiratory conduit is submerged, a controller, the controller configured to:

determine a waveform based on the measurement of the flow rate and/or pressure of the gases in the gases flow path, and determine at least one waveform characteristic based on the flow and/or pressure waveform, and based on the at least one waveform characteristic, determine whether bubbling is occurring in the pressure regulator.

It will be appreciated that the above four aspect may be combined with any combination of the other aspects (and in particular the below aspects).

The determination of whether bubbling is occurring may be based on determining pressure and/or flow oscillations in the waveform indicative of bubbling in the pressure regulator.

The controller may be configured to display whether bubbling is occurring in the pressure regulator on a display.

The controller may be configured to generate an alarm if it is determined bubbling is not occurring in the pressure regulator.

The alarm may comprise one or more of:

an audio alarm a visual alarm.

The controller may automatically select a respiratory therapy mode based on whether bubbling is occurring in the pressure regulator.

The respiratory therapy mode may comprise a bubble CPAP therapy mode or a high flow therapy mode.

The determination of whether bubbling is occurring may be based on at least one waveform characteristic exceeding an associated threshold.

The determination of whether bubbling is occurring may be based on a model, the model comprising one or more waveform characteristic factors associated with each waveform characteristic.

The model may be a regression model.

The one or more waveform characteristic factors may be determined experimentally.

The at least one waveform characteristic may comprise or be based on one or more of:

an amplitude of the waveform, a distance between positive peaks of the waveform, an magnitude of the amplitude difference between consecutive positive and negative peaks of the waveform.

The at least one waveform characteristic may comprise at least one amplitude characteristic, and wherein the amplitude characteristic comprises one or more of:

an average of the amplitude of the positive peaks of the waveform, optionally over a time window, a standard deviation of the amplitude of the positive peaks of the waveform, optionally over a time window, The at least one waveform characteristic may comprise at least one peak distance characteristic, and wherein the peak distance characteristic comprises one or more of:

an average distance between positive peaks of the waveform, optionally over a time window, a standard deviation of the distance between positive peaks of the waveform optionally over a time window.

The at least one waveform characteristic may comprise at least one peak difference characteristic, and wherein the peak difference characteristic comprises one or more of:

an average of the magnitude of the amplitude difference between consecutive positive and negative peaks of the waveform, optionally over a time window, a standard deviation of the magnitude of the amplitude difference between consecutive positive and negative peaks of the waveform, optionally over a time window.

The controller may be configured to apply a high pass and/or a low pass filter to the measurement of the flow rate or pressure and/or the waveform.

The waveform may be configured to be divided into a one or more time windows, and optionally wherein the determination of whether bubbling is occurring is made for each time window.

Each time window may be approximately two seconds.

Each time window may overlap with a preceding time window, and/or a subsequent time window.

The time window overlap may be approximately 1.5 seconds.

The determination of whether bubbling is occurring may be a probability of bubbling occurring between 0 and 1.

Bubbling may be determined to be occurring when the probability of bubbling occurring is greater than 0.5.

The determination of whether bubbling is occurring may be based on an ambient pressure.

The determination bubbling is occurring may be based on an ambient temperature

The determination bubbling is occurring may be based on an altitude of the apparatus.

The determination bubbling is occurring may be based on a water level in a humidifier located in the gases pathway.

The apparatus may be configured to provide a combination of ambient air, and a supplementary gas, and the determination of whether bubbling is occurring is based on the ratio of ambient air to supplementary gas.

The determination of whether bubbling is occurring may be based on a conduit characteristic of the inspiratory conduit and/or the expiratory conduit.

The conduit characteristic may comprise one or more of:

conduit length, conduit diameter, a conduit type.

The determination of whether bubbling is occurring may be based on a characteristic of the patient interface.

The controller may be configured to monitor a pressure of the gases in the gases flow pathway.

The controller may be configured to generate an alarm when the pressure of the gases flow exceeds a threshold.

The breathing assistance apparatus may provide CPAP therapy.

The breathing assistance apparatus may provide bubble CPAP therapy.

The breathing assistance apparatus may comprise a blower for generating the flow of gases.

The breathing assistance apparatus may comprise a humidifier for heating and/or humidifying the flow of gases.

The breathing assistance apparatus may comprise a housing for containing the blower and/or humidifier.

The breathing assistance apparatus may comprise a heated breathing tube.

The blower may be configured to deliver a substantially constant flow of gases and/or a substantially constant pressure.

The at least one gases property sensor may be located at one or more of:

in the breathing assistance apparatus, optionally within the flow generator, in a patient interface, in the pressure regulator, in the inspiratory conduit and/or expiratory conduit.

In another aspect of the disclosure there is provided a breathing assistance apparatus for providing respiratory therapy, the breathing assistance apparatus comprises:

a flow generator, the flow generator configured to provide a flow of gases to an inspiratory conduit, at least one gases property sensor, the at least one gases property sensor configured to measure a flow rate and/or a pressure of the gases in a gases flow pathway, a controller, the controller configured to:

determine a waveform based on the measurement of the flow rate and/or pressure of the gases in the gases flow path, and determine at least one waveform characteristic based on the flow and/or pressure waveform, and based on the at least one waveform characteristic, determine whether bubbling is occurring in a pressure regulator, wherein the controller automatically selects a respiratory therapy mode based on whether bubbling is occurring in the pressure regulator.

The controller may automatically selects a bubble CPAP mode if bubbling is occurring in the pressure regulator.

The respiratory therapy mode may comprise a bubble CPAP therapy mode or a high flow therapy mode.

A breathing assistance system may comprises the breathing assistance apparatus, and/or the controller of any of the paragraphs above.

In some embodiments, breathing assistance apparatus includes any combination of the features disclosed in relation to other aspects.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Figure 1:
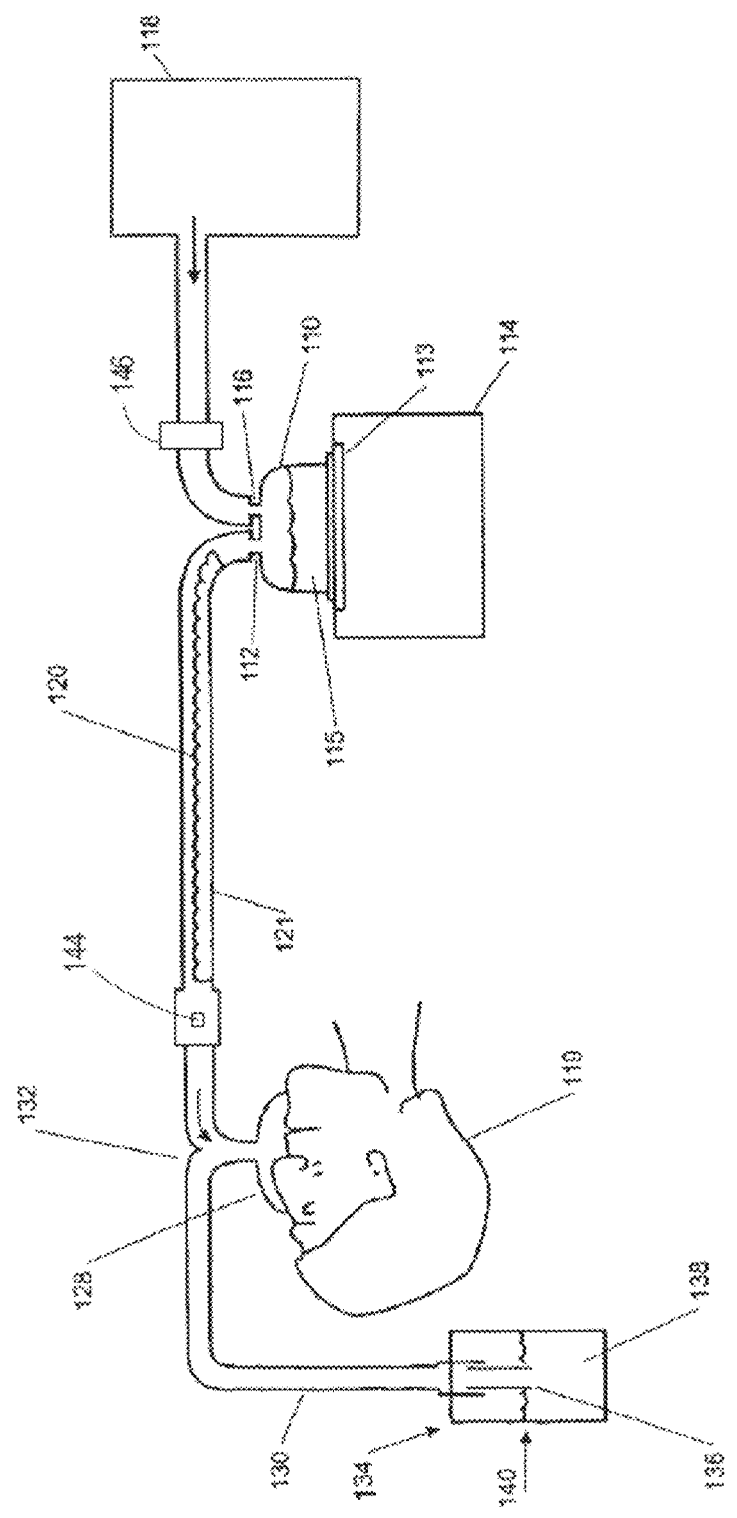
FIG. 1 illustrates schematically a conventional setup of using a wall source to provide bubble CPAP.

Bubble Continuous Positive Airway Pressure (Bubble CPAP) is a form of respiratory therapy (for example providing respiratory support) in which a patient (typically an infant) is supplied with a flow of gas via a patient interface. The flow of gas is typically provided by a gas source in the wall of a hospital or clinic, or may be provided by cylinders of compressed air and/or oxygen, for example during transport.

Bubble CPAP can be provided while the patient is in an incubator to provide respiratory support to the patient (e.g. an infant).

The patient interface is connected to two conduits, which are an inspiratory conduit and an expiratory conduit. The inspiratory conduit provides gas to the patient. The expiratory conduit provides a passage for exhaled gases from the patient. The expiratory conduit is in communication with a pressure regulator, which is used to set pressure.

The pressure regulator may be a chamber with a column of liquid (for example water but it will be appreciated that other liquids may be used) into which an end portion of the expiratory conduit is submerged. The gases in the expiratory conduit are discharged into the pressure regulator. The gases in the expiratory conduit (for example including the exhaled gases) being discharged into the water may result in bubbling of the water i.e. a bubbling effect. The bubbling is caused by the flow of gases discharged into the pressure regulator exceeding a pressure set point. The pressure is based on a level to which the end of the expiratory conduit is submerged within the water column. A user may control this pressure by varying the level to which the level to which the end of the expiratory conduit is submerged within the water column. If the flow of gases discharged into the pressure regulator does not exceed the pressure set point then no bubbling will occur. Indication of whether bubbling is occurring or not may be important to a user in determining whether therapy is being provided. For example, if the pressure set point is too high then adequate therapy may not be provided and bubbling may not be occurring or may be intermittent.

The patient interface is typically configured to form a seal with the patient's mouth and/or nose. Examples of sealed patient interfaces can include a nasal mask, an oral mask, a full face mask (which covers and seals the nose and mouth), nasal pillows, or a cannula with sealing nasal prongs.

In some locations, such as in certain developing countries or in a remote area, a wall source may not be available or may be limited in availability. The present disclosure provides systems and methods of providing bubble CPAP therapy with a flow generator alternative to and/or optionally in addition to a wall source. The flow generator can also include an integrated humidifier to heat and humidify the flow of gas. An example of a flow generator with an integrated humidifier is a breathing assistance apparatus which provides high flow therapy. A heated breathing tube can also be used with the respiratory apparatus to deliver the flow of gas from the humidifier to the patient interface. The flow generator can also include an integrated blender to provide supplementary gases to the gases flow. The flow generator is preferably a flow generator that draws in ambient gases e.g. ambient air rather than be connected to a gases source e.g. a gas tank or a wall source. The blender allows a supplementary gas or gases to be mixed with the drawn in ambient gases.

More details of a respiratory device are described in PCT application PCT/IB2020/052566, the entirety of which is incorporated by reference herein.

The respiratory apparatus (for example a high flow respiratory apparatus) can provide various modes of therapy, including but not limited to high flow therapy i.e. high flow respiratory support (such as a nasal high flow therapy, or tracheal high flow therapy), CPAP, bi-level, and bubble CPAP, so that the patient need not switch to a different breathing assistance apparatus when switching to a different mode of respiratory therapy (for example, when the patient's condition changes). Each therapy may have a corresponding apparatus mode.

When the apparatus is operating in each apparatus mode, the apparatus may be used with one or more component particular to the mode and/or therapy type being provided. For example, in a bubble CPAP mode the apparatus may be used with a sealing interface, a pressure regulator and expiratory and/or inspiratory conduit.

The respiratory apparatus is capable of operating in a bubble CPAP therapy mode, or a nasal high flow therapy mode (as described in more detail below). Additionally, or alternatively the respiratory apparatus may also be capable of operating in other high flow therapy modes e.g. tracheal high flow or other high flow. Nasal high flow is delivered through a nasal interface. Tracheal high flow can be delivered by a tracheal interface. Other interfaces may also be possible e.g. an oral interface to provide high flow to the airways via the oral passage. The described breathing assistance apparatus can operate in at least high flow therapy mode and bubble CPAP mode.

The respiratory apparatus device operates as a flow controlled device, as described in more detail below (for example the respiratory apparatus may control motor of the blower to achieve a target flow). The respiratory apparatus may control the apparatus to achieve the target flow rate based on an output from one or more sensors, for example a flow rate sensor, of the device (as described in more detail elsewhere in the specification). The target flow may be a constant flow rate. The target flow may be set by a user, or be based on the device being in a mode of therapy, such as bubble CPAP therapy mode or a nasal high flow therapy mode. In one example the controller may include predefined target flow rates for bubble CPAP therapy mode and nasal high flow therapy mode. The predefined target flow rates may be stored within a memory of the controller.

When operating in the bubble CPAP mode, the breathing assistance apparatus can detect pressure and/or flow oscillations indicative of bubbling in the pressure regulator (such as a bubbler) via a detection algorithm. The breathing assistance apparatus can generate one or more notifications based on the detection of pressure and/or flow oscillations indicative of bubbling. For example, the breathing assistance apparatus may generate an alarm if no bubbling is detected in the pressure regulator or if bubbling is irregular (for example, intermittent bubbling). Bubbling may be intermittent where bubbling transitions between occurring and not occurring (for example as described in more detail below).

The apparatus can provide a plurality of alarms and monitoring. For example, the apparatus can determine if there is an irregular amount of leak, an occlusion, a suggested and/or automatic flow rate change, and/or the flow rate not meeting an inspiratory demand (for example optionally if the pressure exceeds a threshold.)

The term breathing assistance apparatus, respiratory device, respiratory apparatus, respiratory support apparatus, respiratory support device breathing apparatus, and variations thereof can be interchangeably used to described and define the same item.

The breathing assistance apparatus, respiratory device, respiratory apparatus, and breathing apparatus may be part of a breathing assistance system (or a respiratory system) comprising one or more additional components as described in more detail below (for example an inspiratory tube, an expiratory tube, a pressure generator).

The term tube and conduit can be interchangeably used to described and define the same item.

High flow therapy as discussed herein is intended to be given its typical ordinary meaning as understood by a person of skill in the art which generally refers to a respiratory assistance system delivering a targeted flow of humidified respiratory gases via an intentionally unsealed patient interface with flow rates generally intended to meet or exceed inspiratory flow of a patient. Typical patient interfaces include, but are not limited to, a nasal or tracheal patient interface. Typical flow rates for adults often range from, but are not limited to, about fifteen liters per minute to about sixty liters per minute or greater. Typical flow rates for pediatric patients (such as neonates, infants and children) often range from, but are not limited to, about one liter per minute per kilogram of patient weight to about three liters per minute per kilogram of patient weight or greater. High flow therapy can also optionally include gas mixture compositions including supplemental oxygen and/or administration of therapeutic medicaments. High flow therapy is often referred to as nasal high flow (NHF), humidified high flow nasal cannula (HHFNC), high flow nasal oxygen (HFNO), high flow therapy (HFT), or tracheal high flow (THF), among other common names.

Some example flow rates used to achieve "high flow" may be any of the flow rates listed below. For example, in some configurations, for an adult patient 'high flow therapy' may refer to the delivery of gas(es) to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For example for a neonatal, infant, or child patient 'high flow therapy' may refer to the delivery of gas(es) to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may deliver gas(es) to the patient at a flow rate of between about 1 LPM and about 100 LPM, or at a flow rate in any of the sub-ranges outlined above.

The high flow rate gases delivered are humidified (as described in more detail below). Humidifying the gases improves comfort and improves tolerance to therapy. This may of particular importance when providing therapy to infants who cannot communicate.

In some embodiments, the flow rate delivered during a bubble CPAP mode may be less than about 20 LPM, or less than about 15 LPM, or about 15 LPM.

Although certain examples are described below, those of skill in the art will appreciate that the disclosure extends beyond the specifically disclosed examples and/or uses and obvious modifications and equivalents thereof. Thus, it is intended that the scope of the disclosure herein disclosed should not be limited by any particular examples described below.

Bubble CPAP therapy can produce variations or oscillations in the pressure of gases supplied to a patient. By submerging one end of the expiratory conduit into a liquid (for example water, or a saline solution) column, the resulting bubbles generate a variation or ripple in the pressure of gases delivered to the patient (for example as bubbling occurs as described in more detail above). The bubble CPAP system also provides a method of varying a mean pressure of gases supplied to the patient by variation of the level to which the end of the expiratory conduit is submerged within the water column. The level of submergence of the end of the expiratory conduit can be kept constant in order to maintain the mean pressure of gases supplied to the patient.

It will be appreciated that the liquid may be any of, or a combination of water, saline solution and/or any other liquid.

As shown in FIG. 1, a conventional breathing assistance system for providing bubble CPAP therapy can provide to a patient 119 humidified and pressurized gas through a patient interface, such as a mask 128 in FIG. 1 connected to an inspiratory conduit 121. The inspiratory conduit 121 is connected to the outlet 112 of a humidification chamber 110, which contains a volume of water 115. As the volume of water 115 within the humidification chamber 110 is heated by a heater plate 113 in the device housing 114, water vapor begins to fill the volume of the chamber 110 above the water's surface. The water vapor can heat and humidify a flow of gas (for example, air) provided from a wall source 118 (see FIG. 1) into the chamber 110 through an inlet 116 of the chamber 110. The heated and humidified gas is passed out of an outlet 112 of the humidification chamber 110 into the inspiratory conduit 121. The inspiratory conduit 121 may contain a heater, such as heater wires 120 in FIG. 1, which heat the walls of the conduit to promote a substantially constant humidity profile along the inspiratory conduit 121 and therefore reduce condensation of the humidified gas within the inspiratory conduit 121. The device can supply power to heat the inspiratory conduit 121 and the heater plate 113, such as through input from one or more sensors (for example a gases property sensor) in the system, as will be described in further detail below.

The inspiratory conduit 121 may be formed by at least one conduit (for example connected together).

The humidified gas can pass through the inspiratory conduit 121 to a patient interface, such as the mask 128, attached and/or sealed around the patient's 119 mouth, nose, and/or nares. The inspiratory conduit 121 provides the patient 119 with a flow of gas that may by ambient air, oxygen, a mixture of the two, or a mixture of ambient air and other auxiliary gas(es). The gas may include medicaments, which may be added through nebulization. The gas may include supplemental gases for example Nitric oxide. The supplemental gases may be provided via a supplemental gases port. The apparatus may include one or more supplemental gases composition sensor (for example as an ultrasonic sensor as described below) to measure an amount of supplemental gases in the flow of gases (or for example as a ratio of supplemental gases in the flow of gases to other gases). The flow of gas through the inspiratory conduit 121 can be delivered at a substantially constant flow rate and/or a substantially constant pressure in a bubble CPAP. As shown in FIG. 1, a setup has a flow of gas supplied by the wall source 118. The wall source 118 can deliver the gas at the target flow rate so as to maintain the flow rate of gas delivered to the patient.

In some configurations, the supplemental gas may be provided in combination with, or separate to oxygen (as described in relation to FIG. 4A below).

As shown in FIG. 1, excess gas can flow through the expiratory conduit 130 to a pressure regulator 134, which is a bubbler in the illustrated example. In a bubble CPAP system, the expiratory conduit 130 can terminate in an open terminal end 136. This terminal end 136 can be submerged in a volume of water 138 inside the bubbler 134.

The expiratory conduit 130 may be formed at least in part from a breathable material e.g. Evaqua material in order to allow excess water vapour to travel to the ambient atmosphere. The breathable expiratory conduit 130 allows excess water vapour to travel to the ambient atmosphere to reduce condensate formation in the expiratory conduit 130 that could block the expiratory conduit 130. An expiratory conduit 130 blocked by condensate will not provide the set pressure based on the level the exp limb is submerged. It will be appreciated The expiratory conduit 130 may be formed by at least one conduit (for example connected together).

The bubbler can regulate pressure by the terminal end 136 of the expiratory conduit 130 submerged at a desired depth under the water level 140 within the volume of water 138. The terminal end 136 can also optionally be located on a short conduit that can be integrated into the end of the expiratory conduit 130. The bubbler can act as a pressure regulator by venting out gas whenever the pressure exceeds the desired level so as to maintain the average or mean pressure at the target level. The bubble CPAP system can also include a pressure relief valve 146 for venting excess gas when the pressure exceeds the desired level. The bubbler can also provide oscillations in the pressure, which may have clinical benefits. Bubble CPAP therapy may lower the incidence of acute lung injury and bronchopulmonary dysplasia, compared with intubation and/or mechanical ventilation. Bubble CPAP therapy may also help with carbon dioxide clearance. Bubble CPAP therapy may also be simple for a clinician to set up as it only requires the user to insert the terminal end 136 of the expiratory conduit 130 submerged at a desired depth under the water level 140 to set a pressure and to cause oscillations during breathing that may aid in keeping alveoli open and providing improved lung function for infants.

Figure 2:
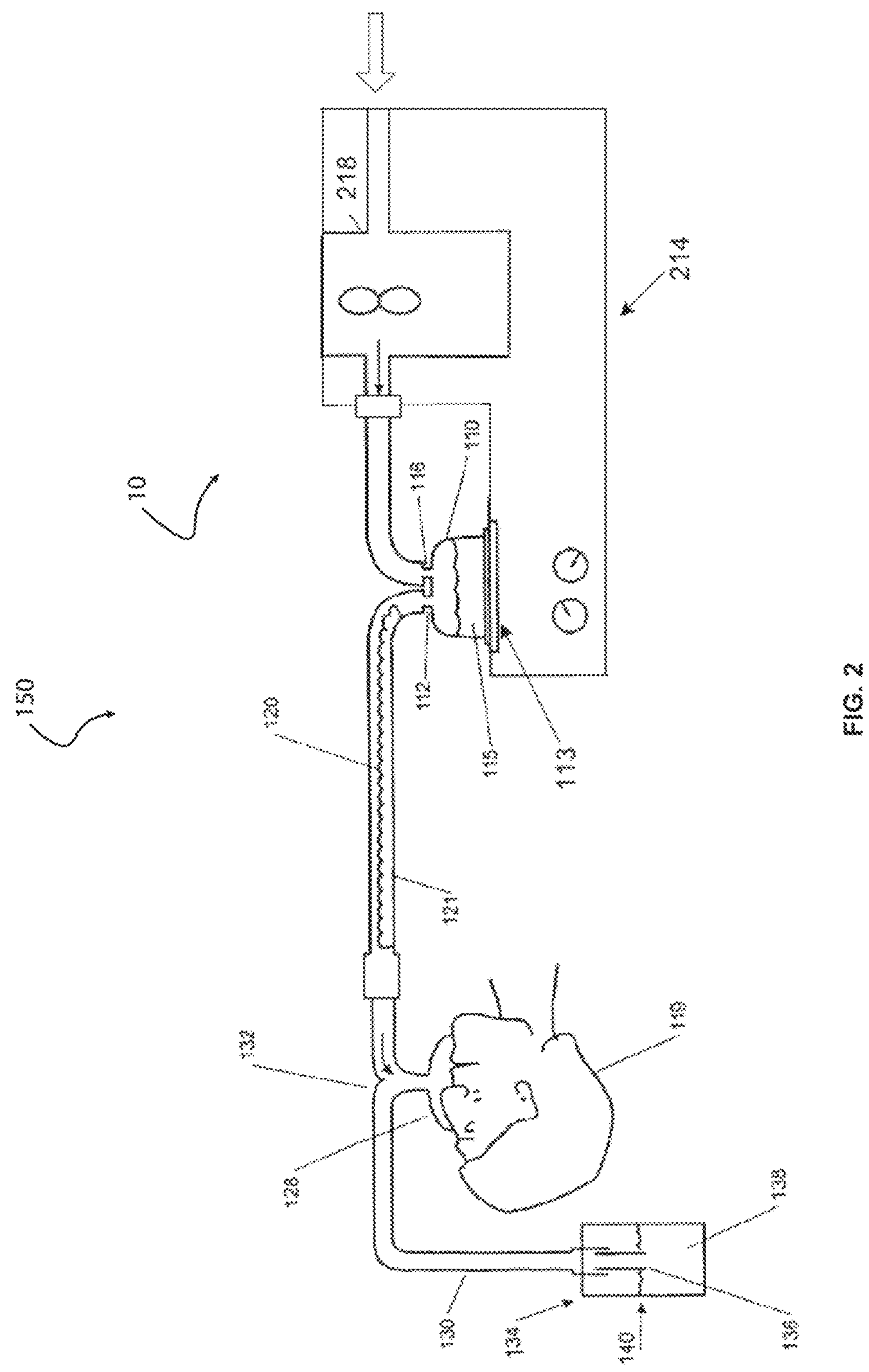
FIG. 2 illustrates schematically a breathing assistance apparatus with a flow generator to provide bubble CPAP.

FIG. 2 illustrates an example breathing assistance system 150 with a breathing assistance apparatus 10. The breathing assistance apparatus comprises a flow generator 218 (the flow generator 218 may include a blower but can include other types of flow generator disclosed herein) configured to provide bubble CPAP. Using a flow generator to generate the flow of gas can allow the breathing assistance apparatus 10 to be used without a wall source to provide bubble CPAP, such as in circumstances where a wall source is not available. Further, using a flow generator in a breathing assistance apparatus 10 allows the apparatus to draw in ambient air and provide ambient air as a flow of gases for bubble CPAP. This allows the breathing assistance apparatus 10 to be simpler and cheaper to use as there is no requirement for a gas store or a gas source e.g. a wall source. Further the breathing assistance apparatus 10 with a flow generator is advantageous because there is no risk of running out of gases, since ambient air is provided to the patient. This ensures there is no disruption in therapy due to a gas source being empty, since ambient air is abundant. By integrating the humidifier, and optionally a supplementary gases blender (for example, by integrating an oxygen inlet port 358' shown in FIG. 3C), into the flow generator, fewer separate components are needed in the system, which simplifies its setup. Further the system occupies less space because there are less separate components connected by tubes. The described breathing assistance apparatus 10 with an integrated humidifier and optionally an integrated supplementary gas blender can occupy less space and reduces additional interconnecting tubes. Additionally, the flow generator, integrated humidifier, and supplementary gases blender can be controlled by a single controller, which allows for additional monitoring and control of various flow parameters, as will be described further.

In some embodiments, the breathing assistance apparatus 10 including a flow generator may be able to provide other forms of therapy, such as a nasal high flow therapy, thereby making for an easier transition between different types of respiratory support as the patient's condition changes, and may also reduce the number of consumable components required, for example a common heated breathing tube may be used across multiple therapies, requiring only the patient interface to be changed.

In some embodiments, the breathing assistance apparatus 10 may comprise a sufficiently small dimension suitable for use on a bed.

The breathing assistance system 150 in FIG. 2 can differ from the conventional bubble CPAP setup in FIG. 1 at least by having the flow of gas provided by the flow generator 218 integrated within the device housing 214. The system in FIG. 2 can also optionally include a supplementary gas source (such as an oxygen tank, an oxygen blender coupled to a flowmeter, and the like) for controlling oxygen concentration in the flow of gas delivered to the patient 119. The supplemental gas source can be connected to the device housing 214 and/or to the flow generator 218 (for example at a supplementary gas inlet). The supplementary gas source can also be configured to provide other types of auxiliary gas, such as nitrogen. The supplementary gas source may be connected to an internal blender that blend ambient air and the supplementary gases to provide a gases flow to a patient. The concentration of the supplementary gases introduced into, or present in, the gases stream can be controlled.

The breathing assistance system or apparatus may comprise one or more gases property sensors to measure a property of the gas (for example as a sensor which measures a characteristic of bubbling). For example, the system or apparatus may comprise one or more sensor to determine a property of the gases. The gases property sensors may comprise one or more of: a pressure sensor, a flow sensor, a temperature sensor.

It will be appreciated that the disclosure below, that the gases property sensor is being used as an example, and that the disclosure may equally apply to another sensor which measures a characteristic of bubbling.

The gases property sensor may be located in the apparatus (or flow generator 218) as described in more detail below.

The gases property sensor may be located in a gases flow path after a flow generator.

The gases property sensor (or other s may be located in a patient interface.

The gases property sensor may be located in the pressure regulator.

The gases property sensor may be located in the gases flow pathway (for example the inspiratory conduit and/or expiratory conduit or other gases flow pathway in the apparatus.)

In some embodiments, the gases property sensor may be provided through a monitoring port in a patient interface, pressure regulator or other component in the gases flow pathway.

The sensor may be provided with a lead to connect to the apparatus or may communicate with the apparatus wirelessly.

The sensor may be connected to the apparatus via one or more wires embedded within a wall of a conduit, or provided within or external to the conduit.

For example, as shown in FIG. 1 the system can include a temperature sensor, such as the temperature sensor 144, in the inspiratory conduit 121. The temperature sensor 144 can be coupled to and in electrical communication with a controller located in the device housing 214.

In some embodiments the flow generator is configured to receive the ambient gases and supplementary gases and mix these together.

The breathing assistance system 150 in FIG. 2 can include a high flow apparatus (for example as the breathing assistance apparatus 10).

Figure 3A:
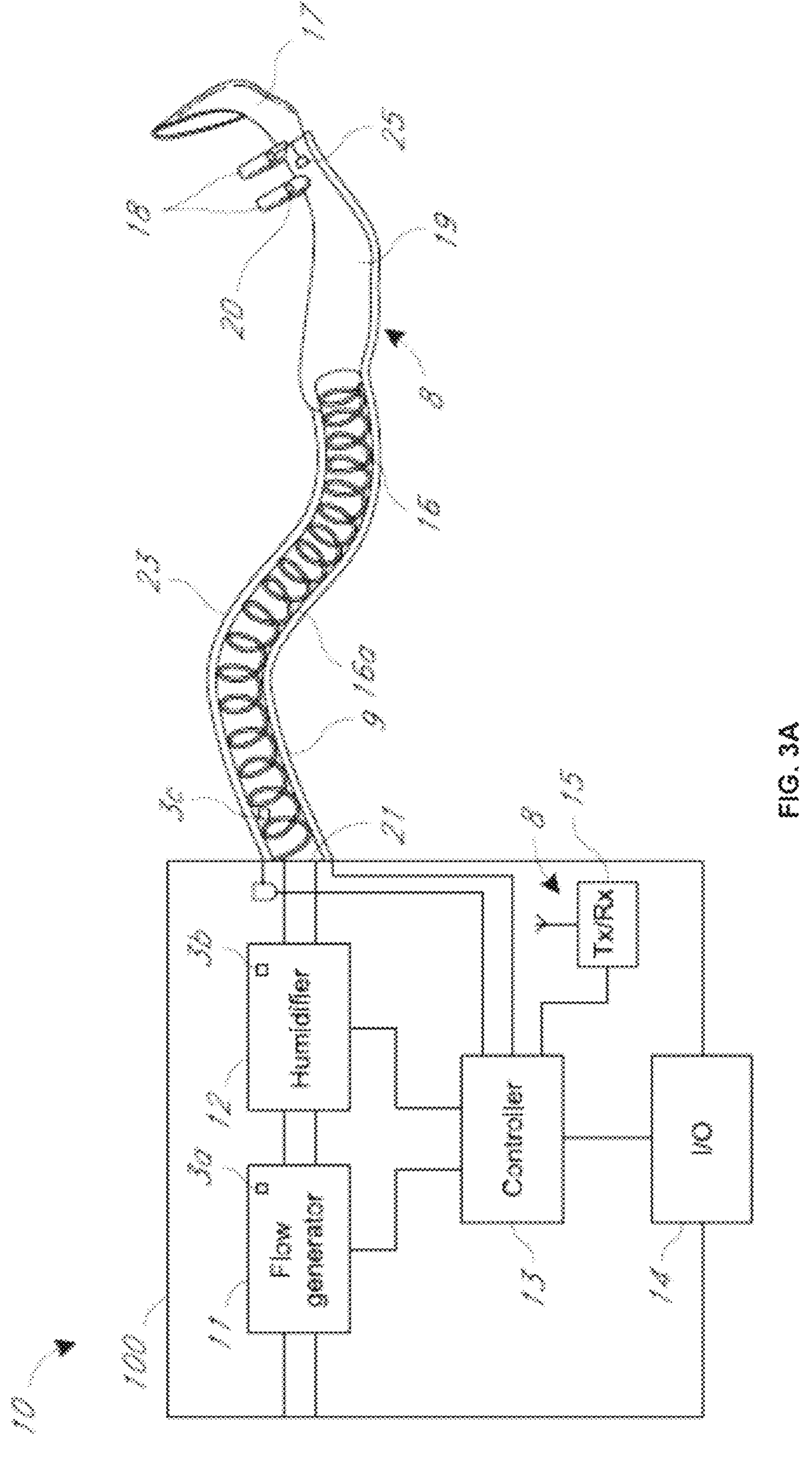
FIG. 3A illustrates schematically a breathing assistance system configured to provide a respiratory therapy to a patient.

FIG. 3A illustrates an example of a breathing assistance apparatus 10 in a high flow therapy configuration. However, it will be appreciated that features of the breathing assistance apparatus 10 as used in a high flow therapy configuration may be used in the apparatus when in a bubble CPAP configuration (for example as shown in FIG. 2).

The breathing assistance apparatus 10 can include a main device housing 100. The main device housing 100 can contain a flow generator 11 that can be in the form of a motor/impeller arrangement (such as a blower), an optional humidifier or humidification chamber 12, a controller 13, and a user interface 14. The humidification chamber 12 may be removable for refilling and/or replacement. The user interface 14 can include a display and input device(s) such as button(s), a touch screen, a combination of a touch screen and button(s), or the like. The controller 13 can include one or more hardware and/or software processors and can be configured or programmed to control the components of the apparatus, including but not limited to operating the flow generator 11 to create a flow of gas for delivery to a patient, operating the humidifier 12 (if present) to humidify and/or heat the gas flow, receiving user input from the user interface 14 for reconfiguration and/or user-defined operation of the breathing assistance apparatus 10, and outputting information (for example on the display) to the user. The user can be a patient, healthcare professional, or others.

With continued reference to FIG. 3A, which discloses a breathing assistance apparatus in a high flow therapy configuration, a patient breathing conduit 16 can be coupled to a gases flow outlet 21 in the main device housing 100 of the breathing assistance apparatus 10, and be coupled to a patient interface 17. In the example of a high flow apparatus as illustrated by FIG. 3A, the patient interface is a non-sealing interface comprising a nasal cannula with a manifold 19 and nasal prongs 18 for providing a nasal high flow therapy. The nasal cannula does not completely seal with the nostrils of the user such that exhaled gases leak out from around the nasal prongs when the user exhales. The patient breathing conduit 16 can also be coupled to a sealing interface like a face mask, an oro-nasal mask, a nasal mask, a nasal pillow mask, or a nasal cannula for providing bubble CPAP.

The flow of gas can be generated by the flow generator 11, and may be humidified, before being delivered to the patient via the patient conduit 16 through the patient interface 17. The controller 13 can control the flow generator 11 to generate a gas flow of a desired flow rate, and/or one or more valves to control mixing of air and oxygen or other breathable gas. The controller 13 can control a heating element in the humidification chamber 12, if present, to heat the gases to a desired temperature that achieves a desired level of temperature and/or humidity for delivery to the patient. The patient conduit 16 can have a heating element 16*a*, such as a heater wire, to heat gases flow passing through to the patient. The heating element 16*a* can also be under the control of the controller 13. The heating element 16*a* heats gases to reduce and/or prevent condensation within the patient conduit 16.

The breathing assistance apparatus 10 may comprise one or more gases property sensors to measure a property of the gas. The gases property sensor may comprise one or more of an ultrasonic transducer(s), flow sensor(s) such as a thermistor flow sensor, pressure sensor(s), temperature sensor(s), humidity sensor(s), or other sensors, in communication with the controller 13, to monitor characteristics of the gas flow and/or operate the breathing assistance apparatus 10 in a manner that provides suitable therapy. The gas flow characteristics can include gases concentration, flow rate, pressure, temperature, humidity, or others. The sensors 3*a*, 3*b*, 3*c*, 20, 25, such as pressure, temperature, humidity, and/or flow sensors, can be placed in various locations in the main device housing 100, the patient conduit 16, and/or the patient interface 17. The controller 13 can receive output from the sensors to assist it in operating the respiratory system 10 in a manner that provides suitable therapy, such as to determine a suitable target temperature, flow rate, and/or pressure of the gases flow. Providing suitable therapy can include meeting a patient's inspiratory demand, and/or meeting a patient's fraction of inspired oxygen ($FiO_2$) demand (for example to control a patient's oxygen saturation ($SpO_2$)). The suitable therapy flow rates, such as a high flow therapy flow rate, and/or a flow rate meeting or exceeding the patient's inspiratory demand, are explained below.

The breathing assistance apparatus 10 may comprise one or more patient sensors. The patient sensors may measure one or more patient characteristics (for example a patient's oxygen saturation). The one or more patient sensors may be connected to the controller by a wired connection or a wireless connection (as described in more detail below.)

In some configurations, the one or more patient sensors comprises a pulse oximeter configured to measure patient's blood oxygen saturation. The pulse oximeter may be for example finger mounted or ear mounted.

In some configurations, the apparatus may control an oxygen concentration or other supplemental gas concentration (as for example described above) provided to the patient. The apparatus may control one or more valves (as described below) based on a gas composition sensor (for example an ultrasonic sensor) and/or a patient's blood oxygen saturation (for example a pulse oximeter.) The apparatus may control the valve to reach a gas composition target (for example oxygen concentration), or a patient's blood oxygen saturation target.

Using an ultrasonic gas composition sensor (as described in more detail below) may allow for fast measurement of gases composition and a fast response in controlling the valve of the apparatus to control a gas composition target (for example oxygen concentration), or a patient's blood oxygen saturation target. It will be appreciated that alternatively, other gas composition sensors could be used.

The breathing assistance apparatus 10 can include a wireless data transmitter and/or receiver, or a transceiver 15 to enable the controller 13 to receive data signals 8 in a wireless manner from the operation sensors (for example gases property sensors, or patient sensors) and/or to control the various components of the system 10. Additionally, or alternatively, the data transmitter and/or receiver 15 can deliver data to a remote server or enable remote control of the system 10. In one example the remote server can record patient usage data e.g. usage of the bubble CPAP system or usage of the high flow system (for example as described in more detail below). Usage can be usage time and/or also include flow rate and humidity level (e.g. dew point). The system 10 can also include a wired connection, for example, using cables or wires, to enable the controller 13 to receive data signals 8 from the operation sensors and/or to control the various components of the breathing assistance system 10.

The wireless data transmitter and/or receiver, or a transceiver 15 may act as a network interface (for example as a modem).

The wireless data transmitter and/or receiver, or a transceiver 15 may use one or more communication protocols known in the art, for example Wifi, Bluetooth, Zigbee, cellular (3G, 4G, or 5G etc).

The wireless data transmitter and/or receiver, or a transceiver 15 may allow for communication between the apparatus and a mobile device (for example a phone or a tablet via Bluetooth or Wifi).

The wireless data transmitter and/or receiver, or a transceiver 15 may comprise a number of separate transmitters, receivers and/or transceiver for each, or for a group of communication protocol(s).

The wireless data transmitter and/or receiver, or a transceiver 15 may be configured to transmit data and receive data from one or more devices (for example a server).

One or more events, or alarms (as described in more detail below) may be transmitted to one or more servers and/or devices (for example a computer, phone or tablet). Additional information (for example the time, duration, or severity) associated with the event or alarm may be additionally transmitted to the server and/or device.

A bubbling time metric based on whether bubbling is occurring (as described in more detail below) may also be transmitted to the server and/or device.

The breathing assistance apparatus 10 can be powered from mains voltage.

In some embodiments, the system can include an auxiliary power source (for example a battery).

In some embodiments, the system can include a battery. The battery may provide the main source of power for the system, or may serve as an auxiliary source of power when the main source of power is unavailable. This is advantageous because therapy can be continued to be delivered i.e. gases can continue to be delivered to a patient even if there is a shortage or outage in mains power. This is advantageous because therapy can be maintained for a period of time for neonatal or infants thereby reducing the chances or physiological deterioration or harm occurring to these patient's due to loss of therapy.

The battery can increase portability of the system to allow for the system to be used in situations where a mains voltage power source is unavailable.

Figure 3B:
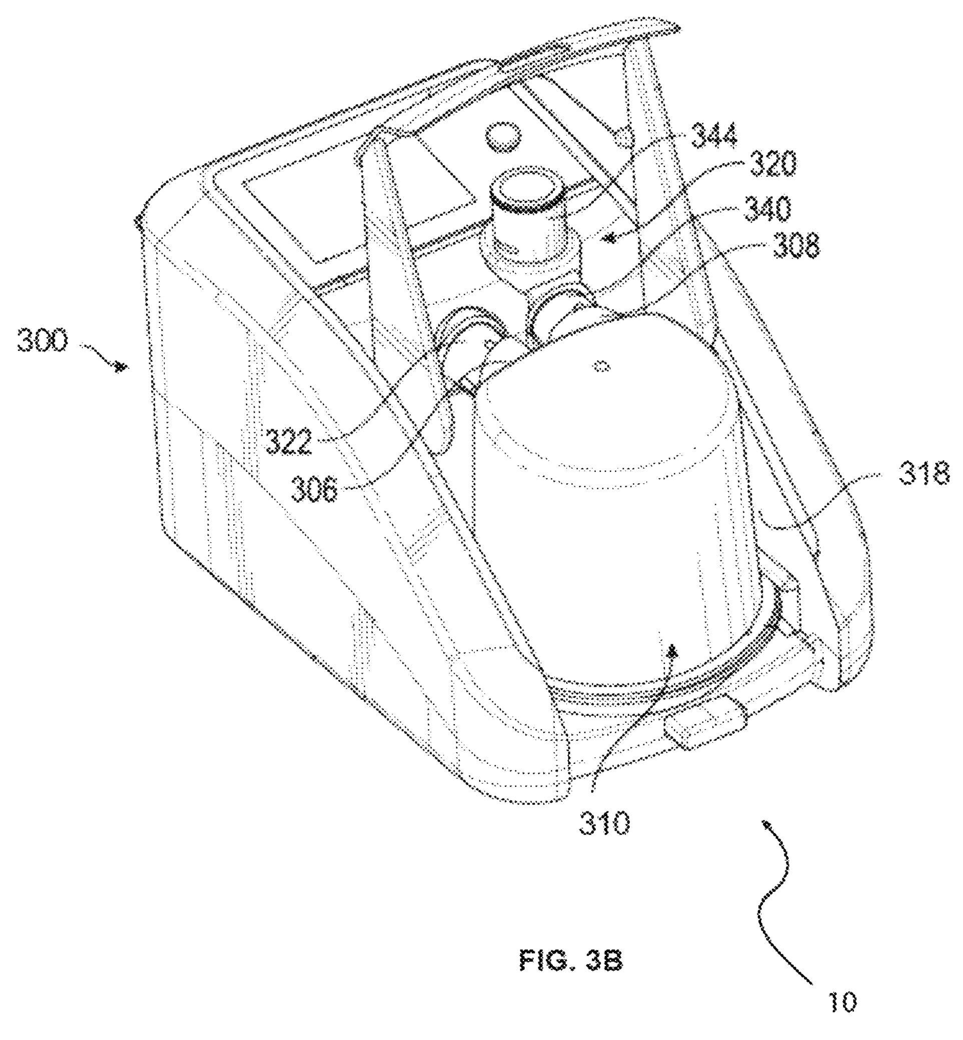
FIG. 3B is a front perspective view of an example breathing assistance apparatus with a humidification chamber in position.
Figure 3C:
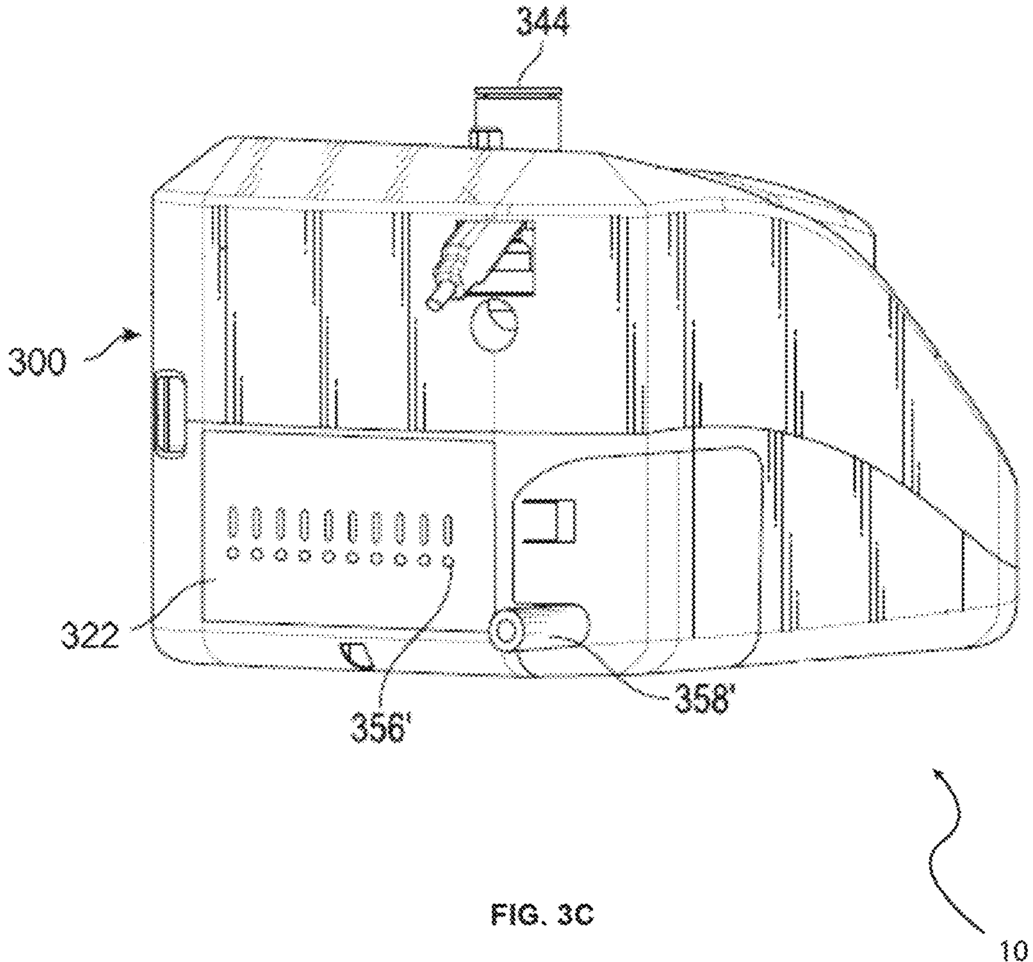
FIG. 3C is a back perspective view of the breathing assistance apparatus of FIG. 3B.

High flow therapy as discussed herein is intended to be given its typical ordinary meaning as understood by a person of skill in the art which generally refers to a respiratory assistance system delivering a targeted flow of humidified respiratory gases via an intentionally unsealed patient interface with flow rates generally intended to meet or exceed inspiratory flow of a patient FIGS. 3B and 3C show an example breathing assistance apparatus 10. The device can include a housing 300, which at least partially encloses a flow generator. The flow generator may include a motor and/or sensor module. The motor and/or sensor module may be non-removable from the main housing 300. The motor and/or sensor module can also optionally be removable from the main housing 300. The housing 300 can include a humidifier or humidification chamber bay 318 for receipt of a removable humidification chamber 310. The removable humidification chamber 310 contains a suitable liquid such as water for heating and humidifying gases delivered to a patient. The humidification chamber 310 can be fluidly coupled to the device housing 300 in a linear slide-on motion into the chamber bay 318. A gas outlet port 322 can establish a fluid communication between the motor and/or sensor module and an inlet 306 of the chamber 310.

Heated and humidified gas can exit an outlet 308 of the chamber 310 into a humidified gas return 340, which can include a removable L-shaped elbow. The removable elbow can further include a patient outlet port 344 for coupling to the inspiratory conduit, such as the inspiratory conduit 16 of FIG. 3A to deliver gases to the patient interface 17. The gas outlet port 322, humidified gas return 340, and patient outlet port 344 each can have seals such as O-ring seals or T-seals to provide a sealed gases passageway between the device housing 300, the humidification chamber 310, and the inspiratory conduit. A floor portion of the humidification chamber bay 318 in the housing 300 can include a heater arrangement such as a heater plate or other suitable heating element(s) for heating the water in the humidification chamber 310 for use during a humidification process. The elbow may comprise one or more integrated sensors. For example, the elbow may comprise a pair of embedded temperature sensors.

The elbow being removable may be advantageous as it means it can be removed and disinfected between use by different patients.

As shown in FIG. 3C, the device can include an arrangement to enable the flow generator to deliver air, oxygen (or alternative auxiliary gas), or a suitable mixture thereof to the humidification chamber 310 and thereby to the patient. This arrangement can include an air inlet 356' in a rear wall 322 of the housing 300. The device can include a separate oxygen inlet port 358'. In the illustrated configuration, the oxygen inlet port 358' can be positioned adjacent one side of the housing 300 at a rear end thereof. The oxygen port 358' can be connected to an oxygen source such as a tank, or an oxygen blender. The oxygen inlet port 358' can be in fluid communication with a valve. The valve can for example be a solenoid valve, a proportional valve, and/or any other suitable valve that enables the control of the amount of oxygen that is added to the gas flow that is delivered to the humidification chamber 310. The arrangement to enable the flow generator to deliver air, oxygen (or alternative auxiliary gas), or a suitable mixture thereof is disclosed in more detail below in relation to FIG. 4A.

The housing 300 can include suitable electronics boards, such as sensing circuit boards. The electronics boards can contain, or can be in electrical communication with, suitable electrical or electronics components, such as but not limited to microprocessors, capacitors, resistors, diodes, operational amplifiers, comparators, and switches. One or more sensors can be used with the electronic boards. Components of the electronics boards (such as but not limited to one or more microprocessors) can act as the controller 13 of the apparatus. One or both of the electronics boards can be in electrical communication with the electrical components of the system 10, including but not limited to the display unit and user interface 14, motor, valve, and the heater plate to operate the motor to provide the desired flow rate of gases, humidify and heat the gases flow to an appropriate level, and supply appropriate quantities of oxygen (or quantities of an alternative auxiliary gas) to the gases flow.

The display may comprise one or more of: a touchscreen and/or one or more mechanical input devices.

As mentioned above, operation sensors, such as flow, temperature, humidity, and/or pressure sensors can be placed in various locations in the breathing assistance apparatus, the patient conduit 16, and/or cannula 17. The electronics boards can be in electrical communication with those sensors. Output from the sensors can be received by the controller 13, to assist the controller 13 to operate the breathing assistance system 10 in a manner that provides optimal therapy, including meeting inspiratory demand. One or more sensors (for example, Hall-effect sensors) may be used to measure a motor speed of the motor of the flow generator. The motor may include a brushless DC motor, from which motor speed can be measured without the use of separate sensors. For example, during operation of a brushless DC motor, back-EMF can be measured from the non-energized windings of the motor, from which a motor position can be determined, which can in turn be used to calculate a motor speed. In addition, a motor driver may be used to measure motor current, which can be used with the measured motor speed to calculate a motor torque. The motor may also include a low inertia motor.

Room air can enter the flow generator through the inlet port, such as the air inlet port 356' in FIG. 3C. The flow generator can operate at a motor speed of greater than 1,000 RPM and less than 30,000 RPM, greater than 2,000 RPM and less than 21,000 RPM, greater than 4,000 RPM and less than 15000 RPM, or between any of the foregoing values. Operation of the flow generator can mix the gases entering the flow generator, such as the motor and/or sensor chamber through the inlet port. Using the flow generator as the mixer can reduce the pressure drop that would otherwise occur in a system with a separate mixer, such as a static mixer comprising baffles, because mixing requires energy.

In some embodiments, the breathing assistance apparatus (or for example part of the apparatus such as the flow generator) may enter a standby mode when therapy is paused or stopped. In the standby mode, the motor speed is maintained at a low fixed speed, for example, between 1,000 RPM and 3,000 RPM. Maintaining a relatively low motor speed reduces the time it takes the impeller to reach operational speed when therapy is resumed.

Figure 4:
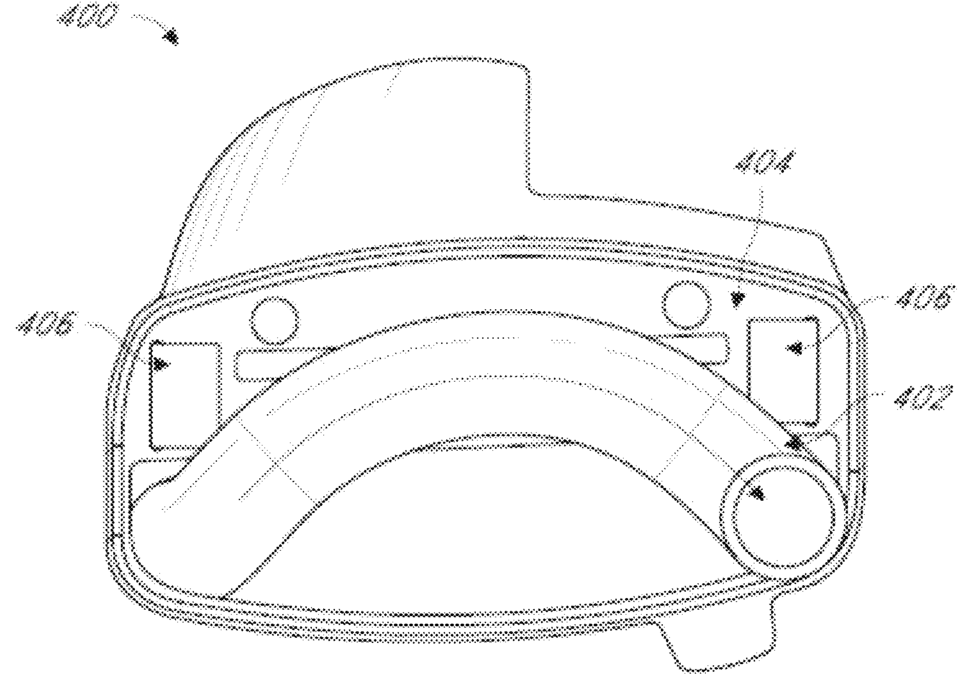
FIG. 4 illustrates an example sensing chamber of the breathing assistance apparatus of FIG. 3B.

As shown in FIG. 4, the mixed air can exit the flow generator and enter a flow path 402 in a sensor chamber 400, which can be located in the motor and/or sensor module. A sensing circuit board 404 with sensors, such as ultrasonic sensors 406 and/or heated thermistor flow sensors, can be positioned in the sensor chamber 400 such that the sensing circuit board is at least partially immersed in the gas flow. At least some of the sensors on the sensing circuit board can be positioned within the gas flow to measure gas properties within the flow. After passing through the flow path 402 in the sensor chamber 400, the gas can exit to the humidification chamber 310.

Positioning sensors downstream of the flow generator can increase accuracy of measurements, such as the measurement of gases fraction concentration, including oxygen concentration, over systems that position the sensors upstream of the flow generator and/or the mixer. Such a positioning can give a repeatable flow profile. Further, positioning the sensors downstream of the combined flow generator and mixer avoids the effect of the pressure drop that would otherwise occur when sensing occurs prior to the flow generator and a separate mixer. Also, immersing at least part of the sensing circuit board and sensors in the flow path can increase the accuracy of measurements because the sensors being immersed in the flow are more likely to be subject to the same conditions, such as temperature and pressure, as the gas flow and therefore provide a better representation of the gas flow characteristics.

As shown in FIG. 4, the flow path 402 can have a curved shape. The flow path 402 can be configured to have a curved shape with no sharp turns. The flow path 402 can have curved ends with a straighter section between the curved ends. A curved flow path shape can reduce pressure drop in a gas flow without reducing the sensitivity of flow measurements by partially coinciding a measuring region with the flow path to form a measurement portion of the flow path.

The sensing circuit board 404 can include sensors such as acoustic transmitters and/or receivers, flow sensor, pressure sensor (for example absolute or relative), humidity sensor, temperature sensor, thermistor, and the like (or for example other sensors as disclosed elsewhere in the specification).

A gas flow rate may be measured using at least two different types of sensors. The first type of sensor can include a thermistor, which can determine a flow rate by monitoring heat transfer between the gases flow and the thermistor. The thermistor flow sensor can run the thermistor at a constant target temperature within the flow when the gas flows around and past the thermistor. The sensor can measure an amount of power required to maintain the thermistor at the target temperature. The target temperature can be configured to be higher than a temperature of the gas flow, such that more power is required to maintain the thermistor at the target temperature at a higher flow rate.

The thermistor flow rate sensor can also maintain a plurality of (for example, two, three, or more) constant temperatures on a thermistor to avoid the difference between the target temperature and the gas flow temperature from being too small or too large. The plurality of different target temperatures can allow the thermistor flow rate sensor to be accurate across a large temperature range of the gas. For example, the thermistor circuit can be configured to be able to switch between two different target temperatures, such that the temperature of the gas flow can always fall within a certain range relative to one of the two target temperatures (for example, not too close and not too far). The thermistor circuit can be configured to operate at a first target temperature of about 50° C. to about 70° C., or about 66° C. The first target temperature can be associated with a desirable flow temperature range of between about 0° C. to about 60° C., or about 0° C. and about 40° C. The thermistor circuit can be configured to operate at a second target temperature of about 90° C. to about 110° C., or about 100° C. The second target temperature can be associated with a desirable flow temperature range of between about 20° C. to about 100° C., or about 30° C. and about 70° C.

The controller can be configured to adjust the thermistor circuit to change between at least the first and second target temperature modes by connecting or bypassing a resistor within the thermistor circuit. The thermistor circuit can be arranged as a Wheatstone bridge configuration comprising a first voltage divider arm and a second voltage divider arm. The thermistor can be located on one of the voltage divider arms. More details of a thermistor flow rate sensor are described in International Patent No. WO2018052320A2, the entirety of which is incorporated by reference herein.

The second type of sensor can include an acoustic (such as ultrasonic) sensor assembly. Acoustic sensors including acoustic transmitters and/or receivers can be used to measure a time of flight of acoustic signals to determine gas velocity and/or composition, which can be used in flow therapy apparatuses. In one ultrasonic sensing (including ultrasonic transmitters and/or receivers) topology, a driver causes a first sensor, such as an ultrasonic transducer, to produce an ultrasonic pulse in a first direction. A second sensor, such as a second ultrasonic transducer, receives this pulse and provides a measurement of the time of flight of the pulse between the first and second ultrasonic transducers. Using this time of flight measurement, the speed of sound of the gas flow between the ultrasonic transducers can be calculated by a processor or controller of the breathing assistance apparatus. The second sensor can also transmit and the first sensor can receive a pulse in a second direction opposite the first direction to provide a second measurement of the time of flight, allowing characteristics of the gas flow, such as a flow rate or velocity, to be determined. In another acoustic sensing topology, acoustic pulses transmitted by an acoustic transmitter, such as an ultrasonic transducer, can be received by acoustic receivers, such as microphones. More details of an acoustic flow rate sensor are described in International Patent No. WO2017095241A3, which is incorporated by reference herein in its entirety. The acoustic pulses can be transmitted along the flow path of the gases, thereby allowing the acoustic sensors to be used to measure a flow rate or velocity of the gases.

The ultrasonic sensor as described above may provide a sensor that provides a fast response. This allows a controller to control a valve that can adjust the amount of O2 in the gases stream. Alternatively, other gas composition sensors could be used.

Readings from both the first and second types of sensors can be combined to determine a more accurate flow measurement. For example, a previously determined flow rate and one or more outputs from one of the types of sensor can be used to determine a predicted current flow rate. The predicted current flow rate can then be updated using one or more outputs from the other one of the first and second types of sensor, in order to calculate a final flow rate.

Figure 4A:
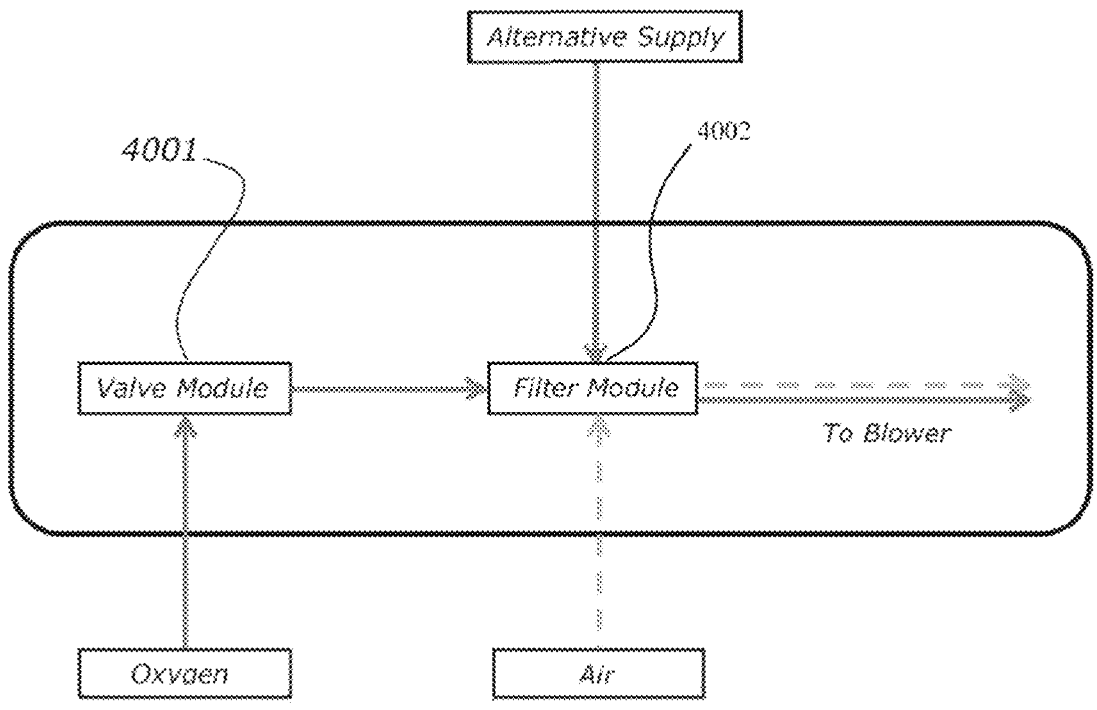
FIG. 4A illustrates an example apparatus including a valve module.

For example, as shown in FIG. 4A, the apparatus may comprise a valve module 4001 that controls the flow of oxygen and/or other gases entering the gas flow path of the apparatus and enables the apparatus to regulate the proportion of oxygen entrained in the airflow. The valve module is formed as a modular unit for ease of manufacture, assembly, servicing, or replacement. For example, in the event of malfunction, routine maintenance, or future upgrade/improvement.

The valve module may be configured to operate to control the oxygen concentration of the gases provided to the user to at a therapy oxygen concentration.

The apparatus may comprise a filter module 4002, which may comprise a filter.

The filter modules 4002 and valve modules 4001 described herein may provide varying gas flow paths for the apparatus. For example, the valve module may control the flow of oxygen entering the gas flow path of the apparatus, via the valve module and filter module. Alternatively, the valve module may be bypassed by means of direct connection of an alternative oxygen source to the filter module via an alternative supply inlet. This may be practical in circumstances where a user may wish to manually adjust the oxygen supply (i.e. by a wall-supply rotameter).

It will be appreciated that the filter modules and the valve modules described herein may be used separately in apparatuses for delivering a flow of gas. Alternatively, the filter and the valve module may be used together as a filter and valve assembly for improved functionality.

In the configurations shown, the apparatus 10 receives oxygen by at least one of the following:

- via the valve module (for automatic oxygen regulation by the apparatus), or
- via the alternative gases inlet provided on the top of the filter (allowing attachment of a manually adjustable oxygen supply—such as a wall supply regulated by a regulator).

The apparatus 10 may comprise a manifold. The manifold may be located on the housing. The manifold may provide one or more of: the oxygen inlet, the alternative gases inlet, and/or the air inlet.

The manifold may provide the oxygen, alternative gases, and/or ambient air to the valve module, filter module, and/or the blower.

The oxygen inlet or alternative gasses supply inlet may be provided on a side of the manifold.

The manifold may allow excess oxygen to overflow to the ambient environment, and/or may allow oxygen to overflow to the ambient environment if the blower is off and oxygen is continually supplied. This prevents accumulation of O2 in the housing.

The various configurations described are exemplary configurations only. Any one or more features from any of the configurations may be used in combination with any one or more features from any of the other configurations.

As another example, while the motor and/or sensor sub-assembly recess is described as being in the underside of the housing, it could alternatively be in the rear, side, front, or top of the housing. The air and/or oxygen inlets may also be positioned differently as required.

As another example, rather than the humidification chamber and chamber bay being configured so that the humidification chamber is inserted into and removed from the chamber bay from a front of the housing, the configuration could be such that the humidification chamber is inserted into and removed from the chamber bay from a side, rear, or top of the housing.

As another example, while the filter modules are described as being inserted into the housing from above and the valve modules inserted into the housing from below, either or both of those components could be inserted into any suitable part of the housing, such as an upper part, lower part, side part, front part, or rear part.

The filter module and valve module are described with reference to a breathing assistance apparatus that can deliver heated and humidified gases to a patient or user.

The filter module and/or valve module may alternatively be used with an apparatus that does not require a humidifier and therefore does not require the humidification chamber. For example, it will be appreciated that the configuration that isolates the motor and gas flow path from the electrical and electronic components has broad applications in other types of gas delivery apparatuses.

The breathing assistance apparatus may be configured to deliver high flow therapy (for example as shown in FIG. 3) or Bubble CPAP therapy (for example as shown in FIG. 2).

The breathing assistance apparatus may be changeable between one or more of a high flow therapy mode, a Bubble CPAP therapy mode, a CPAP therapy mode, and/or a bi-level therapy mode.

In the high flow therapy mode the breathing assistance apparatus is configured to provide high flow therapy In the Bubble CPAP therapy mode the breathing assistance apparatus is configured to provide bubble CPAP therapy.

The high flow therapy is nasal high flow therapy.

In the high flow therapy mode the system comprises an unsealed patient interface coupled to the inspiratory conduit 121.

The unsealed patient interface may be a nasal cannula.

In use, the nasal cannula is positioned on the user's face to provide gases to the nares of the user.

In the Bubble CPAP therapy mode the system comprises a sealed patient interface coupled to the inspiratory conduit 121, an expiratory conduit 130 coupled to the sealed patient interface.

The expiratory conduit 130 is coupled to a pressure regulator to regulate pressure within the patient interface and/or the patient's airways.

As described in more detail above, the pressure regulator comprises a chamber with a column of water and the expiratory conduit 130 being submerged into the column of water. The pressure provided to the user being defined or being set by the depth the submersion of the expiratory conduit 130 within the column of water.

In some embodiments, the flow generator (as part of the breathing assistance apparatus) is configured to provide a flow of gases via a gases flow pathway at a target flow rate and/or a target pressure.

The controller may control a motor output (for example motor speed or motor current) of the motor to achieve the target flow rate.

The target pressure may be controlled by the pressure regulator as described above.

In some embodiments, the gases flow pathway may comprise an inspiratory conduit connected to a patient interface, and an expiratory conduit connected to a pressure regulator.

The gases flow pathway may comprise part of the breathing assistance apparatus through which gases flow.

The inspiratory conduit 121 may be common between the high flow therapy mode and the bubble CPAP therapy mode.

The same inspiratory conduit being useable for both modes reduces the number of components that are required to be interchanged when changing mode.

Further this common inspiratory conduit allows the same breathing assistance apparatus comprising a flow generator and humidifier integrated into a housing to be used for both bubble CPAP mode and high flow mode. Further the integrated humidifier and flow generator in a common housing makes it simple to transition between bubble CPAP and other therapy modes (for example non bubble CPAP modes such as high flow modes) since a single device can be used, rather than unique set ups of several components as required in prior art systems.

The present system provides a single breathing assistance apparatus that can be used to deliver both bubble CPAP therapy and high flow therapy, while only the interface requiring changes. There are no changes in components on the gases supply side i.e. no changes in the gases supply components since a common breathing assistance apparatus can be used to deliver humidified gases.

The controller may comprise a high flow therapy control program associated with the high flow therapy mode.

The controller may comprise a bubble CPAP therapy control program associated with the bubble CPAP therapy mode.

In some embodiments, the high flow therapy mode may have a high flow therapy controller. Optionally the high flow therapy controller may be configured to run the high flow therapy control program.

In some embodiments, the bubble CPAP therapy mode may have a bubble CPAP therapy controller. Optionally the bubble CPAP therapy controller may be configured to run the bubble CPAP therapy control program.

The controller is configured to select and apply the program that corresponds to the selected mode of operation.

Each of the high flow therapy control program and the bubble CPAP therapy control program defines corresponding operating parameters.

In some embodiments, operating parameters may comprise one or more motor speed or pressure limits.

Operating parameters may comprise one or more alarm conditions.

One or more alarm conditions may comprise a lack of bubbling in the bubble CPAP therapy mode.

In some embodiments, an alarm may be activated when lack of bubbling is detected for more than a threshold period of time.

Operating parameters may define a humidity level.

Operating parameters may one or more temperature or dew point set points to control the humidifier.

The humidity level provided during the high flow mode may be greater than the humidity level provided during bubble CPAP therapy mode.

The operating parameters may also define a flow limit corresponding to each mode.

The controller may be configured to detect bubbling of the bubbler, and wherein if bubbling is detected the controller selects the bubble CPAP therapy mode.

The controller may be configured to detect bubbling of the bubbler in all therapy modes (such as bubble CPAP and high flow therapy modes). For example, the detection of bubbling may be undertaken continuously or periodically during operation of the apparatus.

In some embodiments, detection of bubbling may be undertaken at an initiation of therapy.

In some embodiments, detection of bubbling may be undertaken for a predetermined time at or near the initiation of therapy.

In some embodiments the detection of bubbling may be undertaken for a within a predetermined time of the initiation of therapy In some embodiments, detection of bubbling may be undertaken at or near the initiation of a non-bubble CPAP mode (for example a high flow therapy mode). If bubbling is detected in a non-bubble CPAP mode the controller may raise one or more alarms (for example a notification) and/or automatically change to a bubble CPAP mode.

In some embodiments, detection of bubbling may be undertaken when the mode of therapy changes.

In some embodiments, detection of bubbling may be undertaken when the user changes one or more therapy settings (for example flow rate set point and/or pressure set point).

In some embodiments, detection of bubbling may be undertaken when the apparatus is in a non bubble CPAP mode.

When bubbling is detected during a non bubble CPAP mode (for example a high flow therapy mode), the controller may generate an alarm or notification indicating that the bubbler is connected and/or the wrong therapy mode is selected.

The controller may select the bubble CPAP therapy mode once bubbling has been detected for a predetermined amount of time.

The controller may present the user with a message to consider changing the mode to the bubble CPAP therapy mode once bubbling has been detected (optionally for a predetermined amount of time.)

The controller may automatically select a therapy mode based on whether a bubbler is connected and/or bubbling is detected in the bubbler.

The controller may automatically switch mode to the bubble CPAP therapy mode if a bubbler is detected by bubbling.

The controller may automatically switch modes to the bubble CPAP therapy mode if bubbling is detected in the bubbler.

The controller may limit the flow rate if bubbling is detected. Limiting the flow rate in this case may provide protection to a patient if an incorrect mode (for example a non bubble CPAP mode) is selected. The controller may limit the flow rate if bubbling is detected in a non bubble CPAP mode.

The controller may limit a flow rate set point automatically if bubbling is detected in a non bubble CPAP mode.

If bubbling is detected in a non bubble CPAP mode the controller may provide an alert to the user notifying them that bubbling has been detected, and/or that a limit has been applied to the flow rate set point. The user may be given the ability override the limit applied to the flow rate set point.

When automatically switching to the bubble CPAP therapy mode, the controller may maintain the current flow rate or adjust to a flow rate appropriate for bubble CPAP therapy.

When automatically switching to the bubble CPAP therapy mode, the controller may control the apparatus based on a set of safe operating parameters (for example a safe flow rate, pressure limits etc.) the set of safe operating parameters may comprise one or more ranges, or limit thresholds.

In some embodiments, when no bubbling is detected but the controller is not configured to automatically change to a bubble CPAP mode, the controller may still monitor alarms and thresholds as per a bubble CPAP mode.

When automatically switching to the bubble CPAP therapy mode, the controller may generate a notification to prompt a user to switch a bubble CPAP interface.

When switching to the bubble CPAP therapy mode, the apparatus may present an option via a user interface to change to a bubble CPAP mode that can be selected by the user.

In some embodiments, the detection of bubbling may be used to detect incorrect peripheral components (such as patient interface, conduit, etc.) used the breathing support apparatus and/or therapy modes.

A user may select the high flow therapy mode, or the bubble CPAP therapy mode (optionally via a user interface).

The detection of bubbling may be that as described elsewhere in the specification.

The breathing assistance apparatus can also be configured to detect the presence of bubbling in the bubbler (or other pressure regulator). Bubbling can be useful in indicating that the system is operating correctly. For example, a temporary lack of bubbling can indicate that the peak inspiratory flow of the patient is exceeding the flow rate delivered by the device at that moment (i.e. the flow rate delivered by the breathing assistance apparatus is not enough). Additionally, a prolonged lack of bubbling can indicate that there may be a leak in the gas pathway, such as for example between the connection of components.

Oscillations in pressure and/or flow may be caused by events such as breathing and bubbling. The pressure and/or flow oscillations associated with each event may comprise a different signature that can be used to distinguish between these events. Bubbling can be detected by detecting the presence of a bubbling oscillation signature in the pressure and/or flow caused by the discharge of gas through the bubbler. In breathing assistance systems in which the flow rate is being controlled by the controller, the controller can use a pressure signal, such as from the pressure sensors, or a flow signal such as from the flow sensor (both disclosed elsewhere in the specification) to determine the presence of bubbling.

During normal operation of the system, the controller may monitor the pressure and/or flow rate of the gas using a pressure and/or flow sensor as described above.

However, detection of the pressure or flow variation (for example bubbling) is more complex due to a number of factors, including but not limited to, variations in amplitudes depending on the therapy provided and the components used, the presence of breathing related pressure and/or flow oscillations, and characteristics of the flow and pressure signals according to the level of flow that passes through the water and the variability of height of the water column.

Additionally, variations in bubbling patterns due the presence of leaks and/or blockage (e.g. condensation in the circuit) may add to the complexity of bubbling detection.

Determination of whether bubbling is occurring may be based on at least one characteristic indicative of bubbling in the pressure regulator.

At least one characteristic indicative of bubbling in the bubbler pressure regulator may be determined by one or more of: a visual sensor (for example a vision sensor) configured to output a signal indicative of an image of the bubbler, a water level sensor, a microphone, an optical sensor a gas flow characteristic sensor.

The sensors described above may output a signal indicative of at least one characteristic indicative of bubbling in the pressure regulator.

The controller may be configured to determine whether bubbling is occurring based on the signal indicative of at least one characteristic indicative of bubbling in the pressure regulator.

The controller may be configured to determine whether bubbling is occurring based on the signal indicative of at least one characteristic indicative of bubbling in the pressure regulator over a period of time.

Detection bubbling is occurring in the pressure regulator may indicate that therapy is being provided.

The controller may be configured to determine whether bubbling is occurring based on one or more waveform characteristics of the signal indicative of at least one characteristic indicative of bubbling in the pressure regulator (for example as described in more detail below).

The visual sensor (for example a vision sensor) may be configured to output a signal indicative of an image of at least a portion of the pressure regulator (as the signal indicative of at least one characteristic indicative of bubbling in the pressure regulator). The visual signal indicative of an image of at least a portion of the pressure regulator may comprise an image of at least a portion of the water surface, and/or an area surrounding the outlet of the respiratory conduit in the pressure regulator.

Based on the signal indicative of an image of at least a portion of the pressure regulator (for example over a period of time), the controller may determine for example a liquid (for example water) level of the pressure regulator and a liquid disturbance (for example the presence of bubbles) in the liquid of the pressure regulator.

The visual sensor may be for example a camera.

The water level sensor (for example monitoring the height of the water in the bubbler) configured to output a signal indicative of the surface of the water in the bubbler, (as the at least one characteristic indicative of bubbling in the pressure regulator). In some embodiments, the water level sensor might be a limit switch that changes state when the water level exceeds a threshold.

The water level sensor may be for example a time-of-flight sensor, and/or a laser based sensor (for example LIDAR), and or an electrical resistance sensor.

The microphone may be configured to output a signal indicative of the sound generated by the bubbler, (as the signal indicative of the at least one characteristic indicative of bubbling in the pressure regulator).

The microphone may for example comprise an ultrasonic sensor and/or any other audio signal receiver.

The optical sensor may be configured to output a signal indicative of the optical properties of the liquid in the bubbler, (as the signal indicative of the at least one characteristic indicative of bubbling in the pressure regulator).

The optical sensor may for example comprise a laser or infrared sensor.

The gas flow characteristic sensor may be configured to output a signal indicative of a characteristic of the gas flow in the apparatus (for example a flow sensor or a pressure sensor—as described in more detail below).) as the signal indicative of the at least one characteristic indicative of bubbling in the pressure regulator.

In some embodiments the microphone may be located in the flow path (for example in the sensor chamber 400), or external to the flow path. In some embodiments, the microphone may be located in or at the bubbler.

In some embodiments, the determination of whether bubbling is occurring is based on a flow generator characteristic. The flow and pressure perturbations caused by bubbling in the bubbler may affect the flow generator.

The flow generator characteristic may be for example a valve characteristic, motor characteristic (i.e., the motor of a blower or a flow generator).

In some embodiments, the valve characteristic may be a valve current, or a valve voltage, or other valve output.

As the motor of the blower provides the flow to the patient, bubbling in the bubbler may affect one or more motor characteristics. For example, bubbling may lead to differences disturbances in motor speed or motor torque caused by the varying flow and/or pressure caused in the blower by the bubbling.

The motor characteristic may be for example a motor speed (or indicative of motor speed), or motor torque (or indicative of motor torque).

In some embodiments, determination of whether bubbling is occurring is based on determining pressure or flow oscillations in a waveform, for example a pressure or a flow waveform, indicative of bubbling in the pressure regulator.

It will be appreciated that the determination of bubbling may be based on any combination of the above.

The controller may determine at least one waveform based on the measurement of the flow rate and/or pressure of the gases in the gases flow path.

In some embodiments, at least one waveform may additionally or alternatively, be based on the measurement of another characteristic of bubbling in the pressure regulator (for example the signal indicative of the at least one characteristic indicative of bubbling in the pressure regulator as described in more detail above).

The or each waveform may be the signal indicative of the at least one characteristic indicative of bubbling in the pressure regulator (for example the measurement of the flow rate and/or pressure of the gases in the gases flow path (for example over a time period). Additionally, or alternatively the waveform may be based on one or more signal processing techniques (for example analog signal processing, continuous time processing, discrete time processing, digital signal processing, nonlinear signal processing, statistical signal processing). Additionally, or alternatively the waveform may be based on one or more curve fitting techniques. Additionally, or alternatively the waveform may be based on a filtered output of the measurement of the flow rate or pressure of the gases in the gases flow path.

The waveform may be based on a combination of the measurement of the flow rate or pressure of the gases in the gases flow path. For example, the measurement of the flow rate of the gases in the gases flow path may be combined with the measurement of the pressure of the gases in the gases flow path. The combination may be for example multiplied together of combined as a weighted average.

The controller may determine at least one waveform characteristic based on the flow and/or pressure waveform (for example the output of the flow and/or pressure sensors).

The controller may determine whether bubbling is occurring in the pressure regulator based on the at least one waveform characteristic.

The controller may be configured to display whether bubbling is occurring in the pressure regulator on a display.

The determination of whether bubbling is occurring in the pressure regulator may be over a time period (for example a time period extending back from the current time).

The controller may be configured to generate an alarm based on whether bubbling is occurring in the pressure regulator.

The controller may be configured to generate the alarm if it is determined bubbling is not occurring in the pressure regulator.

The controller may be configured to generate the alarm if it is determined the percentage of time bubbling is occurring over a time period is below a threshold, or the percentage of time bubbling is not occurring over a time period is above a threshold.

In some embodiments, the controller may be configured to generate an alarm if it is determined that the bubbling pattern is irregular.

In some embodiments, the alarm may be an audio and/or a visual alarm (for example via a display and/or user interface).

In some embodiments, the controller may be configured to monitor a pressure of the gases in the gases flow pathway.

In some embodiments, the controller may be configured to generate an alarm when the pressure of the gases flow exceeds a threshold.

The controller may be configured to generate an alarm prompting the user to check the inspiratory and/or expiratory conduit for condensate if it is detected that bubbling is not occurring in the pressure regulator.

Sensor Characteristics

The choice of flow and/or pressure sensors used in the breathing assistance apparatus may affect bubbling detection due to characteristics of sensors. For example, a choice of a particular sensor may lead to more measurement noise. These sensor characteristics need to be taken into account when detecting bubbling.

Figure 5:
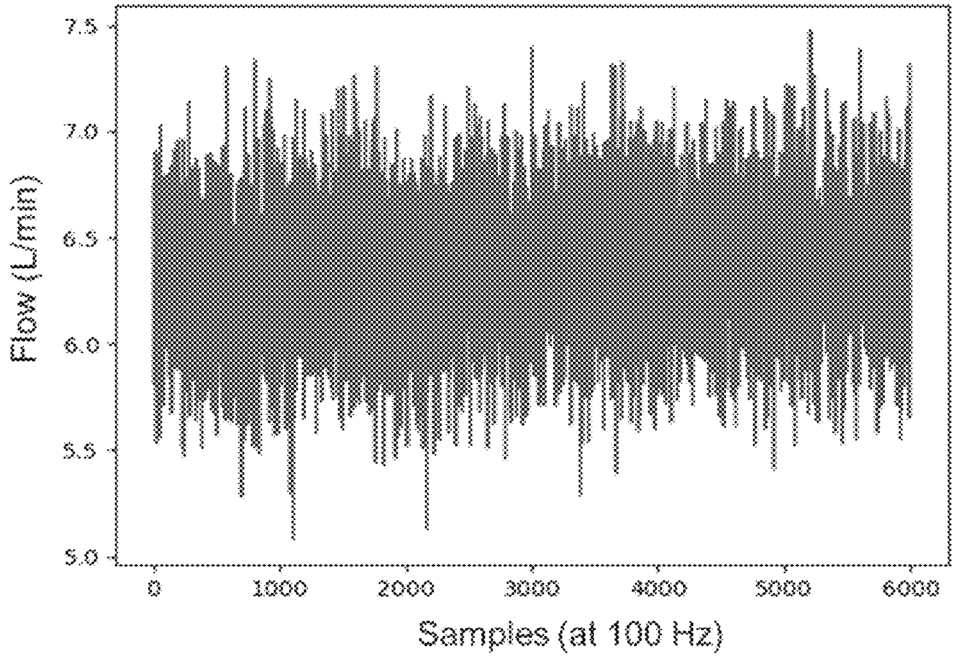
FIG. 5 illustrates an example of ultrasonic flow sensor measurement.

An ultrasonic flow sensor may have high frequency measurement noise with an amplitude that may exceed 2 L/min. FIG. 5 illustrates an example of the fluctuation of an ultrasonic flow sensor measurement for a flow level of 6 L/min (sampled at 100 Hz).

Figure 6A:
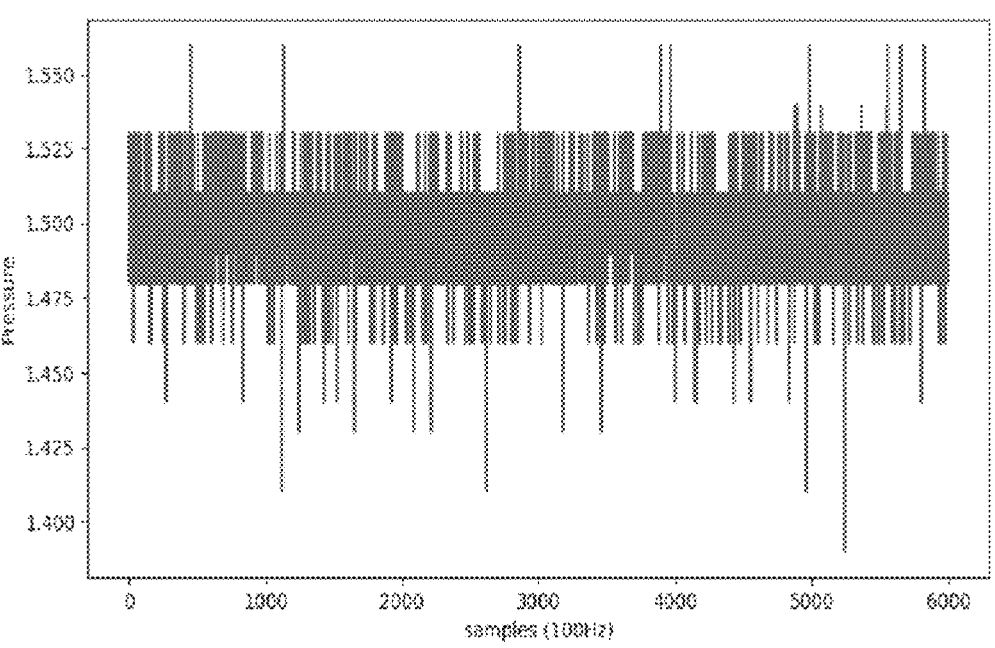
FIGS. 6A and 6B illustrate examples of pressure sensor measurement over time at two pressure levels.
Figure 6B:
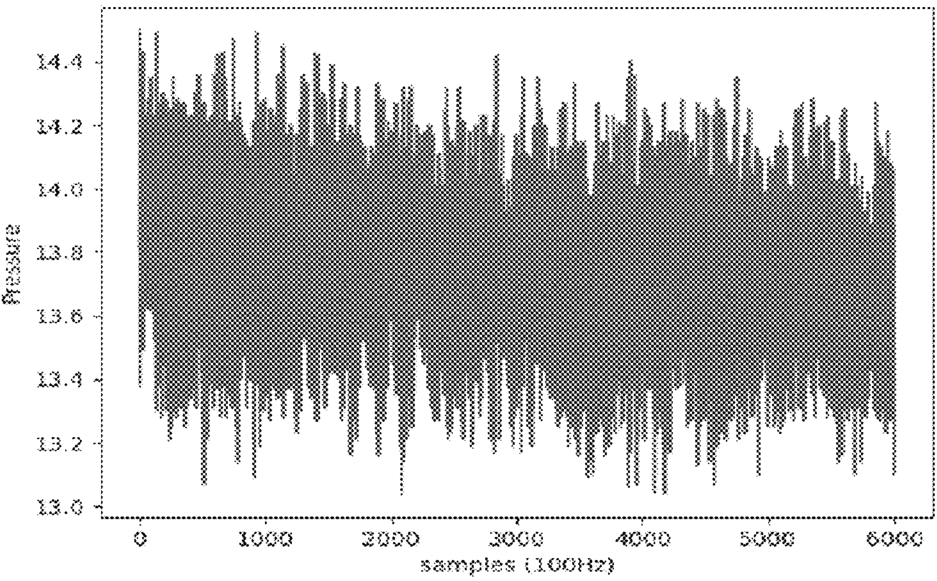

Pressure sensors (such as gauge or absolute pressure sensors) provided in the breathing assistance apparatus may have a lower measurement noise compared to an ultrasonic flow sensor. However, measurement noise in the pressure signal may increase substantially as measured pressure increases. FIGS. 6A and 6B illustrate examples of pressure sensor measurement over time for pressure levels of 1.5 $cmH_2O$ and 13 $cmH_2O$ (sampled at 100 Hz). At a pressure level of 1.5 $cmH_2O$, the range of pressure measurements may fluctuate by +/−0.1 $cmH_2O$. At a pressure level of 13 $cmH_2O$, the range of pressure measurements may fluctuate by +/−1 $cmH_2O$.

The pressure sensor may be located in the apparatus as for example described in more detail above.

In a first embodiment of determining whether bubbling is occurring, a bubbling detection algorithm 800 comprises a learning stage and monitoring stage may be used to detect and monitor bubbling.

Figure 8:
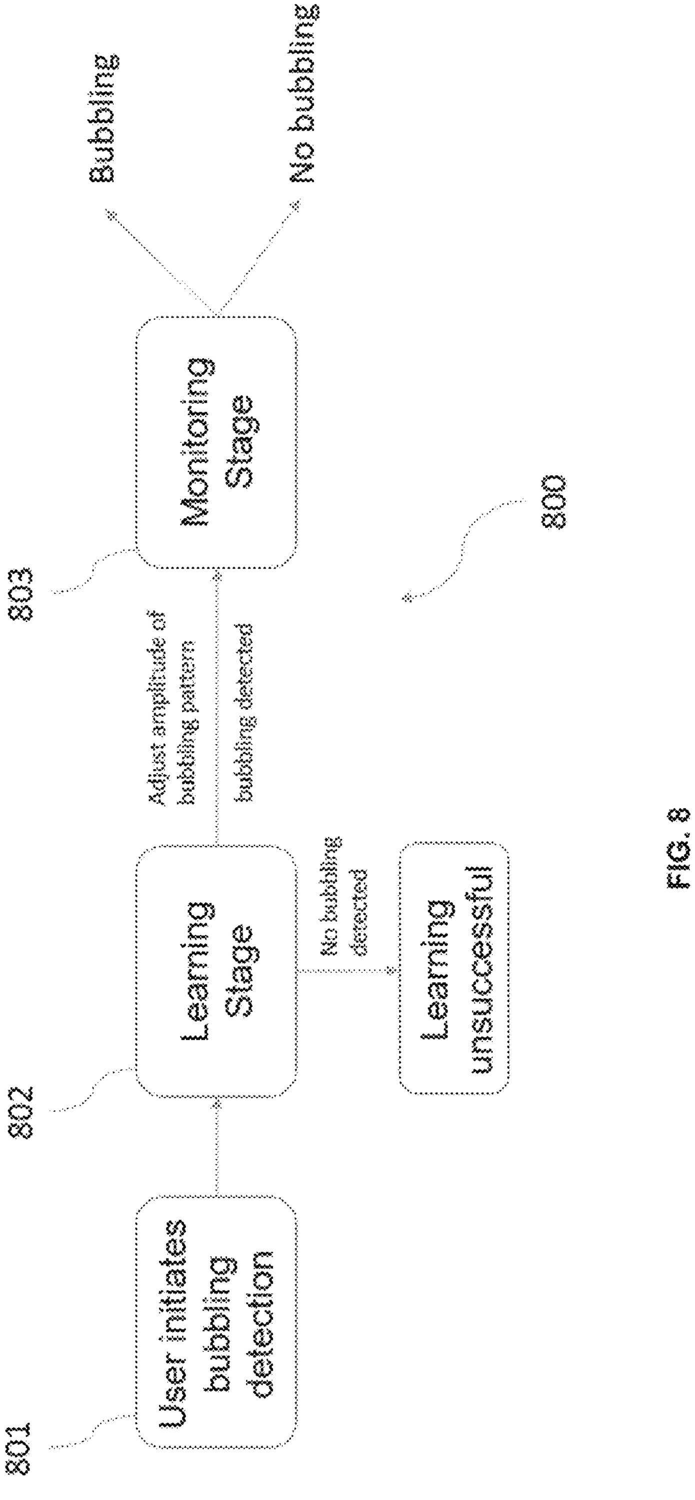
FIG. 8 illustrates an overview of bubbling detection according to one embodiment of the bubbling detection algorithm.

FIG. 8 illustrates an overview of bubbling detection according to one embodiment of the bubbling detection algorithm 800. At step 801, a user initiates the bubbling detection process. In some embodiments, the initiation of the bubbling detection may be automatic, or for example undertaken periodically.

At step 802, a learning stage commences to detect whether bubbling is occurring in the system, as described in more detail below. The learning stage will be unsuccessful if no bubbling is detected in the system. If the learning stage is successful and bubbles are detected, the algorithm proceeds to the monitoring stage (step 803). At step 803, the presence or absence of bubbling is monitored based on the bubbling pattern determined at the learning stage (step 802), as described in more detail below.

During the monitoring stage 803, the bubbling detection algorithm 800 may be re-initialized if the measured flow and/or pressure changes.

In some embodiments, the bubbling detection algorithm 800 may determine a bubbling pattern based on a number of counted peaks of a pressure and/or flow signal.

In some embodiments, the bubbling detection algorithm 800 may determine whether the bubbling pattern has changed, for example, due to a change in the flow rate, the height of the expiratory conduit in the pressure generator.

In some embodiments, the controller may indicate on a user interface the current stage of the bubbling detection. For example, the controller may indicate that the learning stage is in progress.

Figure 9:
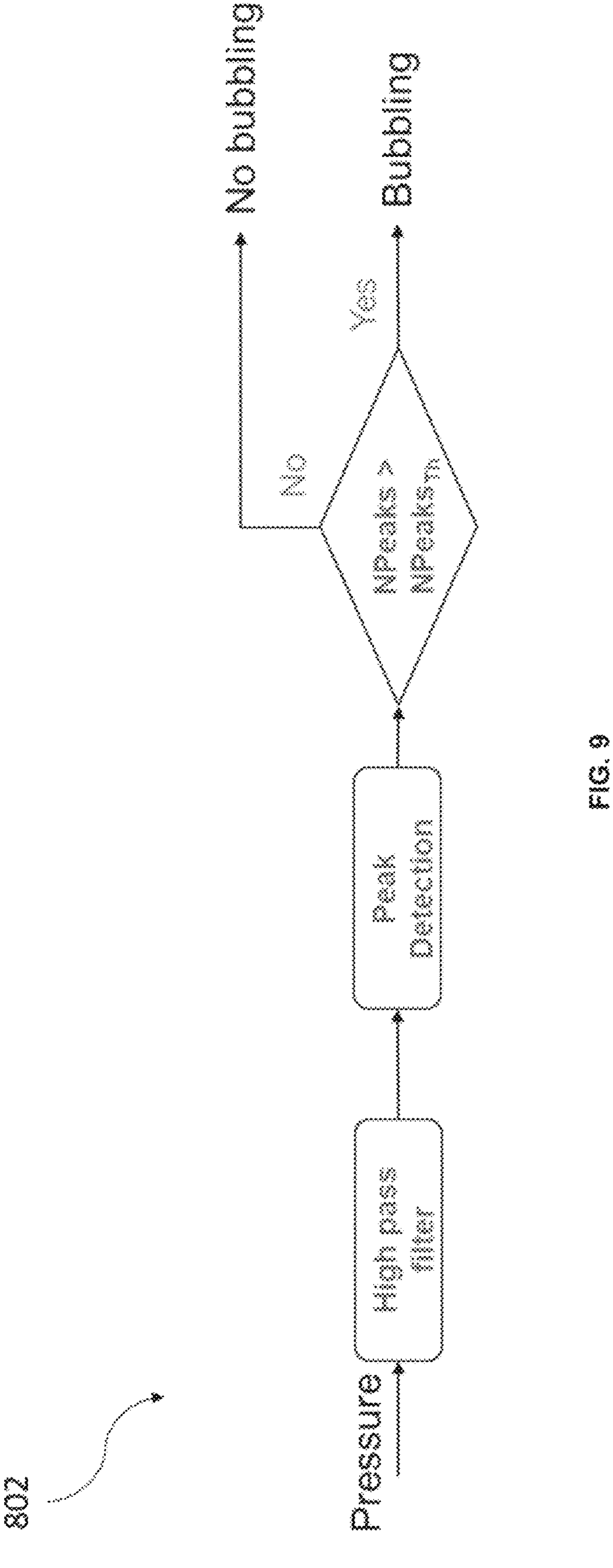
FIG. 9 illustrates an example of the learning stage according to one embodiment of the bubbling detection algorithm.

FIG. 9 illustrates an example of the learning stage 802. During the learning stage, the pressure signal may be filtered with a high-pass filter to remove DC and low frequency components. The high-pass filtered signal is then subjected to peak detection where the number of peaks (NPeaks) are detected over a detection time window (w). In some embodiments, bubbling is detected when the number of peaks exceeds a predetermined threshold.

The learning stage peak detection may occur over a suitable detection time window. In some embodiments, the learning stage peak detection occurs during a detection time window of about 1 second to about 10 seconds, or about 2 seconds to about 6 seconds, or about 4 seconds.

The learning stage may continue until bubbling is detected (i.e. peak detection thresholds are satisfied) within a detection time window. For example, if bubbling is detected within the first detection time window (e.g. 4 seconds), then learning stage is completed in 4 seconds. If no bubbling is detected in the first detection time window, a second, third, fourth, etc. detection window commences until bubbling is detected or the maximum learning stage duration is reached.

In some embodiments, the learning stage may last up to a maximum of about minutes before the learning stage is considered unsuccessful. For example, the maximum learning stage duration may be about 1 minute to about 10 minutes, or about 2 minutes to about 8 minutes, or about 4 minutes to about 6 minutes, or about 5 minutes.

The controller may generate an alarm or notification if no bubbling is detected after the maximum learning stage duration is reached.

The learning stage 802 requires a minimum level of disturbance in the pressure signal in order to proceed to the monitoring stage 803. In some embodiments, the minimum level of disturbance is a fixed peak detection threshold. In some embodiments, two peak detection thresholds may be used for the learning stage peak detection.

The peak detection thresholds may be coded into the controller. In some embodiments the peak detection thresholds may be configurable by the user, and/or be dynamically calculated by the system.

Figure 10:
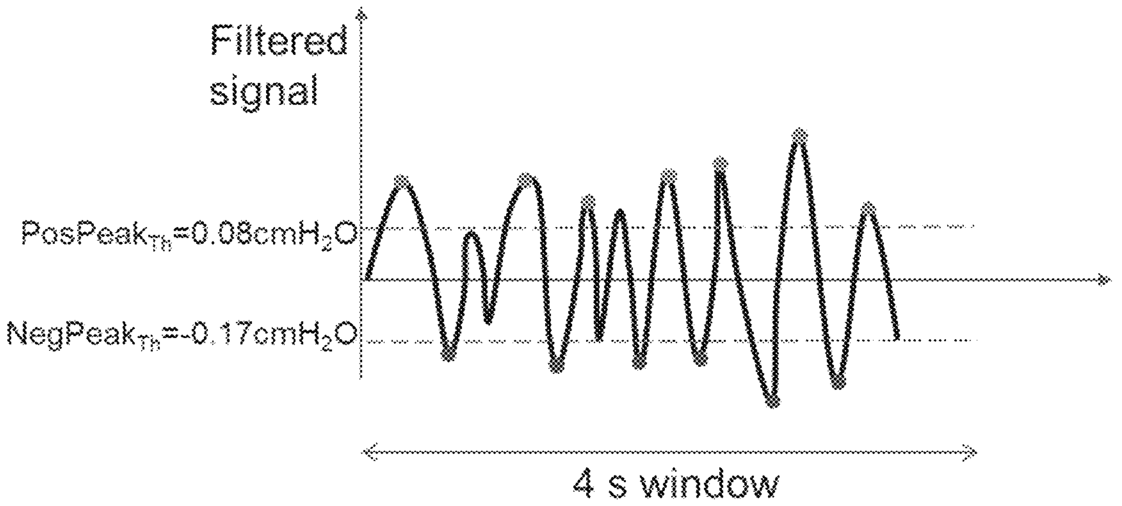
FIG. 10 illustrates an example of peak detection according to one embodiment of the bubbling detection algorithm.

FIG. 10 illustrates an example of peak detection using a positive peak threshold (PosPeakTh) and a negative peak threshold (NegPeakTh).

In the example of FIG. 10 the positive peak threshold (PosPeakTh) is 0.08 cmH2O and a negative peak threshold (NegPeakTh) is −0.17 cmH2O.

A positive peak is detected when the signal is above the PosPeakTh and a negative peak is detected when the signal is below the NegPeakTh. In some embodiments, the positive and negative peaks must alternate to be considered a valid peak detection.

If within the detection time window (e.g. 4 seconds), the number of positive peaks are greater than NPeakTh (24), bubbling is detected and the monitoring stage commences. Conversely, if the number of positive peaks is less than the NPeakTh, bubbling is not detected and the monitoring stage cannot commence and the bubbling detection algorithm is finalized. The learning stage 802 will need to be re-initialized in order to detect bubbling.

In some embodiments, the user may configure the learning stage peak detection threshold by adjusting a sensitivity setting on the apparatus. The sensitivity setting may correspond to the number of peaks (NPeakTh) and/or the detection time window (w) and/or the peak thresholds (PosPeakTh, NegPeakTh) required for bubbling detection. For example, a higher sensitivity setting may correspond to a lower NPeakTh value and/or a longer detection window and/or lower peak thresholds (PosPeakTh, NegPeakTh).

In some embodiments, the learning stage 802 is repeated (in some embodiments automatically) when the flow and/or pressure signals changes and/or when the target flow rate or other parameter is modified by a user. For example, the learning stage 802 is repeated if the height of the expiratory conduit is changed in the pressure regulator causing a change in the pressure signal.

In some embodiments, the controller may automatically repeat the learning stage 802 if it detect changes in the flow and/or pressure signals changes and/or when the target flow rate or other parameter is modified by a user. Additionally, or alternatively, the controller may generate a notification that the flow, pressure and/or parameter has changed and prompt a user to repeat the learning stage.

In some embodiments, the apparatus may display an indication the learning stage is occurring.

Similar to the learning stage 802, the monitoring stage 803 may also be based on the detection of positive and negative peaks. The monitoring stage 803 may be configured to specifically detect bubbling patterns determined during the learning stage 802. This may be achieved by adjusting the monitoring stage peak detection threshold as the average amplitude of a predetermined number of the most positive and/or negative peaks determined in the learning stage 802.

In some embodiments, the monitoring stage peak detection threshold may be adjusted based on the following rules:

i) The positive peak threshold for monitoring (positive peak threshold—MonitoringPosPeakTh) is set as the average amplitude of a number of (for example 16) the most positive peaks detected during the learning stage.

ii) The negative peak threshold for monitoring (negative peak threshold—MonitoringNegPeakTh) is set as the average amplitude of a number of (for example 16) the most negative peaks detected during the learning stage.

For example, bubbling is detected if the number of positive peaks are greater than a number of positive peaks threshold (MonitoringNPeakTh) (for example at least 6 peaks) over a time window of approximately 5 seconds (or for example a pressure signal frequency of 0.83 Hz or above). Peaks may be detected as described above (with respect to the learning stage) but with positive peak threshold—MonitoringPosPeakTh and negative peak threshold MonitoringNegPeakTh as peak thresholds In some embodiments, the user may configure the monitoring stage peak detection threshold by adjusting a sensitivity setting on the apparatus. The sensitivity setting may correspond to the number of peaks (number of positive peaks threshold—MonitoringNPeakTh) and/or the detection time window (w) and/or the peak thresholds (positive peak threshold—MonitoringPosPeakTh, negative peak threshold MonitoringNegPeakTh) required for bubbling detection. For example, a higher sensitivity setting may correspond to a lower number of positive peaks threshold—MonitoringNPeakTh value and/or a longer detection time window (w) and/or lower peak thresholds (positive peak threshold—MonitoringPosPeakTh, negative peak threshold—MonitoringNegPeakTh).

In some embodiments, the apparatus may display an indication the monitoring stage is occurring.

In a second embodiment of determining whether bubbling is occurring, bubbling detection may start automatically and adapt to changes to flow and/or pressure. In other words, a bubbling detection algorithm 1100 according to this embodiment may detect bubbling patterns across the entire flow and pressure range used for bubble CPAP therapy without a need for user intervention.

The bubble detection algorithm 1100 may use a model that continues to function despite changes to flow and/or pressure settings without the need for a learning stage or re-initialization (re-training).

In some embodiments, the bubbling detection algorithm 1100 detects a number of characteristics of a waveform of the flow and/or pressure signal that are indicative of the bubbling generated by passing gas flow through the column of water at the end of the expiratory conduit of the bubble CPAP circuit.

This approach differs to the above in that instead of counting a number of peaks above a threshold, a number of characteristics of the waveform are determined and used in a model to determine whether bubbling is occurring. This may allow for more information to be extracted from the flow or pressure signal as compared to counting a number of peaks.

Further, due to the variable measurement noise generated by the flow and/or pressure sensors, bubbling detection may be based on detecting/determining peaks above an amplitude sufficient to discriminate measurement noise from bubbling patterns.

Figure 7A:
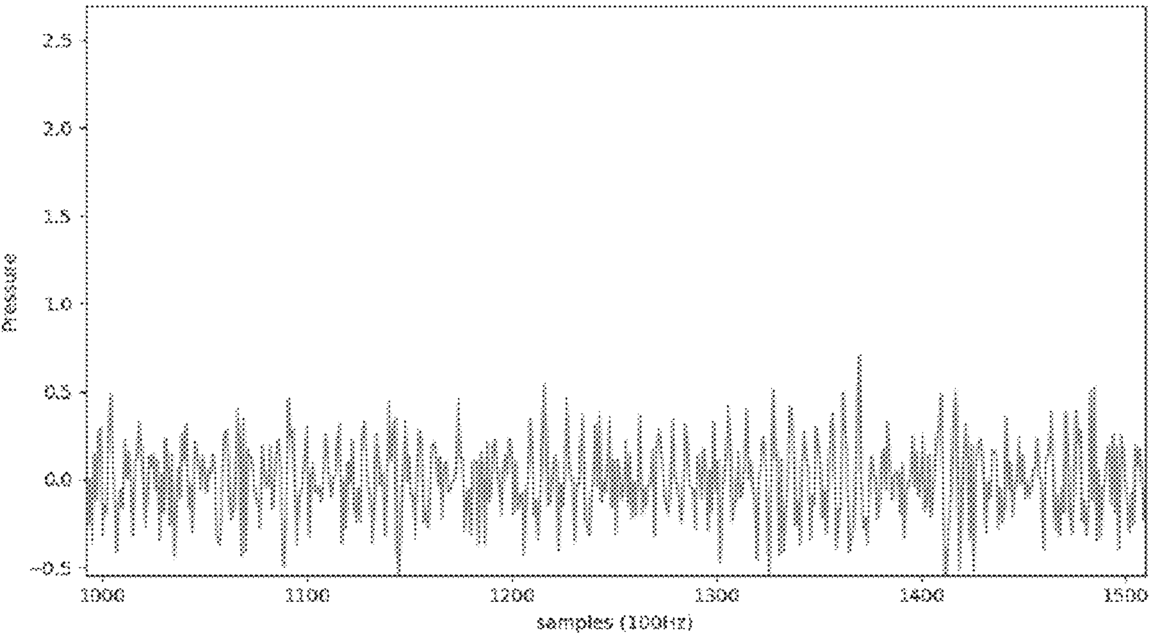
FIGS. 7A and 7B illustrate an example of a pressure signal with and without bubbling after removing DC levels.
Figure 7B:
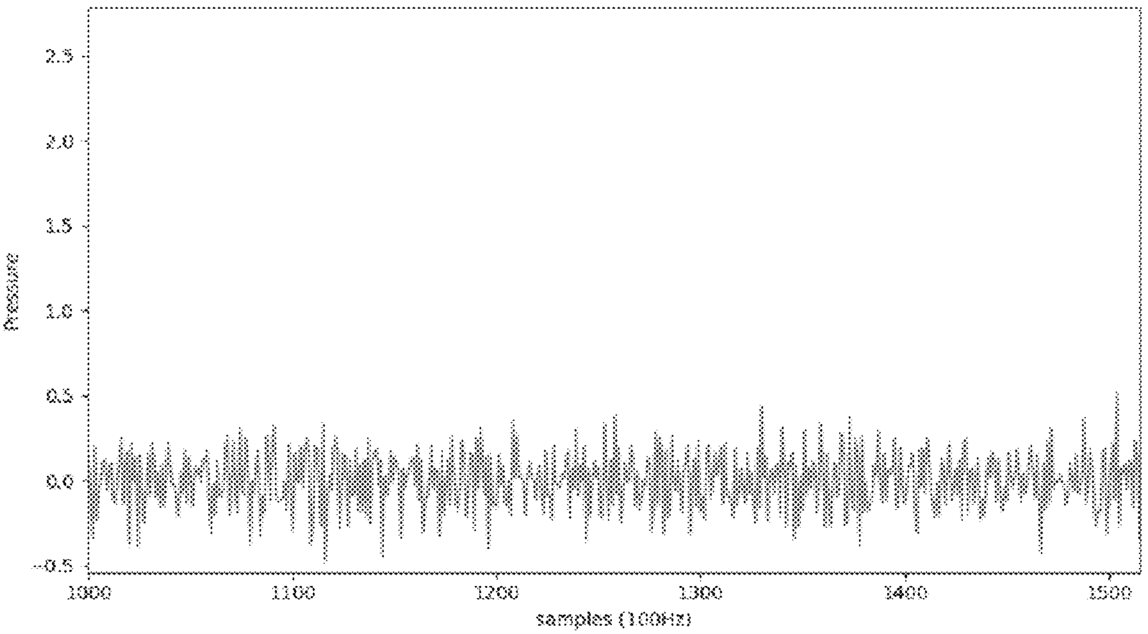

FIGS. 7A and 7B illustrate an example of a pressure signal with (FIG. 7A) and without bubbling (FIG. 7B), after removing DC levels. The at the pressure regulator pressure was set at 8 $cmH_2O$ and the flow at 10 L/min. A restrictor at the expiratory conduit was used to generate pressure in the configuration without bubbling.

The waveforms of FIGS. 7A and 7B were provided to the peak counting bubbling detection algorithm as described above, and for both waveforms the algorithm detected that bubbling was occurring (even though this was not the case in the waveform of FIG. 7B. This was likely due to sensor noise (described in more detail elsewhere). However, the methodology as described in more detail below is intended to minimize the risk of incorrect detection of bubbling by using a methodology that is more than counting peaks of a waveform (which as illustrated is susceptible to sensor noise).

In some embodiments, the bubbling detection algorithm 1100 may be based on inferring a model that maps an input signal (for example, flow and/or pressure) to the desired output (presence or absence of bubbling). The model inference may be implemented using a training classification algorithm with positive and negative examples of bubbling.

Figure 11:
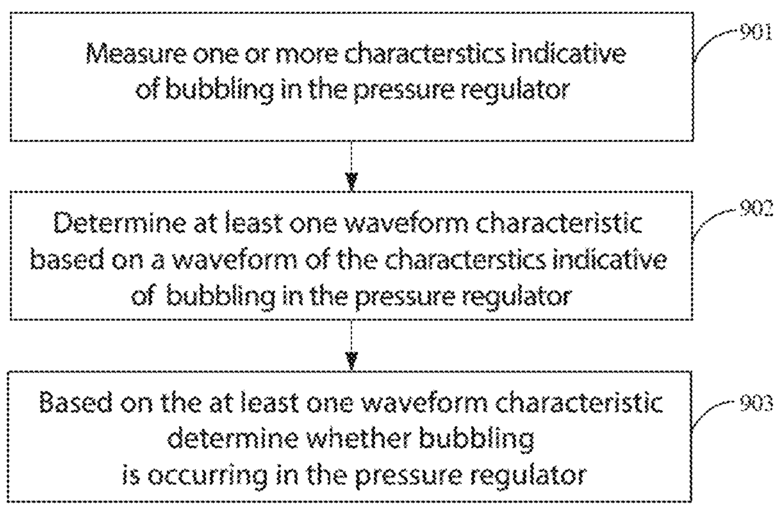
FIG. 11 illustrates an example of an embodiment of the bubbling detection algorithm.

FIG. 11 illustrates an example method of determining whether bubbling is occurring—which is described in more detail below.

At step 901, at least one characteristic indicative of bubbling in the pressure regulator are measured (as described in more detail below).

At step 902, one or more waveform characteristics are determined based on the based on a waveform of the measured at least one characteristic indicative of bubbling in the pressure regulator (for example flow rate and/or pressure as described in more detail below).

At step 903, whether bubbling is occurring in the pressure regulator is determined, based on the at least one waveform characteristic.

Figure 11A:
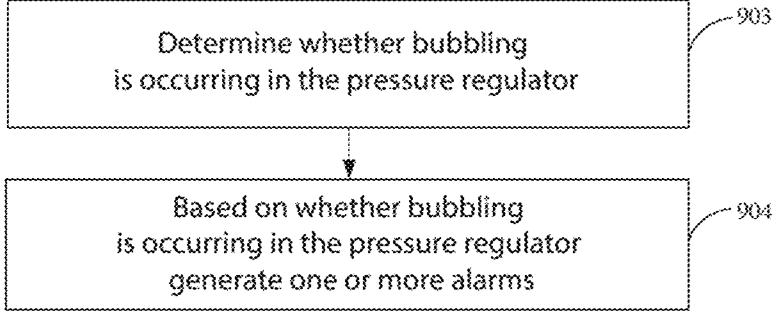
FIG. 11A illustrates an example of generating one or more alarms based on whether bubbling is occurring.

FIG. 11A illustrates an example of generating one or more alarms based on whether bubbling is occurring (described in more detail below).

At step 903, whether bubbling is occurring in the pressure regulator is determined.

At step 904, one or more alarms is generated based on whether bubbling is occurring in the pressure regulator.

Figure 12:
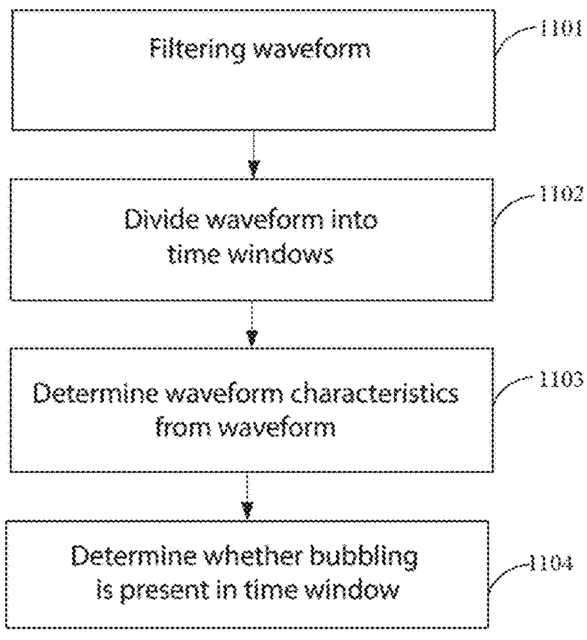
FIG. 12 illustrates an example of an embodiment of the bubbling detection algorithm.

FIG. 12 illustrates an example of the overall architecture according to an embodiment of the bubbling detection algorithm.

At step 1101, the flow signal and/or pressure signal as a waveform is filtered. For example, a high pass FIR filter with cut-off frequency at, for example, 2 Hz and 21 Hz may be applied to the raw signal to remove any DC offset. The flow signal and/or pressure signal may be derived from a flow sensor and a pressure sensor respectively.

At step 1102, waveform is then divided into one or more time windows.

In some embodiments, the waveform may be divided into a one or more time windows.

The determination of whether bubbling is occurring may be made for each time window.

In some embodiments, each time window may be about 1 second to about 6 seconds, or about 1.5 seconds to about 3 seconds, about 1 seconds to about 180 seconds, about 1 seconds to about 60 seconds, about 1 seconds to about 30 seconds.

In some embodiments, each time window may overlap with a preceding time window and/or a subsequent time window.

In some embodiments, the time window overlap may be about 1 second to about 6 seconds, or about 1.5 seconds to about 3 seconds, or about 5 seconds to about 30 seconds, or about 1 seconds to about 60 seconds, or about 1 seconds to about 10 seconds.

Figure 12A:
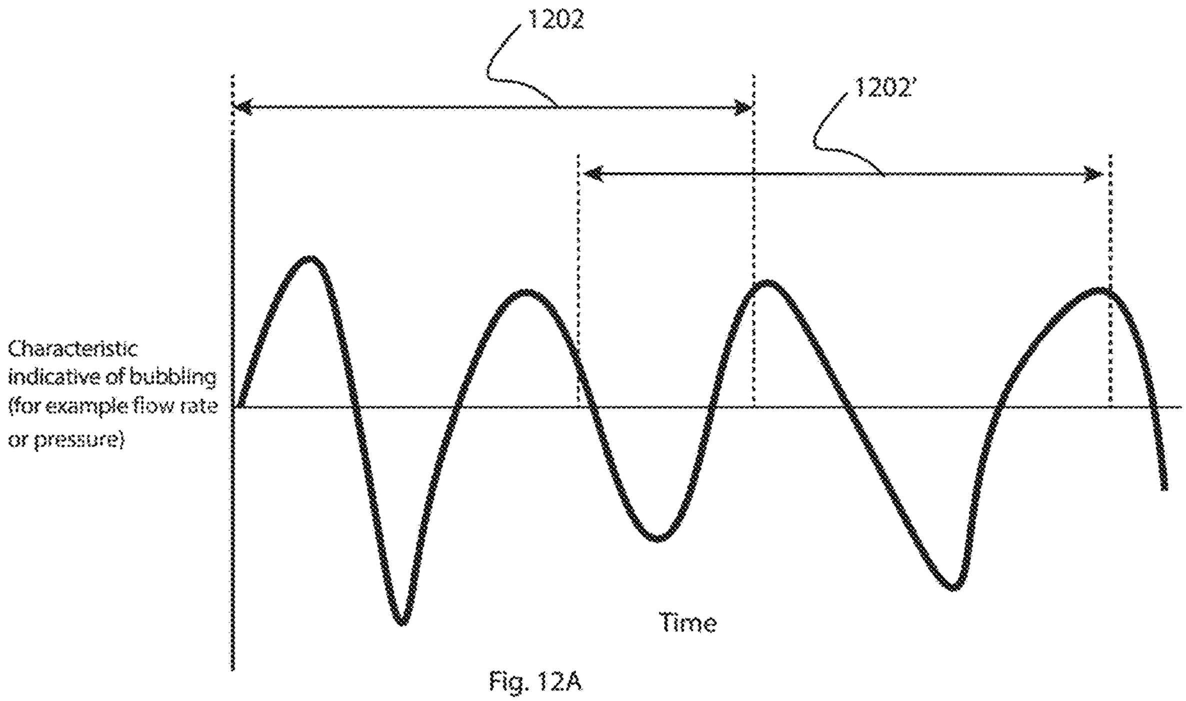
FIG. 12A illustrates a waveform divided into two time windows.

FIG. 12A shows an example of timing windows overlapping timing windows 1202, 1202'.

It will be appreciated that in some embodiments a single timing window is used.

At step 1103, one or more waveform characteristics are determined from the waveform in the time window.

At step 1104, one or more waveform characteristics are used to determine whether bubbling is occurring. The determination of bubbling may be based on a model (as described in more detail below).

As illustrated by FIGS. 13A-13E show examples of a characteristic indicative of bubbling (as a flow rate or pressure signal) as a waveform optionally derived from one or more sensors as described above.

It will be appreciated that the waveform characteristics may equally apply to the method of estimating flow and/or pressure in the gases flow path as described below.

As described above, from the waveform one or more waveform characteristics may be determined.

The one or more waveform characteristics may comprise or be based on: an amplitude of the waveform, a distance between positive peaks of the waveform, and/or an amplitude of the difference between consecutive positive and negative peaks of the waveform. It will be appreciated that the above may be included as part of the characteristics as described below.

It will be appreciated that the following embodiment is described with respect to the term amplitude, however it will be appreciated the term amplitude may be used interchangeably with the term value. Value may be for example the value of the waveform (for example including any DC offset). In some embodiments, any DC offset may be added to the amplitude.

The average and standard deviation (or other statistical characteristics) of each waveform characteristic may be calculated over a time window.

In some embodiments, the waveform characteristic may comprise at least one amplitude characteristic.

In some embodiments, the amplitude characteristic may comprise an average of the amplitude of the waveform optionally over a timing window 1202.

In some embodiments, the amplitude characteristic may comprise an average standard deviation of the amplitude of the waveform optionally over a timing window 1202.

Figure 13A:
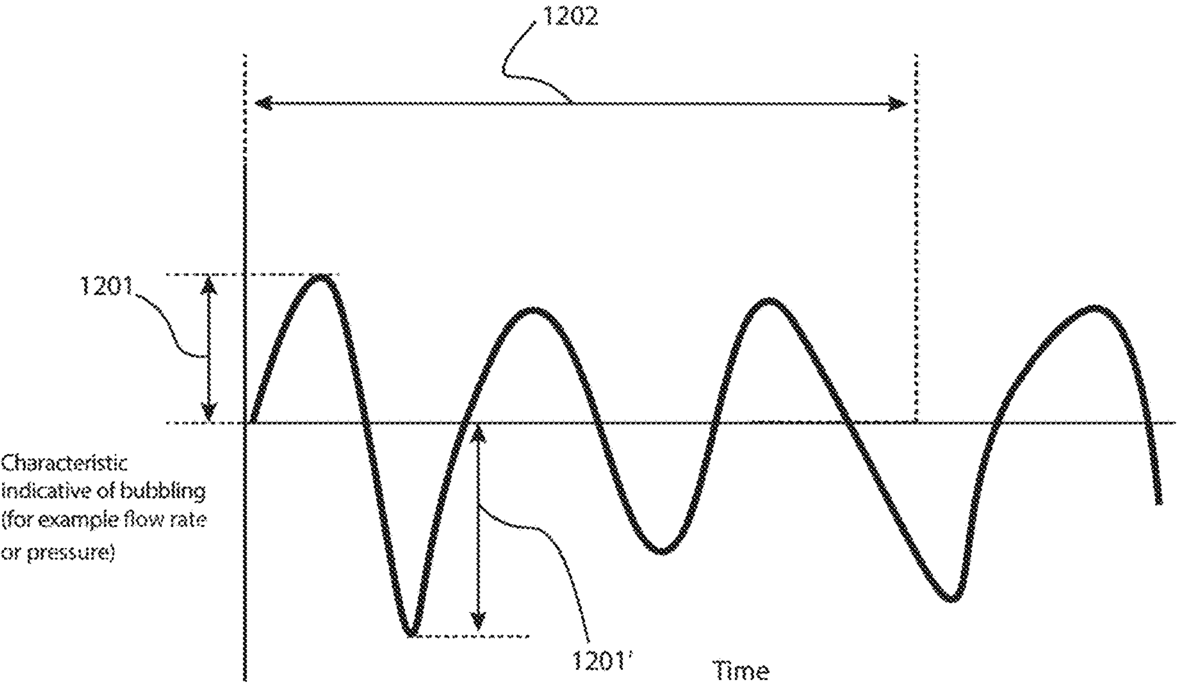
FIGS. 13A-13E illustrate waveform characteristics of a waveform.

In some embodiments, as illustrated in FIG. 13A, the amplitude characteristic may comprise an average of the amplitude of the positive peaks of the waveform optionally over a timing window 1202.

In some embodiments, as illustrated in FIG. 13A, the amplitude characteristic may comprise an average of the amplitude of the negative peaks of the waveform optionally over a timing window 1202.

FIG. 13A illustrates an example of an amplitude of a positive peak of the waveform 1201, and an example of an amplitude of a positive peak of the waveform 1201'.

In some embodiments, the amplitude characteristic comprises a standard deviation of the amplitude of the positive peaks of the waveform optionally over a timing window 1202.

In some embodiments, the amplitude characteristic comprises a standard deviation of the amplitude of the negative peaks of the waveform optionally over a timing window 1202.

It will be appreciated that the amplitude of the positive peak of the waveform can be calculated for each positive peak of the waveform (within a timing window), and then the average of the amplitude of the positive peaks of the waveform and/or the standard deviation of the amplitude of the positive peaks can be calculated.

It will be similarly appreciated that the amplitude of the negative peak of the waveform can be calculated for each negative peak of the waveform (within a timing window), and then the average of the amplitude of the negative peaks of the waveform and/or the standard deviation of the amplitude of the negative peaks can be calculated.

In the example of FIG. 13A, the amplitude of the positive peaks of the waveform is shown, however, as described above, in some embodiments, the amplitude characteristic may comprise an average of the amplitude of the negative peaks of the waveform, and/or a standard deviation of the amplitude of the negative peaks of the waveform optionally over a timing window 1202.

In some embodiments, the waveform characteristic may comprise at least one peak distance characteristic. It will be appreciated that distance in this context may be any time based unit.

Figures 13B, 13C:
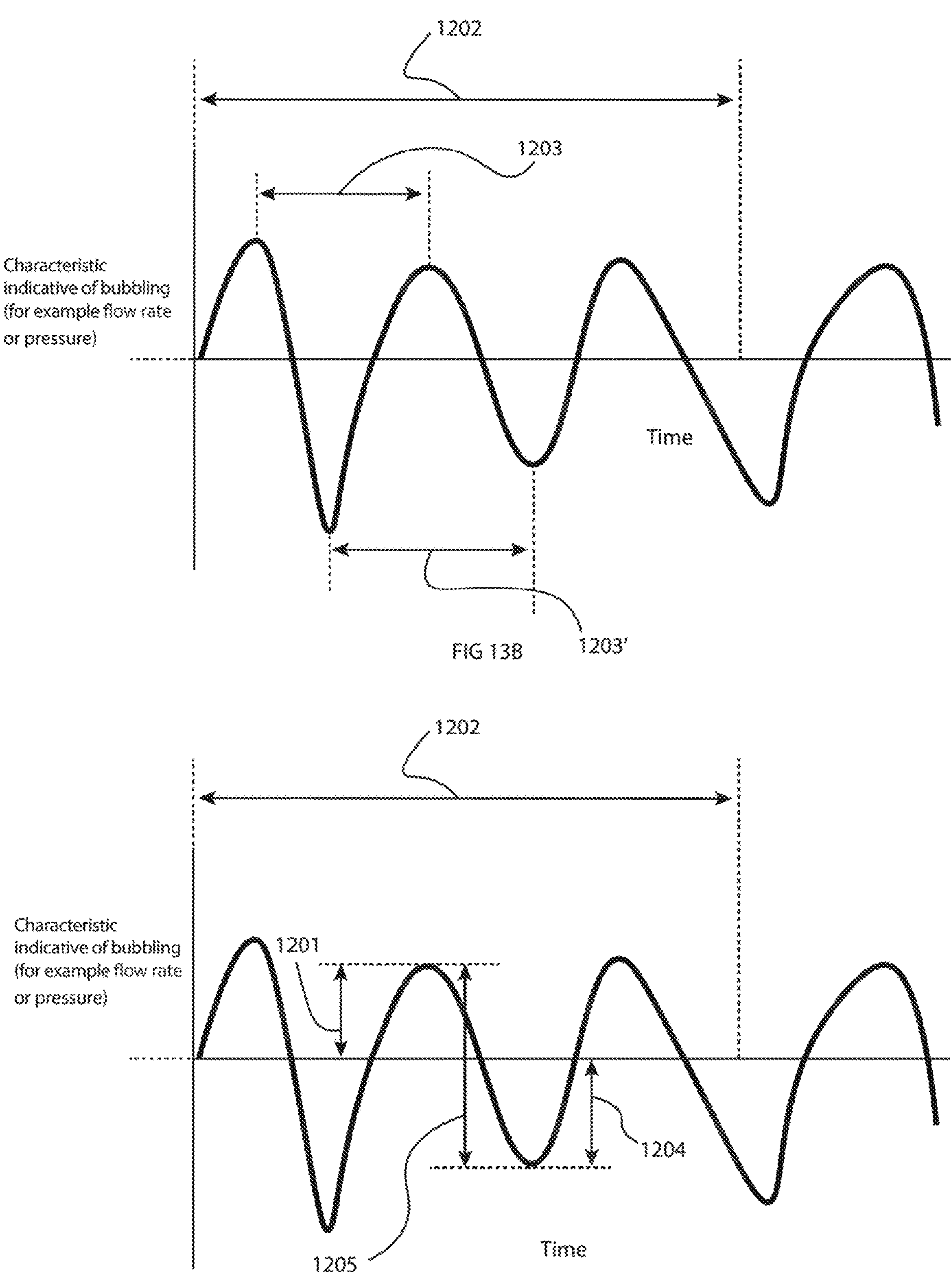

In some embodiments, the peak distance characteristic comprises an average distance between positive peaks of the waveform. FIG. 13B illustrates an example of a distance between two positive peaks of the waveform 1203.

In some embodiments, the peak distance characteristic comprises a standard deviation of the distance between positive peaks.

It will be appreciated that the distance between positive peaks of the waveform can be calculated for each set of adjacent positive peaks of the waveform (within a timing window), and then the average of the distance between positive peaks of the waveform and/or the standard deviation of the distance between positive peak can be calculated.

In some embodiments, the peak distance characteristic comprises an average distance between negative peaks of the waveform. FIG. 13B illustrates an example of a distance between two negative peaks of the waveform 1203'.

In some embodiments, the peak distance characteristic comprises a standard deviation of the distance between negative peaks.

It will be appreciated that the distance between negative peaks of the waveform can be calculated for each set of adjacent negative peaks of the waveform (within a timing window), and then the average of the distance between negative peaks of the waveform and/or the standard deviation of the distance between negative peak can be calculated.

In some embodiments, the waveform characteristic may comprise at least one peak difference characteristic.

In some embodiments, as illustrated in FIG. 13C, the peak difference characteristic comprises an average of the magnitude of the amplitude difference between consecutive positive and negative peaks of the waveform. For example, FIG. 13C illustrates an amplitude of a positive peak of the waveform 1201, and an amplitude of a negative peak of the waveform 1204. The magnitude of the amplitude difference between consecutive positive and negative peaks of the waveform 1205 is calculated based on the sum of the absolute amplitude of the positive peak of the waveform 1201 and the absolute amplitude of a consecutive negative peak of a waveform 1204. It will be appreciated that the waveform of FIG. 13C which shows zero DC offset may be provided with a DC offset. In some embodiments the magnitude of the amplitude difference between consecutive positive and negative peaks of the waveform 1205 may include any DC offset. The DC offset may be determined and added to the magnitude of the amplitude difference between consecutive positive and negative peaks of the waveform 1205.

In some embodiments the magnitude of the amplitude difference between consecutive positive and negative peaks of the waveform 1205 is calculated by taking the difference in the value of the positive peak of the waveform and the value of the consecutive negative peak of the waveform. This approach inherently includes any DC offset in the magnitude of the amplitude difference between consecutive positive and negative peaks of the waveform 1205.

In some embodiments, the peak difference characteristic comprises a standard deviation of the magnitude of the amplitude difference between consecutive positive and negative peaks of the waveform.

It will be appreciated that the magnitude of the amplitude difference between consecutive positive and negative peaks of the waveform can be calculated for consecutive positive peak and negative peak of the waveform (within a timing window), and then the average of the magnitude of the amplitude difference between consecutive positive and negative peaks and/or the standard deviation of the magnitude of the amplitude difference between consecutive positive and negative peaks of the waveform.

The peak difference characteristic may be of particular benefit in determining bubbling because it removes a DC component of the waveform. This approach may be more robust to noise than DC filtering, as an irregular fluctuation might not be removed by a DC filter (depending on filter characteristics) but would be removed in a peak difference characteristic.

In some embodiments, the controller may be configured to apply a high pass and/or a low pass filter to the measurement of the flow rate or pressure and/or the waveform.

As described above, the averages and/or standard deviations (or other statistical measures) may be calculated over the time window.

Determining at least one peak difference characteristic may comprises detecting one or more peaks. Detecting one or more peaks may comprise finding local maxima and minima of the signal. Maxima and minima points may be found in an alternating fashion, for example, a point of local maxima can be found after a local minima, and a new local minima can be found only after a local maxima. The parameter used for peak detection may be the minimum acceptable range between a point of maxima and of minima (MinRangeTh).

It will be appreciated that the term average may apply to any statistical measurement of central tendency, for example mean, median, mode, etc.

In some embodiments, the MinRangeTh may be set to 0.5 L/min when using the filtered signal for bubbling detection.

In some embodiments, the waveform characteristic may comprise at least one crossing characteristic.

Figure 13D:
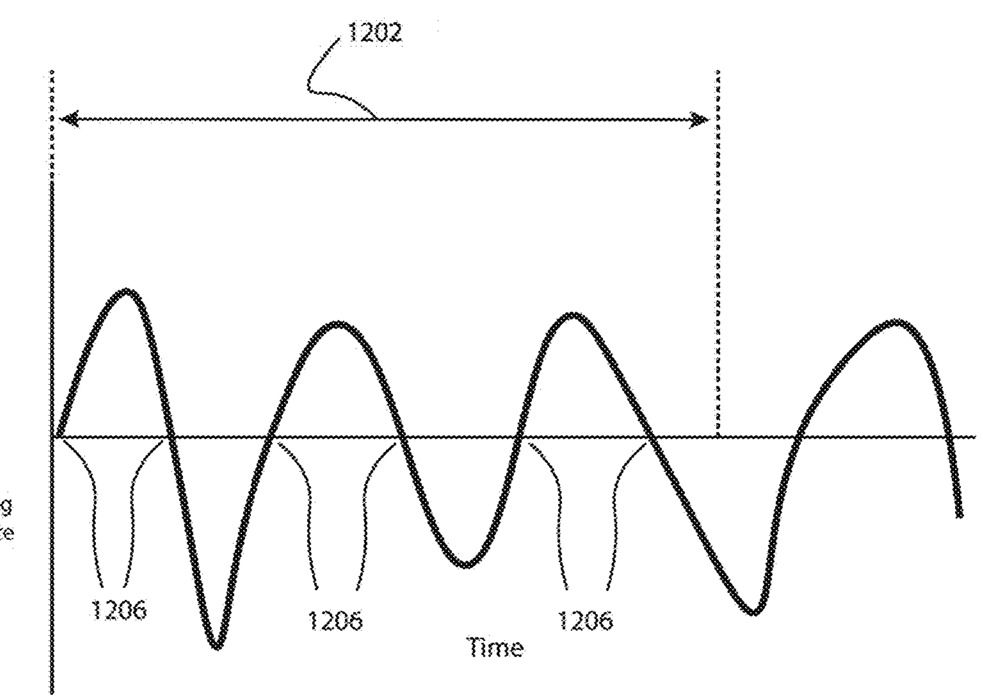

In some embodiments, the crossing characteristic comprises a number of times the waveform crosses 1206 zero (within a timing window). FIG. 13D illustrates an example of the number of times the waveform crosses 1206 zero (within a timing window) being 6.

Figure 13E:
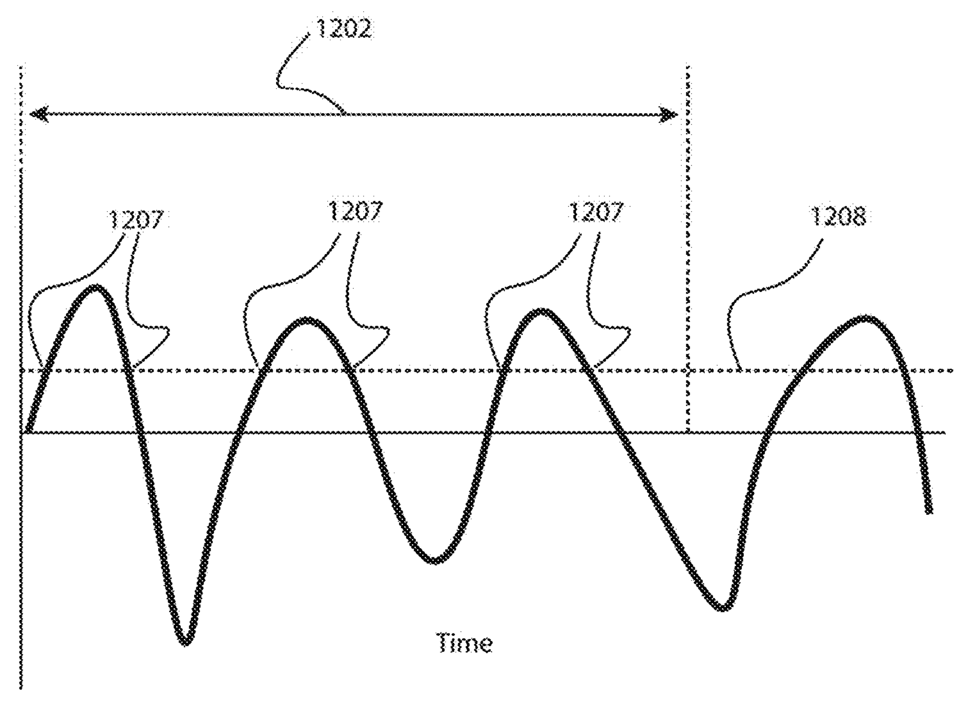

In some embodiments, the crossing characteristic comprises a number of times the waveform crosses 1207 a threshold 1208 (within a timing window). FIG. 13E illustrates an example of the number of times the waveform crosses 1207 a threshold 1208 (within a timing window) being 6.

The threshold may be an average amplitude of the waveform, and/or an average amplitude of positive peaks the waveform, and/or an average amplitude of negative peaks the waveform.

In some embodiments, the threshold may be preset and/or set, or selected by a user.

It will be appreciated that any thresholds, timing windows, timing window overlap, or any features of the models described below may be varied based on a sensitivity setting. For example, a lower sensitivity setting may make the determination of bubbling less sensitive (and therefore more likely to determine bubbling is occurring in edge cases). For example, a higher sensitivity setting may make the determination of bubbling more sensitive (and therefore less likely to determine bubbling is occurring in edge cases.

The sensitivity setting may be based on for example a user setting, or a identify of a component used in the system (as described in more detail elsewhere in the specification).

When determining the at least one crossing characteristic a high pass and/or a low pass filter (for example to remove a DC offset) may be applied to the waveform.

As described at step 1104 a determination of whether bubbling is occurring is based on at least one waveform characteristic as described above.

In some embodiments the determination of whether bubbling is occurring is based on at least one waveform characteristic exceeding an associated threshold.

In some embodiments, the determination of bubbling may be based on a regression model comprising one or more waveform characteristic factors associated with each waveform characteristic.

The waveform characteristic factors may apply weighting to each respective waveform characteristic.

The waveform characteristic factors may be determined experimentally or through machine learning or other supervised learning.

In some embodiments, the determination of bubbling is based an artificial neural network.

In some embodiments, the regression model is a logistic regression (Log Reg) model.

The model may be trained based on supervised learning using positive ('bubbling') samples and negative ('no bubbling') samples. The positive and negative samples may be collected from a range of working conditions for the device. The samples may provide a broad range of scenarios in which bubbling should or should not be detected.

The model may be defined by the function below:

$$\begin{aligned}\text{Bubbling detection output} = {} & w_1 * \text{Average amplitude of positive peaks} + \\ & w_2 * \text{Average distance between poisitive peaks} + w_3 * \text{Average amplitude between consecutive positive and negative peaks} + \\ & w_4 * \text{Standard deviation of amplitude of positive peaks} + \\ & w_5 * \text{Standard deviation of distance between positive peaks} + \\ & w_6 * \text{Standard deviation of amplitude between consecutive positive and negative peaks} + \text{Bias}\end{aligned}$$

Where $w_1$, $w_2$, $w_3$, $w_4$, $w_5$, $w_6$ are factors (for example waveform characteristic factors).

In another configuration, the model may be defined by the function below:

$$\begin{aligned}\text{Bubbling detection output} = {} & w_1 * \text{Average amplitude} + w_2 * \text{Average amplitude of positive peaks} + \\ & w_3 * \text{Average amplitude of negative peaks} + \\ & w_4 * \text{Average distance between positive peaks} + \\ & w_5 * \text{Average distance between negative peaks} + \\ & w_6 * \text{Number of zero crossings} + w_7 * \text{Number of threshold crossings} + \\ & w_8 * \text{Amplitude between consecutive positive and negative peaks} + \\ & w_9 * \text{Standard deviation of average amplitude} + \\ & w_{10} * \text{Standard deviation of amplitude of positive peaks} + \\ & w_{11} * \text{Standard deviation of amplitude of negative peaks} + \\ & w_{12} * \text{Standard deviation of distance between positive peaks} + \\ & w_{13} * \text{Standard deviation of distance between negative peaks} + \\ & w_{14} * \text{Standard deviation of amplitude between consecutive positive and negative peaks} + \text{Bias}\end{aligned}$$

Where $w_1$, $w_2$, $w_3$, $w_4$, $w_5$, $w_6$, $w_7$, $w_8$, $w_9$, $w_{10}$, $w_{11}$, $w_{12}$, $w_{13}$, $w_{14}$ are factors (for example waveform characteristic factors).

The bubbling detection output may be based on a sigmoid function.

The results of the model (for example as implemented in a classifier) is a real number in the range between [0, 1]. The higher the value, the more likely the sample to belong to the 'bubbling' class.

At step 1104, an exponential filter may be applied to the output of the model of each window, which effectively combines the output of sequential time windows.

It will be appreciated that other methods of combining the output of the model for each window are possible for example a low pass filter on the model output or weighting based on the time elapsed since the window, or previous windows (i.e. previous windows have less weighting in the output of the model).

In some embodiments, the determination of whether bubbling is occurring is probability of bubbling occurring between 0 and 1.

In some embodiments, bubbling is determined to be occurring when the probability of bubbling occurring is greater than 0.5.

In some embodiments the determination of whether bubbling is occurring is based on at least one frequency characteristic.

The frequency characteristic may be based on the flow and/or pressure waveform.

The frequency characteristic may comprise at least one frequency band, and a power of the frequency band.

The frequency characteristic may be provided to the bubbling detection model in the same way as the waveform characteristic as described above.

The frequency band may be about 5 Hz and about 20 Hz, or another range in line with bubbling.

As described above the power of the frequency band may be provided to the model to be used in the detection of bubbling.

The location of the flow and/or pressure sensors may also influence bubbling detection. For example, flow and/or pressure sensors located close to the flow generator may sense turbulence in the flow and/or pressure having waveform/spectral properties that overlap with bubbling patterns.

In particular detecting bubbling in an apparatus which may also provide high flow therapy may be difficult as the locations of the sensors may not necessarily be in the optimum location to best determine bubbling. For example, the sensors may be located close the flow generator in the breathing assistance apparatus (as opposed to close to the pressure regulator). Therefore, any sensor noise generated from operation of the apparatus (for example by the flow generator) needs to be distinguished from that of the part of the signal which indicates bubbling in a pressure regulator. The above described embodiment facilitates the removal of noise by using waveform characteristics to isolate the bubbling signal.

Bubbling detection may also be influenced by, for example, atmospheric pressure, temperature, amount of water in the humidifier chamber, and/or gas mixtures.

In some embodiments, the determination of whether bubbling is occurring is based on one or more of an ambient temperature, an altitude of the apparatus, a water level in a humidifier located in the gases pathway.

In some embodiments, the apparatus may be configured to provide a combination of ambient air, and a supplementary gas, and the determination of whether bubbling is occurring is based on the ratio of ambient air to supplementary gas.

In some situations, a component of the flow path (for example the circuit and/or interface) used in the bubble CPAP therapy may influence bubbling detection. For example, the length and diameter of the conduit and interface may affect the waveform.

The component may be identified by the apparatus by one or more methods known in the art (for example by determination of an electrical resistance of a connected component.

In some embodiments, the determination of whether bubbling is occurring may be based on a conduit characteristic of the inspiratory conduit and/or the expiratory conduit.

In some embodiments, the conduit characteristic may comprise one or more of a conduit length, a conduit diameter, and a conduit type.

In some embodiments, the determination of whether bubbling is occurring is based on a characteristic of the patient interface.

If bubbling is detected while the apparatus is connected to a component incompatible with bubble CPAP (for example a conduit, or patient interface which is unsuitable for bubble CPAP therapy) the apparatus may generate an alarm.

The detection of bubbling in the pressure regulator may be useful for ensuring proper use of the breathing assistance apparatus. Proper use of the breathing assistance apparatus is important to ensure effective respiratory therapy or support is provided to the user. A lack of bubbling or irregular bubbling patterns may be indicative of improper use of the breathing assistance apparatus, for example, incorrect peripheral used (e.g. patient interface, conduit, etc.), an improper breathing assistance therapy setup (e.g. pressure regulator connected during high flow therapy mode) or an incorrect therapy mode selected (e.g. high flow therapy mode selected when bubble CPAP mode was required). Bubbling detection may be used to prevent or at least mitigate such improper use that may be detrimental to a user's safety and comfort.

An intermittent bubbling alarm may be generated if bubbling is detected as intermittent. For example, if bubbling is detected and then not detected then the apparatus may determine that the bubbling is intermittent.

The detection that bubbling is intermittent may be indicative that the target flow rate and/or target pressure provided to the patient does not meet the patient demand.

The alarm generated when bubbling is detected as intermittent may also include a recommendation to increase the target flow rate and/or target pressure.

Intermittent bubbling may be detected if a number of transitions between bubbling occurring and bubbling not occurring exceeds a threshold (for example over a time period.)

Additionally, or alternatively, intermittent bubbling may be detected if (for example over a time period) a ratio the time bubbling is not occurring to the time bubbling is occurring is within a range.

Detection of bubbling may be occurring while (for example constantly, or periodically) the apparatus is operating in a non-bubble CPAP mode (for example a high flow therapy mode, and/or a CPAP mode). If bubbling is detected while the apparatus is operating in a non-bubble CPAP mode, the apparatus may generate an alarm (for example indicating to the user that the apparatus may be operating in an incorrect mode and/or to check that the apparatus is in the correct mode). In some configurations, upon detection of bubbling when the apparatus is operating in a non-bubble CPAP mode, the apparatus may automatically change to a bubble CPAP mode.

Detection of bubbling may also be used to indicate whether the patient interface is correctly engaged with the patient. For example, if bubbling is occurring this may be indicative that the patient interface is correctly engaged and if bubbling is not occurring this may be indicative that the patient interface is not engaged.

Determining whether the patient interface is correctly engaged with the patient may additionally or alternatively be based on detection that bubbling is intermittent. Intermittent bubbling may be indicative of a poor seal between the interface and the patient and/or leaks in the system.

In some embodiments, the controller may determine that the patient interface is not engaged with the patient when after detection of bubbling occurring (optionally for a predetermined time) the controller detects that bubbling is not occurring (optionally for a predetermined time).

In some embodiments, the controller may determine that the patient interface is not engaged with the patient when bubbling is not occurring and the flow rate provided by the apparatus is below a threshold.

The controller may generate an alarm if it is determined the patient interface is not engaged.

Detection of bubbling may also be used to determine one or more bubbling time metrics. For example, detection of bubbling during one or more therapy sessions may indicate that therapy is being provided.

The therapy session may be the apparatus providing therapy to a user over a period of time (for example a therapy time). The therapy session may be initiated by a user, and/or by the provision of therapy to a user. The therapy session may be ended by a user, and/or by cessation of provision of therapy to a user. The therapy time may be the time for which the therapy is provided for example as part of a therapy session.

The apparatus may also generate a bubbling index (for example as a bubbling time metric) based on the therapy time and detection of bubbling. The index may be a proportion of the therapy time when detection of bubbling is occurring. The index may for example be presented as a percentage relating to the percentage of the total therapy time for which bubbling is occurring.

The apparatus may also calculate a bubbling time as an bubbling time metric for which bubbling is occurring.

The bubbling time may be used to determine how long therapy was provided for during the therapy session.

The bubbling time may be compared to a threshold time to determine if therapy was provided for a predetermined amount of time.

The apparatus may also calculate a no bubbling time as a bubbling time metrics for which bubbling is not occurring.

The no bubbling time may be used to determine how long therapy was not provided for during the therapy session.

The no bubbling time may be compared to a threshold time to determine if therapy was not provided for a predetermined amount of time.

The apparatus may additionally or alternatively determine a pressure-based metric. The pressure-based metric may be a percentage of therapy time where the pressure delivered to the patient is greater than a threshold pressure. The pressure-based metric may be a percentage of therapy time where the pressure delivered to the patient is greater than a threshold pressure where bubbling is occurring. The pressure delivered to the patient may be for example a pressure at the interface and/or a pressure at the pressure regulator, and/or a pressure at the device.

The pressure metric may be transmitted to a server (or other device), and/or provided as part of a report, as described below in relation to the bubbling time metrics.

The bubbling time metrics may be based on the therapy time for one therapy session, or across a number of therapy sessions.

In some embodiments, one or more alarms may be raised based on the bubbling index (or other bubbling time metric) falling below a threshold (optionally for a predetermined time).

In some embodiments, the controller is configured to indicate that therapy is being provided based on the bubbling index (or other bubbling time metric) is above a threshold.

The apparatus may transmit the bubbling index (or other bubbling time metric) via the wireless data transmitter and/or receiver, or a transceiver 15 to another device (for example a server).

The apparatus may transmit information as to when bubbling is detected via the wireless data transmitter and/or receiver, or a transceiver 15 to another device (for example a server).

The apparatus (and/or server, and/or other device) may determine a trend of one or more bubbling time metrics. The apparatus and/or server, and/or other device may display the trend, or provide the trend to a server and/or other device.

The apparatus (and/or server, and/or other device) may determine an index relating to the whether the one or more bubbling time metric is improving or getting worse. The apparatus and/or server, and/or other device may display the index, or provide the index to a server and/or other device.

A server (for example a remote server) and/or other device, may generate a report based on the information transmitted from the apparatus. As discussed above the information may be one or more bubbling time metric. The information may also be other information related to therapy provided (for example therapy parameters such as humidity, temperature, and/or flow rate).

The report may comprise a trend relating to one or more bubbling time metric, and/or an index relating to one or more bubbling time metric.

The report may be helpful to a clinician to determine whether a patient condition is improving or getting worse. For example, a decreasing therapy time (for example while bubbling is occurring) may indicate an improvement in patient condition and/or that the patient can be transitioned to another therapy type (for example Nasal High Flow therapy). The report may also be useful in determining whether a patient is receiving the desired therapy over a period of time.

The report may indicate one or more bubbling time metric over a period of time (for example a week, or a month etc.)

The bubbling index being maintained above a threshold over a period of time along with a decrease in the bubbling time (or a trend in bubbling time being down) may indicate an improvement in patient condition and/or that the patient can be transitioned to another therapy type (for example Nasal High Flow therapy)

Bubbling in the pressure regulator 134 can also be used to estimate flow and pressure parameters in the system. This is because the characteristics indicative of bubbling may also be indicative of flow and pressure parameters.

In the system examples of FIGS. 1-3A for example no pressure or flow sensors may be located downstream of the apparatus 10 in the gases flow pathway. This allows for a simple system with fewer components, and therefore lower cost. However, a drawback of this type of system is that the apparatus is not able to directly measure the flow or pressure of the gases in the gases pathway downstream of apparatus (i.e., after the thermistor flow rate sensor of sensing circuit board 404).

It will be appreciated that having estimates of the flow and pressure at various locations of the gases flow path may be beneficial in other aspects for example in calibration or sensor redundancy.

In some configurations, the estimated flow and pressure parameters in the system as described may also be undertaken when it is detected that bubbling is occurring (for example as described above).

Figure 14:
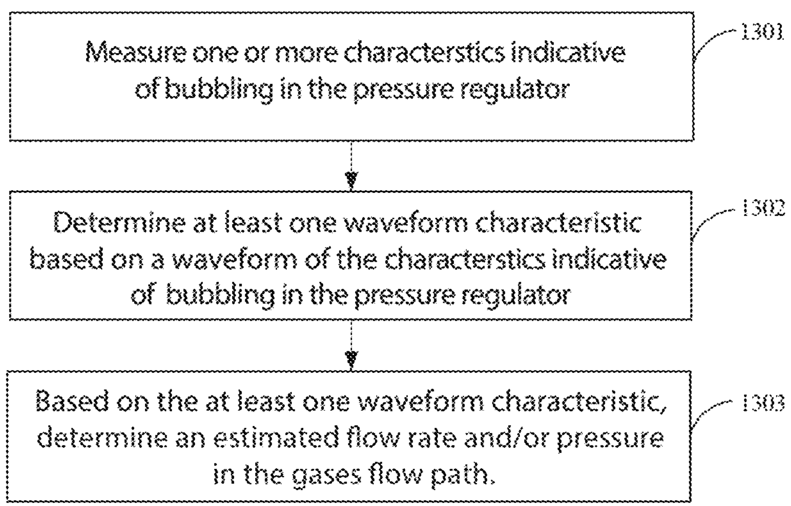
FIGS. 14 and 14A illustrates an example of an embodiment of the flow and/or pressure estimation algorithm.

FIG. 14 illustrates an example of an embodiment of the flow and/or pressure estimation algorithm.

At step 1301, a characteristic of bubbling in the pressure regulator 134 is measured. The characteristic of bubbling in the pressure regulator 134 may be any of the above-described characteristics for example in relation to the detection of bubbling.

However, the below examples (FIG. 14A) use, as an example, flow and pressure measurements (as a signal indicative of a gases flow rate in the gases flow pathway from a flow sensor and/or as a signal indicative of a gases pressure in the gases flow pathway from a pressure sensor).

At step 1302, at least one waveform characteristic is determined based on at least one waveform of the measured characteristic of bubbling in the pressure regulator 134.

At step 1303, an estimated flow rate and/or pressure in the gases flow path is determined based on the at least one waveform characteristic (as discussed as more detail below.

It will be appreciated that the estimated flow rate and/or pressure in the gases flow pathway may be at a position anywhere in the gases flow pathway.

The estimated flow rate and/or pressure in the gases flow pathway may be at a location downstream from the apparatus.

The estimated flow rate of gases at the end of the expiratory conduit may be at the pressure regulator 134.

The estimated flow rate in the gases flow path may be a flow rate through an end of the expiratory conduit 130 at the pressure regulator 134 (for example the open terminal end 136).

The estimated flow rate in the gases flow path may be a flow rate at the apparatus.

The estimated pressure in the gases flow path may be a pressure at a patient interface.

The estimated pressure in the gases flow path may be a pressure at the pressure regulator 134 (for example a pressure set point at the pressure regulator 134).

The estimated pressure in the gases flow path may be a pressure at an end of the expiratory conduit 130 at the pressure regulator 134 (for example the open terminal end 136).

The estimated pressure in the gases flow path may be a pressure at the apparatus.

The estimated flow rate in the gases flow path may be a flow rate through an end of the expiratory conduit 130 at the pressure regulator 134 (for example the open terminal end 136).

In addition to, or alternatively to the at least one characteristic of bubbling in the pressure regulator 134 as described above, the at least one characteristic of bubbling in the pressure regulator 134 may be based on one or more of:

- a signal indicative of an image of the bubbler as an output of a visual sensor,
- a signal indicative of the surface of the water in the bubbler as an output of a water level sensor,
- a signal indicative of the sound generated by the bubbler as an output of a microphone,
- a signal indicative of the optical properties of the liquid in the bubbler as an output of an optical sensor,
- a signal indicative of a gas flow characteristic, as an output of a gas flow characteristic sensor.

The sensors as described above may be located at any point in the system (for example in the apparatus, in the gases flow path (for example in the inspiratory and/or expiratory conduit and/or any connectors), the patient interface and/or in the pressure regulator 134).

The at least one characteristic of bubbling in the pressure regulator 134 may be based on a signal indicative of a gases flow rate in the gases flow pathway.

Figure 14A:
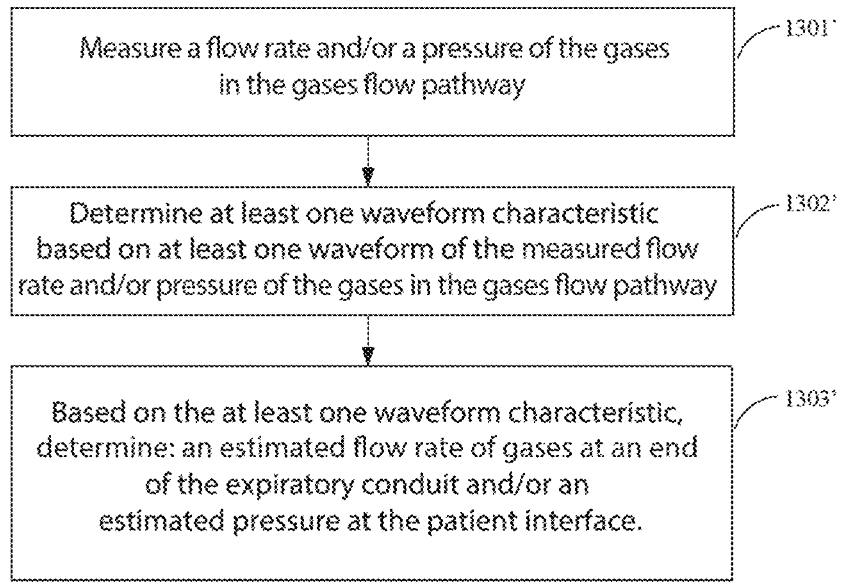

The at least one characteristic of bubbling in the pressure regulator 134 may be based on a signal indicative of a gases flow rate in the gases flow pathway, optionally as an output of a flow sensor (for example a measured flow rate of the gases in the gases flow pathway as shown in FIG. 14A).

The signal indicative of a gases flow rate in the gases flow pathway may be (for example measured) at the same, or a different location to where the estimated flow rate and/or estimated flow rate in the gases flow pathway is determined.

The at least one characteristic of bubbling in the pressure regulator 134 may be based on a signal indicative of a gases pressure in the gases flow pathway, optionally as an output of a pressure sensor (for example a measured pressure of the gases in the gases flow pathway as shown in FIG. 14A).

The signal indicative of a gases pressure rate in the gases flow pathway may be (for example measured) at the same, or a different location to where the estimated flow rate and/or estimated flow rate in the gases flow pathway is determined.

FIG. 14A illustrates an example of an embodiment of the flow and/or pressure estimation algorithm.

At step 1301', a flow rate and/or a pressure of the gases in the gases flow pathway is measured.

As described above, the flow rate and/or a pressure of the gases in the gases flow pathway may be measured at the same, or a different location to where the estimated flow rate and/or estimated flow rate in the gases flow pathway is determined.

At step 1302', at least one waveform characteristic is determined based on at least one waveform of the measured flow rate and/or pressure.

At step 1303', an estimated flow rate at the end of the expiratory conduit and/or estimated pressure at the patient interface is determined based on the at least one waveform characteristic.

In the example embodiment of FIG. 14A the estimated flow rate is an estimated flow rate of gases at an end of the expiratory conduit and the estimated pressure is an estimated pressure at the patient interface.

The estimated flow rate of gases at the end of the expiratory conduit may be at the pressure regulator 134.

The estimated flow rate in the gases flow path may be a flow rate through an end of the expiratory conduit 130 at the pressure regulator 134 (for example the open terminal end 136).

In the embodiment of FIG. 14A the at least one characteristic of bubbling in the pressure regulator 134 is a signal indicative of a gases flow rate in the gases flow pathway and a signal indicative of a gases pressure in the gases flow pathway (based on a measured flow and a measured pressure).

Based on the estimated flow rate and/or pressure in the gases flow pathway, the apparatus (for example by controller 13) may generate one or more alarms. If the estimated flow rate and/or pressure in the gases flow path is greater than, and/or less than, a threshold.

Figure 14B:
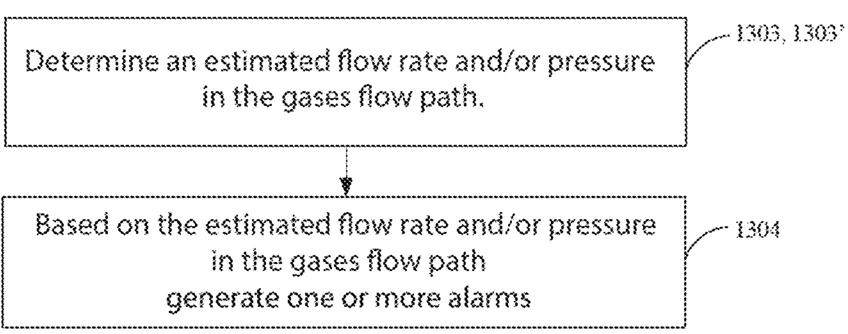
FIG. 14B illustrates an example of generating one or more alarms based on whether bubbling is occurring.

FIG. 14B illustrates an example of generating one or more alarms based on the estimated flow rate and/or pressure in the gases flow pathway (described in more detail below).

At step 1303, 1303', an estimated flow rate and/or pressure in the gases flow path is determined.

At step 1304, one or more alarms is generated based estimated flow rate and/or pressure in the gases flow path.

In some configurations (for example in the embodiment of FIG. 14A) the controller may generate an alarm based on estimated flow rate of gases through the pressure regulator 134 and/or the estimated pressure at a patient interface.

The breathing assistance apparatus of any one of claims 1 to 3, wherein the controller is configured to generate an alarm if the estimated flow rate of gases through the pressure regulator 134 is above a threshold.

The controller 13 may be configured to generate an alarm if the estimated pressure at the patient interface is above a threshold.

The alarm may be the alarm as described above (for example with respect to the bubbling detection disclosure above).

As described above, the apparatus comprises at least one gases property sensor configured to measure a flow rate of the gases in a gases flow pathway and/or a pressure of the gases in a gases flow pathway.

The apparatus may generate one or more alarms based a comparison between:

- an estimated flow rate and/or pressure in the gases flow pathway, and
- a measured flow rate of the gases in a gases flow pathway and/or a measured pressure of the gases in a gases flow pathway.

The controller 13 may be configured to estimate the pressure at the patient interface additionally based on a relationship between the flow rate of the gases in a gases flow pathway and a pressure of the gases in a gases flow pathway (for example the measured flow rate and pressure of the gases in a gases flow pathway).

The controller 13 may be configured to estimate a leak flow rate of the system based on the difference between the measured flow rate of the gases in a gases flow pathway and the estimated flow rate of gases through the pressure regulator 134. The leak flow rate may for example be indicative of the flow rate of the gases which are lost via leak between the apparatus and an end of the expiratory conduit 130 at the pressure regulator 134 (for example the open terminal end 136). Sources of leak may include mask leak (i.e. caused by an imperfect seal between the interface and the patient), or connection leak (i.e. caused by imperfect connection between components of the system.

The controller 13 may be configured to generate an alarm when the leak flow rate is above a leak threshold The controller 13 may be configured to generate an alarm when the leak flow rate of the system is above a leak threshold.

The controller 13 may be configured to generate an alarm when the leak flow rate increases by more than a leak increase threshold over a predetermined period of time.

The controller 13 may be configured to estimate a set point of the pressure regulator 134 based on the estimated flow rate of gases through the pressure regulator 134 and the estimated pressure at a patient interface.

The controller may be configured to display the estimated pressure at the patient interface on at least one display.

As described at step 1303 a determination of an estimated flow rate and/or estimated pressure of the gases in the gases flow pathway is based on at least one waveform characteristic as described above (with respect to detection of bubbling disclosure above).

It will be appreciated that the waveform characteristics as described above with respect to detection of bubbling are equally applicable to the waveform characteristics as described in determination of the estimated flow rate and/or estimated pressure of the gases in the gases flow pathway.

Figure 15:
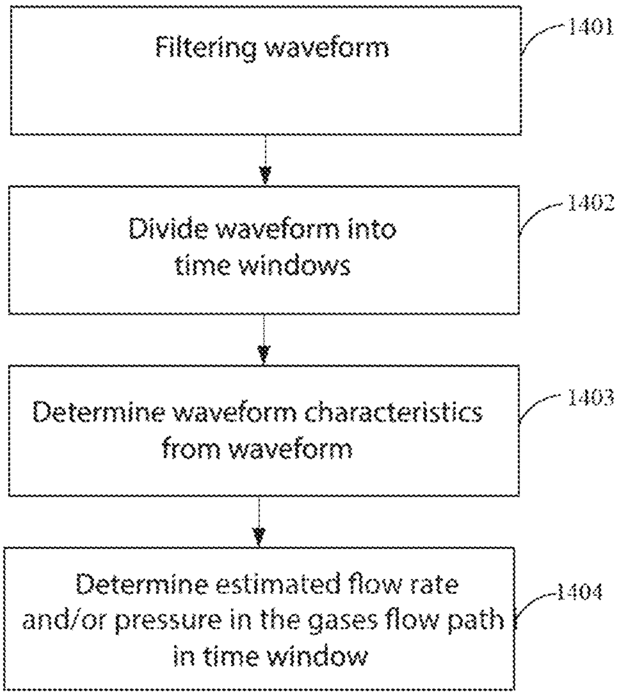
FIG. 15 illustrates an example embodiment of the determination of the estimated flow rate and/or estimated pressure of the gases in the gases flow pathway.

FIG. 15 illustrates an example of the overall architecture according to an embodiment of the determination of the estimated flow rate and/or estimated pressure of the gases in the gases flow pathway.

At step 1401, the waveform of the one or more characteristics indicative of bubbling in the pressure regulator is filtered. For example, a high pass FIR filter with cut-off frequency at, for example, 2 Hz and 21 Hz, or 2 Hz and 40 Hz may be applied to the raw signal to remove any DC offset. The flow signal and/or pressure signal may be derived from a flow sensor and a pressure sensor respectively.

The controller may be configured to apply a high pass and/or a low pass filter to the measurement of the characteristic of bubbling in the pressure regulator.

At step 1402, waveform is then divided into one or more time windows (for example as shown in FIG. 12A).

In some embodiments, the waveform may be divided into a one or more time windows.

The determination of the estimated flow rate and/or estimated pressure of the gases in the gases flow pathway may be made for each time window.

In some embodiments, each time window may be about 1 second to about 6 seconds, or about 1.5 seconds to about 3 seconds, about 1 seconds to about 180 seconds, about 1 seconds to about 60 seconds, about 1 seconds to about 30 seconds.

In some embodiments, each time window may overlap with a preceding time window and/or a subsequent time window.

In some embodiments, the time window overlap may be about 1 second to about 6 seconds, or about 1.5 seconds to about 3 seconds, or about 5 seconds to about 30 seconds, or about 1 seconds to about 60 seconds, or about 1 seconds to about 10 seconds.

FIG. 12A shows an example of timing windows overlapping timing windows 1202, 1202'.

It will be appreciated that in some embodiments a single timing window is used.

At step 1403, one or more waveform characteristics are determined from the waveform in the time window.

At step 1404, one or more waveform characteristics are used to determine an estimated flow rate and/or estimated pressure of the gases in the gases flow pathway. The determination of the estimated flow rate and/or estimated pressure of the gases in the gases flow pathway may be based on a model (as described in more detail below).

The disclosure above with respect to time windows in bubbling detection is equally applicable to the estimation of flow and pressure.

In some embodiments the determination of an estimated flow rate and/or estimated pressure of the gases in the gases flow pathway is based on at least one waveform characteristic exceeding an associated threshold.

In some embodiments, the determination of bubbling may be based on a regression model comprising one or more waveform characteristic factors associated with each waveform characteristic.

The waveform characteristic factors may apply weighting to each respective waveform characteristic.

The waveform characteristic factors may be determined experimentally or through machine learning or other supervised learning.

In some embodiments, the determination of an estimated flow rate and/or estimated pressure of the gases in the gases flow path is based an artificial neural network.

In some embodiments, the regression model is a logistic regression (Log Reg) model.

The model may be trained based on supervised learning using measured flow rate and pressures in the gases pathway. The samples may be collected from a range of working conditions for the device. The samples may provide a broad range of scenarios in for the apparatus.

The model may be defined by the function below:

$$
\begin{aligned}
&\text{Estimated flow rate and/or pressure} = \\
&w_1 * \text{Average amplitude} + w_2 * \text{Average amplitude of positive peaks} + \\
&w_3 * \text{Average amplitude of negative peaks} + \\
&w_4 * \text{Average distance between positive peaks} + \\
&w_5 * \text{Average distance between negative peaks} + \\
&w_6 * \text{Number of zero crossings} + w_7 * \text{Number of threshold crossings} + \\
&w_8 * \text{Amplitude between consecutive positive and negative peaks} + \\
&w_9 * \text{Standard deviation of average amplitude} + \\
&w_{10} * \text{Standard deviation of amplitude of positive peaks} + \\
&w_{11} * \text{Standard deviation of amplitude of negative peaks} + \\
&w_{12} * \text{Standard deviation of distance between positive peaks} +
\end{aligned}
$$

-continued $$w_{13} * \text{Standard deviation of distance between negative peaks} + w_{14} * \text{Standard deviation of amplitude between consecutive positive and negative peaks} + \text{Bias}$$

Where $w_1$, $w_2$, $w_3$, $w_4$, $w_5$, $w_6$, $w_7$, $w_8$, $w_9$, $w_{10}$, $w_{11}$, $w_{12}$, $w_{13}$, $w_{14}$ are factors (for example waveform characteristic factors).

At step 1404, an exponential filter may be applied to the output of the model of each window, which effectively combines the output of sequential time windows.

It will be appreciated that other methods of combining the output of the model for each window are possible for example a low pass filter on the model output or weighting based on the time elapsed since the window, or previous windows (i.e. previous windows have less weighting in the output of the model).

In some embodiments the determination of the estimated flow rate and/or estimated pressure of the gases in the gases flow pathway is additionally, or alternatively, based on at least one frequency characteristic.

The frequency characteristic may be based on the one or more characteristics indicative of bubbling waveform.

The frequency characteristic may comprise at least one frequency band, and a power of the frequency band.

The frequency characteristic may be provided to the estimated flow rate and/or estimated pressure model in the same way as the waveform characteristic as described above.

The frequency band may be about 5 Hz and about 20 Hz, or another range in line with bubbling (or the one or more characteristics indicative of bubbling).

As described above the power of the frequency band may be provided to the model to be used in the determination of the estimated flow rate and/or estimated pressure of the gases in the gases flow pathway.

The location of the flow and/or pressure sensors may also influence the estimated flow rate and/or estimated pressure of the gases in the gases flow pathway. For example, flow and/or pressure sensors located close to the flow generator may sense turbulence in the flow and/or pressure having waveform/spectral properties that overlap with the one or more characteristics indicative of bubbling.

In particular detecting the one or more characteristics indicative of bubbling in an apparatus which may also provide high flow therapy may be difficult as the locations of the sensors may not necessarily be in the optimum location to best determine the one or more characteristics indicative of bubbling. For example, the sensors may be located close the flow generator in the breathing assistance apparatus (as opposed to close to the pressure regulator). Therefore, any sensor noise generated from operation of the apparatus (for example by the flow generator) needs to be distinguished from that of the part of the signal which indicative of bubbling in a pressure regulator. The above described embodiment facilitates the removal of noise by using waveform characteristics to isolate the bubbling signal.

The one or more characteristics indicative of bubbling may also be influenced by, for example, atmospheric pressure, temperature, amount of water in the humidifier chamber, and/or gas mixtures.

In some embodiments, the determination of the estimated flow rate and/or estimated pressure of the gases in the gases flow pathway is based on one or more of an ambient temperature, an altitude of the apparatus, a water level in a humidifier located in the gases pathway.

In some embodiments (as described in more detail above), the apparatus may be configured to provide a combination of ambient air, and a supplementary gas, and the determination of whether the estimated flow rate and/or estimated pressure of the gases in the gases flow pathway is based on the ratio of ambient air to supplementary gas.

In some situations, a component of the flow path (for example the circuit and/or interface) used in the bubble CPAP therapy may influence the one or more characteristics indicative of bubbling. For example, the length and diameter of the conduit and interface may affect the waveform.

The component may be identified by the apparatus by one or more methods known in the art (for example by determination of an electrical resistance of a connected component.

The determination of the estimated flow rate and/or estimated pressure of the gases in the gases flow path (for example the flow rate of gases through the pressure regulator and/or the pressure at a patient interface) may be based on a conduit characteristic of the inspiratory conduit and/or the expiratory conduit.

The conduit characteristic may comprise one or more of:

conduit length, conduit diameter, a conduit type.

The determination the estimated flow rate and/or estimated pressure of the gases in the gases flow path may be based on a characteristic of the patient interface. For example, different interfaces may have effects on bubbling in the pressure regulator. Different interfaces for example may have different waveform characteristic factors.

It will be appreciated that any features of the bubbling detection may be combined with any features of the flow and pressure estimation.

When it is described as the apparatus undertaking an action it may be one or more controllers of the apparatus undertaking the action as part of the apparatus. Further when it is described as a controller undertaking an action it will be appreciated that the action could be undertaken by one or more controllers (or processors of a controller) in a distributed controller setup.

In this disclosure, the terms controller and hardware controller can be interchangeable. For example, a controller or hardware controller can be a microprocessor or a CPU with software instructions to control other components.

Methods and processes described may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some configurations a module may be separately compiled, in other configurations a module may represent a subset of instructions of a separately compiled program, and may not have an interface available to other logical program units.

In certain configurations, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations, one or more features from a claimed combination can, in some cases, be excised from the combination, and the combination may be claimed as a sub-combination or variation of a sub-combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language used herein, such as, among others, “can,” “could,” “might,” “may,” “e.g.,” and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms “comprising,” “including,” “having,” and the like are synonymous and are used inclusively, in an open-ended fashion, and do not exclude additional elements, features, acts, operations, and so forth. Also, the term “or” is used in its inclusive sense (and not in its exclusive sense) so that when used, for example, to connect a list of elements, the term “or” means one, some, or all of the elements in the list.

Conjunctive language such as the phrase “at least one of X, Y, and Z,” unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms “approximately,” “about,” “generally,” and “substantially” as used herein represent a value, amount, or characteristic close to the stated value, amount, or characteristic that still performs a desired function or achieves a desired result. For example, the terms “approximately”, “about”, “generally,” and “substantially” may refer to an amount that is within less than 10% of, within less than 5% of, within less than 1% of, within less than 0.1% of, and within less than 0.01% of the stated amount. As another example, in certain embodiments, the terms “generally parallel” and “substantially parallel” refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication. For example, actions such as “controlling a motor speed” include “instructing controlling of a motor speed.”

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

The invention claimed is:

1. A breathing assistance apparatus for providing respiratory therapy, the breathing assistance apparatus comprising:

- a flow generator, the flow generator configured to provide a flow of gases to an inspiratory conduit at a target flow rate;
- at least one gases property sensor, the at least one gases property sensor configured to measure a flow rate or a pressure of the gases in a gases flow pathway,
- wherein the gases flow pathway comprises at least the inspiratory conduit configured to be connected to a patient interface, and an expiratory conduit configured to be connected to the patient interface and a pressure regulator, the pressure regulator comprising a chamber with a column of a liquid into which an end portion of the expiratory conduit is submerged; and
- a controller, the controller configured to:
  - determine at least one waveform characteristic based on a waveform of the measured flow or pressure, and
  - based on the at least one waveform characteristic, determine whether bubbling is occurring in the pressure regulator;
- wherein the at least one waveform characteristic comprises at least one peak distance characteristic, and wherein the peak distance characteristic comprises one or more of:
  - an average distance between positive peaks of the waveform over a first time window, or
  - a standard deviation of a distance between positive peaks of the waveform over a second time window.

2. The breathing assistance apparatus of claim 1, wherein the determination of whether bubbling is occurring is based on determining pressure and/or flow oscillations in the waveform indicative of bubbling in the pressure regulator.

3. The breathing assistance apparatus of claim 1, wherein the controller is configured to display whether bubbling is occurring in the pressure regulator on a display.

4. The breathing assistance apparatus of claim 1, wherein the controller is configured to generate an alarm based on whether bubbling is occurring in the pressure regulator, and wherein the controller is configured to generate the alarm if it is determined bubbling is not occurring in the pressure regulator.

5. The breathing assistance apparatus of claim 4, wherein the controller is configured to generate the alarm if it is determined: a percentage of time bubbling is occurring over a time period is below a threshold, or the percentage of time bubbling is not occurring over a time period is above a threshold.

6. The breathing assistance apparatus of claim 1, wherein the controller automatically selects a respiratory therapy mode based on whether bubbling is occurring in the pressure regulator.

7. The breathing assistance apparatus of claim 6, wherein the respiratory therapy mode comprises a bubble CPAP therapy mode and a high flow therapy mode.

8. The breathing assistance apparatus of claim 1, wherein the controller is configured to generate an alarm when bubbling is detected in a non-bubble CPAP mode.

9. The breathing assistance apparatus of claim 1, wherein the determination of whether bubbling is occurring is based on at least one waveform characteristic exceeding an associated threshold.

10. The breathing assistance apparatus of claim 1, wherein the determination of whether bubbling is occurring is based on a model, the model comprising one or more waveform characteristic factors associated with each waveform characteristic.

11. The breathing assistance apparatus of claim 1, wherein the at least one waveform characteristic comprises or is based on one or more of:

- an amplitude of the waveform,
- a distance between positive peaks of the waveform,
- a magnitude of an amplitude difference between consecutive positive and negative peaks of the waveform.

12. The breathing assistance apparatus of claim 1, wherein the at least one waveform characteristic comprises at least one amplitude characteristic, and wherein the amplitude characteristic comprises one or more of:

an average of an amplitude of positive peaks of the waveform over a first time window, a standard deviation of the amplitude of the positive peaks of the waveform over a second time window.

13. The breathing assistance apparatus of claim 1, wherein the at least one waveform characteristic comprises at least one peak difference characteristic, and wherein the peak difference characteristic comprises one or more of:

an average of a magnitude of an amplitude difference between consecutive positive and negative peaks of the waveform over a first time window, a standard deviation of the magnitude of the amplitude difference between consecutive positive and negative peaks of the waveform over a second time window.

14. The breathing assistance apparatus of claim 1, wherein the at least one gases property sensor is located at one or more of:

in the breathing assistance apparatus, within the flow generator, in the patient interface, in the pressure regulator, in the inspiratory conduit, in the expiratory conduit.

15. The breathing assistance apparatus of claim 1, wherein the controller is configured to determine that bubbling is intermittent based on a ratio of time bubbling is occurring to time bubbling is not occurring over a time period, and wherein the controller is configured to determine that bubbling is intermittent when the ratio of the time bubbling is occurring to time bubbling is not occurring is within a range.

16. The breathing assistance apparatus of claim 1, wherein detection of bubbling occurring in the pressure regulator during a therapy session indicates that therapy is being provided.

17. The breathing assistance apparatus of claim 1, wherein the controller is configured to determine one or more indicators of bubbling time metrics based on detection of bubbling during one or more therapy sessions, and wherein the one or more indicators of bubbling time metrics is one or more of:

a bubbling index, wherein the bubbling index is a percentage of a total therapy time for which bubbling is occurring, a no bubbling time for which bubbling is not occurring, or a bubbling time for which bubbling is occurring.

18. The breathing assistance apparatus of claim 17, wherein the controller is configured to generate an alarm when one or more of the indicators of bubbling time metrics falls below a first threshold and/or indicate that therapy is being provided when one or more of the indicators of bubbling time metrics are above a second threshold.

19. The breathing assistance apparatus of claim 1, wherein the controller is configured to detect intermittent bubbling and when the controller detects intermittent bubbling, the controller indicates the target flow rate or a target pressure provided to the patient does not meet a patient demand.

* * * * *